(12) United States Patent
Smrzka et al.

(10) Patent No.: US 12,065,509 B2
(45) Date of Patent: *Aug. 20, 2024

(54) SUBSTANCES AND METHODS FOR THE USE IN PREVENTION AND/OR TREATMENT IN HUNTINGON'S DISEASE

(71) Applicant: HD IMMUNE GMBH, Vienna (AT)

(72) Inventors: Oskar Smrzka, Vienna (AT); Stefan Bartl, Vienna (AT); Michela Parth, Vienna (AT)

(73) Assignee: HD IMMUNE GMBH, Vienna (AT)

(*) Notice: Subject to any disclaimer, the term of this patent is extended or adjusted under 35 U.S.C. 154(b) by 0 days.

This patent is subject to a terminal disclaimer.

(21) Appl. No.: 17/520,141

(22) Filed: Nov. 5, 2021

(65) Prior Publication Data

US 2022/0073650 A1    Mar. 10, 2022

Related U.S. Application Data

(60) Division of application No. 16/996,031, filed on Aug. 18, 2020, now abandoned, which is a continuation of application No. 16/025,095, filed on Jul. 2, 2018, now abandoned, which is a continuation of application No. 15/323,461, filed as application No. PCT/EP2015/065795 on Jul. 10, 2015, now Pat. No. 10,053,518.

(30) Foreign Application Priority Data

Jul. 10, 2014  (EP) .................................. 14176609

(51) Int. Cl.
| | |
|---|---|
| C07K 17/02 | (2006.01) |
| C07K 16/18 | (2006.01) |
| G01N 33/577 | (2006.01) |
| G01N 33/68 | (2006.01) |

(52) U.S. Cl.
CPC .............. *C07K 17/02* (2013.01); *C07K 16/18* (2013.01); *G01N 33/577* (2013.01); *G01N 33/6896* (2013.01); *C07K 2317/24* (2013.01); *C07K 2317/34* (2013.01); *C07K 2317/56* (2013.01); *C07K 2317/565* (2013.01); *G01N 2800/2835* (2013.01)

(58) Field of Classification Search
None
See application file for complete search history.

(56) References Cited

U.S. PATENT DOCUMENTS

| | | | |
|---|---|---|---|
| 2003/0232052 A1 | 12/2003 | Khoshnan et al. | |
| 2005/0112139 A1* | 5/2005 | Karp | C07K 14/005 |
| | | | 424/188.1 |
| 2007/0026029 A1 | 2/2007 | Mattner et al. | |
| 2008/0107657 A1 | 5/2008 | Khoshnan et al. | |
| 2010/0233180 A1 | 9/2010 | Khoshnan et al. | |
| 2010/0305492 A1 | 12/2010 | Lad et al. | |
| 2011/0166327 A1 | 7/2011 | Mattner et al. | |

FOREIGN PATENT DOCUMENTS

JP    2007-504863    3/2007

OTHER PUBLICATIONS

Almagro et al. Frontiers in Bioscience 13:1619-1633, 2008.*
Lloyd et al. Protein Engineering, Design & Selection vol. 22, No. 3 pp. 159-168, 2009.*
International Search Report and Written Opinion issued on Oct. 9, 2015 in PCT/EP2015/065795.
International Preliminary Report on Patentability issued on Oct. 11, 2016 in PCT/EP2015/065795.
Extended European Search Report issued on Dec. 16, 2014 in Patent Application No. 14176609.7.
Andreas Weiss, et al., "Single-step detection of mutant huntingtin in animal and human tissues: A bioassay for Huntington's disease", Analytical Biochemistry, vol. 395, 2009, pp. 8-15.
David C. Butler, et al., "Engineered antibody therapies to counteract mutant huntingtin and related toxic intracellular proteins", Progress in Neurobiology, 2011, pp. 190-204.
Xuesong Chen, et al., "Expanded Polyglutamine-Binding Peptoid as a Novel Therapeutic Agent for Treatment of Huntington's Disease", Chemistry & Biology, vol. 18, 2011, pp. 1113-1125.
Marianne J.U. Novak, et al., "Huntington's Disease: Clinical Presentation and Treatment", International Review of Neurobiology, vol. 98, 2011, pp. 297-323.
Shenliang Yu, et al., "Drugging unconventional targets: insights from Huntington's disease", Trends in Pharmacological Sciences, vol. 35, No. 2, 2014, pp. 53-62.
Jonathan Bard, et al., "Advances in Huntington Disease Drug Discovery: Novel Approaches to Model Disease Phenotypes", Journal of Biomolecular Screening, vol. 19, No. 2, 2014, pp. 191-204.
Beverly L. Davidson, "Taking a Break from Huntingtin", www.moleculartherapy.org, vol. 20, No. 10, 2012, p. 1838.
Anne Messer, et al. "Intrabodies as Neuroprotective Therapeutics", Neurotherapeutics, 2013, pp. 447-458.
Jan Ko, et al., "New anti-huntingtin monoclonal antibodies: Implications for huntingtin conformation and its binding proteins", Brain Research Bulletin, vol. 56, No. 3/4, 2001, pp. 319-329.
Francesca Persichetti, et al., "Normal and Expanded Huntington's Disease Gene Alleles Produce Distinguishable Proteins Due to Translation Across the CAG Repeat," Molecular Medicine, vol. 1, No. 4, 1995, pp. 374-383.

(Continued)

*Primary Examiner* — Oluwatosin A Ogunbiyi
(74) *Attorney, Agent, or Firm* — Merchant & Gould P.C.

(57) ABSTRACT

A monoclonal antibody may have a binding domain that binds to a peptide of the HTT protein having the sequence of p7543 (SEQ ID No. 3). Such a monoclonal according may include a heavy chain variable region CDR1 comprising GYTFTEYT (SEQ ID No. 66), a heavy chain variable region CDR2 comprising INPNNGGT (SEQ ID No. 67), a heavy chain variable region CDR3 comprising ASLDGRDY (SEQ ID No. 68), a light chain variable region CDR1 comprising QSLLNSRTRKNY (SEQ ID No. 69), a light chain variable region CDR2 comprising WAS (SEQ ID No. 70), and/or a light chain variable region comprising KQSYNLLT (SEQ ID No. 71).

3 Claims, 23 Drawing Sheets

Specification includes a Sequence Listing.

(56) References Cited

OTHER PUBLICATIONS

Andreas Weiss, et al., "Mutant huntingtin fragmentation in immune cells tracks Huntington's disease progression", The Journal of Clinical Investigation, vol. 122, No. 10, 2012, pp. 3731-3736.
Gisa Ellrichmann, et al., "The Role of the Immune System in Huntington's Disease", Clinical and Developmental Immunology, vol. 2013, 2013, pp. 1-11.
Rona K. Graham, et al., "Cleavage at the Caspase-6 Site is Required for Neuronal Dysfunction and Degeneration Due to Mutant Huntingtin", Cell, vol. 125, 2006, pp. 1179-1191.
Bibiana K.Y. Wong, "Delineation of caspase-6 dependent phenotypes in the YAC128 mouse model of Huntington Disease", University of British Columbia, $9^{th}$ Annual Huntington's Disease Therapeutics Conference, 2014, 1 page.
Todd W. Miller, et al., "DNA Vaccination against Mutant Huntingtin Ameliorates the HDR6/2 Diabetic Phenotype", Molecular Therapy, vol. 7, No. 5, 2003, pp. 572-579.
Japanese Office Action issued Jun. 25, 2019 in Japanese Patent Application No. 2017-501203, 3 pages.
A. Mader, et al., "Humanization strategies for an anti-idiotypic antibody mimicking HIV-I gp4I", Protein Engineering, Design and Selection, vol. 23, No. 12, 2010, pp. 947-954.
Nils Lonberg, "Human Antibodies from transgenic animals", Nature Biotechnology, vol. 23, No. 9, 2005, pp. 1117-1125.
Amber L. Southwell, et al., "Perturbation with Intrabodies Reveals That Calpain Cleavage is Required for Degradation of Huntingtin Exon 1", PLoS One, vol. 6, Issue 1, 2011, pp. 1-10.
Simon C. Warby, et al., "Activated caspase-6 and caspase-6-cleaved fragments of huntingtin specifically colocalize in the nucleus", Human Molecular Genetics, vol. 17, No. 15, 2008, pp. 2390-2404.
Markus Mandler, et al., "Next-generation active immunization approach for synucleinopathies: implications for Parkinson's disease clinical trials", Acta Neuropathol, 2014, 19 Pages.
Volker Stadler, et al., "Combinatorial Synthesis of Peptide Arrays with a Laser Printer", Angew. Chem. Int. Ed., vol. 47, 2008, pp. 7132-7135.
Philipp Holliger, et al., "Diabodies': Small bivalent and bispecific antibody fragments", Proc. Natl. Acad. Sci., vol. 90, 1993, pp. 6444-6448.
Xia Zhang, et al., "The isolation and Characterization of Murine Macrophages", Curr Protoc in Immunol, 2008, pp. 1-18.
Manmohan Singh, et al., "Advances in Vaccine Adjuvants", Nature Biotechnology, vol. 17, 1999, pp. 1075-1081.
Derek T. O'Hagan, et al., "Recent Advances in the Discovery and Delivery of Vaccine Adjuvants", Nature Reviews Drug Discovery, vol. 2, 2003, pp. 727-735.
Xiaoyun Liu, et al., "Mapping the Human Plasma Proteome by SCX-LC-IMS-MS", J Am Soc Mass Spectrom, vol. 18, No. 7, 2007, pp. 1-29.

Rona K. Graham, et al., "Cleavage at the 586aa caspase-6 site in mutant huntingtin influences caspase-6 activation in vivo", J Neurosci. vol. 30, No. 45, 2010, pp. 1-22.
Peter Rice, et al., "EMBOSS: The European Molecular Biology Open Software Suite", TIG, vol. 16, No. 6, 2000, pp. 276-277.
Thibaut Pelat, et al., "Obtention and Engineering of Non-Human Primate (NHP) Antibodies for Therapeutics", Mini-Reviews in Medicinal Chemistry, vol. 9, 2009, pp. 1633-1638.
Nicholas Whitelegg, et al., "Antibody Variable Regions Toward a Unified Modeling Method", Methods in Molecular Biology, vol. 248, 2004, pp. 51-91.
Jin Hong Kim, et al., "Humanization by CDR Grafting and Specificity-Determining Residue Grafting", Methods in Molecular Biology, vol. 907, 2012, pp. 237-245.
Jan Modregger, et al., "PACSIN 1 interacts with huntingtin and is absent from synaptic varicosities in presymptomatic Huntington's disease brains," Human Molecular Genetics, vol. 11, No. 21, 2002, pp. 2547-2558.
Remko van Vught, et al., "Site-Specific Functionalization of Proteins and Their Applications To Therapeutic Antibodies," Computational and Structural Biotechnology Journal, vol. 9, Issue 14, 2014, pp. 1-13.
Gülgün Tezel, et al., "Immunoproteomic Analysis of Potential Serum Biomarker Candidates in Human Glaucoma", Investigative Ophthalmology & Visual Science, vol. 53, No. 13, 2012, pp. 8222-8231.
Xiaoyun Liu, et al., "Protein Expression in the Striatum and Cortex Regions of the Brain for a Mouse Model of Huntington's Disease", J Proteome Res. vol. 6, No. 8, 2007, pp. 1-21.
Zhiqiang Zheng, et al., "Huntington's Disease and the Huntingtin Protein", Progress in Molecular Biology and Translational Science, vol. 107, 2012, pp. 189-214.
Ulrike Träger, et al., "HTT-lowering reverses Huntington's disease immune dysfunction caused by NFκB pathway dysregulation", Brain, vol. 137, 2014, pp. 819-833.
Kabat, et al., "Sequences of Proteins of Immunological Interest", vol. 1, Fifth Edition, U.S. Department of Health and Human Services, Public Health Service National Institutes of Health, NIH Publication No. 91-3242, Bethesda, MD, 1991, pp. 1-1240 (available on-line at https://books.google_co.uk/books?id=3iMvZYW2ZtwC&lpg=PA11371A1&pg=PP1#v=onepage&g&f=true).
Butler et al. Progress in Neurobiology 97 (2012) 190-204.
Weiss et al. Analytical Biochemistry, vol. 395, 2009, pp. 8-15.
Gafni et al. J. Neurosci, May 30, 2012; 32(22):7454-7465.
Bendig et al. Methods: A Companion to Methods in Enzymology 1995; 8:83-93.
Brown et al. J. Immunol. May 1996; 156(9):3285-91.
Paul, Fundamental Immunology, $3^{rd}$ Edition, 1993, pp. 292-295.
Abbas et al. Cellular and Molecular Immunology $4^{th}$ edition, 2000 Chapter 48 p. 42-43 and p. 48.
Goel et al. J Immunol, 2004, 173 (12) 7358-7367.
Torres et al. Trends in Immunology vol. 29, No. 2, p. 91-97, 2008.
Ferrara et al. mAbs, 7:1, 32-41, 2015.
Edwards et al (J. Mol. Biol. (2003) 334, 103-118.

* cited by examiner

| Name | Framework H | Framework L |
|---|---|---|
| hPRR13-1 | wt | wt |
| hPRR13-2 | H73 (T=>K) | wt |
| hPRR13-3 | H76 (G=>S) | wt |
| hPRR13-4 | H73 + H76 | wt |
| hPRR13-5 | wt | L47 (L=>W) |
| hPRR13-6 | H73 (T=>K) | L47 (L=>W) |
| hPRR13-7 | H76 (G=>S) | L47 (L=>W) |
| hPRR13-8 | H73 + H76 | L47 (L=>W) |
| hPRR13-9 | wt | L70 (D=>S) |
| hPRR13-10 | H73 (T=>K) | L70 (D=>S) |
| hPRR13-11 | H76 (G=>S) | L70 (D=>S) |
| hPRR13-12 | H73 + H76 | L70 (D=>S) |
| hPRR13-13 | wt | L47 + L70 |
| hPRR13-14 | H73 (T=>K) | L47 + L70 |
| hPRR13-15 | H76 (G=>S) | L47 + L70 |
| hPRR13-16 | H73 + H76 | L47 + L70 |

| Name | Framework Mutation H | Framework Mutation L |
|---|---|---|
| hC6-17-1 | wt | wt |
| hC6-17-2 | wt | L87 (Y=>S) |
| hC6-17-3 | H71 (R=>V) | wt |
| hC6-17-4 | H71 (R=>V) | L87 (Y=>S) |
| hC6-17-5 | H73 (T=>R) | wt |
| hC6-17-6 | H73 (T=>R) | L87 (Y=>S) |
| hC6-17-7 | H76 (=>R-S) | wt |
| hC6-17-8 | H76 (=>R-S) | L87 (Y=>S) |
| hC6-17-9 | H71 + H73 | wt |
| hC6-17-10 | H71 + H73 | L87 (Y=>S) |
| hC6-17-11 | H71 + H76 | wt |
| hC6-17-12 | H71 + H76 | L87 (Y=>S) |
| hC6-17-13 | H73 + H76 | wt |
| hC6-17-14 | H73 + H76 | L87 (Y=>S) |
| hC6-17-15 | H71 + H73 + H76 | wt |
| hC6-17-16 | H71 + H73 + H76 | L87 (Y=>S) |

Figure 22

SUBSTANCES AND METHODS FOR THE USE IN PREVENTION AND/OR TREATMENT IN HUNTINGON'S DISEASE

This application is a divisional of U.S. application Ser. No. 16/996,031 filed Aug. 18, 2020, abandoned pending, which is a continuation of U.S. application Ser. No. 16/025,095 filed Jul. 2, 2018, abandoned, which is a continuation of U.S. application Ser. No. 15/323,461 filed Jan. 3, 2017, now U.S. Pat. No. 10,053,518 and incorporated herein by reference, which is a National Stage of PCT/EP2015/065795 filed Jul. 10, 2015 and claims the benefit of EP 14176609.7 filed Jul. 10, 2014.

The present invention relates to providing substances and methods for use in the treatment and prevention of Huntington's disease.

Huntington's disease is a rare monogenetic disorder with an autosomal dominant mode of inheritance. It is caused by a CAG trinucleotide repeat expansion within the coding region of the Huntingtin (HTT) gene on human chromosome 4 (Novak & Tabrizi, 2011). The causative CAG repeat expansion is associated with genetic instability during replication and changes in RNA splicing. Most importantly however, the encoded protein is changed in structure due to an expanded polyglutamine (polyQ) tract in the N-terminal portion of the protein leading to accumulation of structurally changed and modified Huntingtin protein and protein fragments in the brain and other organs or cells over time. This process resembles other neurodegenerative proteinopathies such as e.g. Alzheimer's- or Parkinson's disease or Multiple System Atrophy where the common denominator is the formation of aggregates or protein fibrils combined with protein degradation products. In Huntington's disease, the pathological hallmark is progressive neurodegeneration mainly of the striatum and cortex with accumulation of aggregated and degraded Huntingtin protein.

The clinical symptoms of Huntington's disease progress in a predictable manner starting subtly with mood changes or cognition problems followed by unsteady gait and motoric problems. With time, physical abilities deteriorate with manifest movement coordination problems combined with a decline in mental abilities and psychiatric and behavioral problems. Average life expectancy is around twenty years after first clinical manifestation. Symptoms can vary significantly and it has been well documented that the age of onset inversely correlates with the number of CAG repeats in the mutant Huntingtin gene corroborating the causative role of mutated Huntingtin.

There is no cure or prevention for Huntington's disease. To control the symptoms, full-time patient care is required in the later stages of the disease and the burden for the patient and his social environment is substantial. Symptomatic treatments such as pharmaceutical and non-drug treatments can relieve some of the symptoms.

With the current understanding of Huntington's disease etiology and genetic cause, mutant Huntingtin is regarded as prime target for disease modifying targeting strategies although not in the conventional way (Yu et al., 2014). Based on clinical genetics and functional evidence from animal models (Bard et al., 2014), Huntingtin lowering strategies are regarded as approaches of paramount importance despite molecular challenges associated with such a concept (Zheng & Diamond, 2012). Current strategies are typically hampered by the lack of delivery of the therapeutic agent to the targeting site within affected neurons in the brain. This counts for DNA or mRNA targeting approaches currently under development (Davidson, 2012). An alternative approach consists of using intrabodies provided by viral vectors targeting intracellular Huntingtin in the brain (Butler et al., 2012). Despite their proven functionality in preclinical models, these approaches are facing major delivery challenges to the targeting site. In addition, "foreign" structures e.g. such as scFv-based intrabodies (Messer & Joshi, 2013) carry the risk of potentially constituting new epitopes to the host thereby inducing undesired humoral immune responses against the therapeutic agent or T-cell responses against the cells expressing and presenting "foreign" protein.

WO 2012/140376 A1 discloses therapeutic peptides pep4 and pep42, both peptides do not extend to the c6 cleavage site of HTT. WO 2010/015592 A2 discloses assays for mutated polyQ protein. Ko et al. (Brain Res. Bull. 56 (2001): 319-329) disclose anti-HTT monoclonal antibodies, most binding to the polyQ domain of HTT. Persichetti et al. (Mol. Med. 1 (1995): 374-383) disclose antibody-eliciting peptides HP1 and HP12.

US 2007/0026029 A1 (U.S. Pat. No. 7,935,252) discloses an apheresis device to treat and prevent Alzheimer's disease. Weiss et al. (Anal. Biochem. 395(2009): 8-15) disclose detection methods for mutant HTT in animal and human tissue. Butler et al. (Prog. Neurobiol. 97(2011): 190-204) disclose antibody therapies for HD patients. US 2010/0233180 A1 discloses antibodies that bind to a polyP region of HTT. Chen et al. (Chem. Biol. 18(2011): 1113-1125) suggest an expanded polyQ peptoid for HD treatment.

In order to provide an alternative treatment approach for Huntington's disease, an apheresis device comprising antibodies that are capable of targeting Huntingtin are provided by the present invention. In Huntington's disease, there is increasing awareness that the condition is accompanied by generalized changes including the immune system, peripheral tissues, peripheral blood lymphocytes (PBL) and metabolism, underlining the systemic nature of this disease. As an example, pathological Huntingtin accumulation is not solely restricted to the CNS but can also be detected in peripheral blood cells (Weiss et al., 2012). By lowering Huntingtin expression in primary human macrophages/monocytes, disturbance of the innate immune system could be partially reversed by Huntingtin-targeted RNA interference (Träger et al. 2014).

Beside detection of Huntingtin within blood cells, soluble Huntingtin or Huntingtin fragments were serendipitously detected in the human plasma proteome of healthy donors (Liu et al 2007) or detected by ELISA in plasma of Glaucoma patients so far not related to Huntington's disease (Tezel et al 2012). Although the important role of the immune system in Huntington's disease has been recognized (Ellrichmann et al., 2013), a possible causative role for extracellular Huntingtin has been largely neglected. More recently, plasma and CSF Huntingtin, was merely suggested as potential biomarker for monitoring disease progression (Weiss et al., 2014). Targeting possibly pathogenic, disease promoting extracellular Huntingtin protein was not previously considered as a therapeutic target nor was it shown whether performing apheresis using e.g. Huntingtin antibodies could provide a therapeutic benefit.

It is an object of the present invention to provide new therapeutic strategies for Huntington's disease, especially strategies that are beyond the mere control of symptoms. It is another object to provide means for preventing or delaying the onset of symptoms associated with Huntington's disease.

Therefore the present invention provides an apheresis device for capturing HTT for the treatment of Huntington's disease or delaying the onset of its clinical symptoms.

Huntingtin-apheresis according to the present invention is a completely new approach in the treatment of Huntington's disease and is shown to be highly effective by the present invention. The present apheresis device uses HTT binding molecules (i.e. molecules ("receptors") that specifically bind HTT and/or HTT fragments that are contained in blood plasma (whole blood, blood serum or other blood derivates; in the following, all references to "blood plasma" are usually also applicable to any other body fluids, especially those that are derived from blood, such as blood serum)) or other body fluids (potentially containing HTT or HTT fragments, such as CSF) of patients of Huntington's disease). "Capturing HTT" or "binding HTT" according to the present invention therefore also includes the capturing of HTT fragments that are derived from HTT (and are physiologically and/or pathologically relevant) that can be captured or bound e.g. from the blood or plasma flow conducted extracorporally to the apheresis device. Preferred HTT fragments are those HTT fragment peptides that are derived from structurally exposed/accessible domains of plasma HTT such as the protease cleavage sites disclosed herein or comparable enzymatic substrate sites of HTT. All such HTT fragments are also well suited for mAb generation in order to generate HTT-apheresis adsorbers ("HTT binding molecules"; "HTT-binding receptor") according to the present invention.

"Capturing HTT" or "binding HTT" according to the present invention further includes binding HTT (or its fragments) in a form associated to other molecules.

"HTT binding molecule" according to the present invention can be any molecule specifically binding to HTT (or a naturally occurring and pathologically relevant fragment thereof). A specifically preferred group of HTT binding molecules are binding molecules that are based on anti-HTT antibodies, preferably monoclonal or polyclonal anti-HTT antibodies, which may be easily immobilised on a solid surface. Especially preferred are HTT binding fragments or derivates of such antibodies, for example Fab, Fd, Fab', F(ab')2, Fv, or ScFv fragments. HTT binding molecules may also be selected by their efficiency with respect to providability, eg. based on production efficacy, folding efficiency, stability, protease resistance, pH resistance, affinity or immobilisation capability.

Preferred HTT binding molecules according to the present invention (also referred to as "apheresis adsorber") have high affinity and specificity for HTT (and its fragments), are stable and protease resistant to prevent shedding of proteolytic fragments into the blood stream (if shedding is a concern for specific apheresis architectures, human or humanized antibodies (or derivatives thereof) are preferred, since shedded human/humanised antibody fragments are less immunogenic than mouse fragments; usually, however, this is not a major issue since in general "unstable" adsorber molecules that are prone to proteolysis when it comes into contact with plasma are usually excluded). Since high amounts of HTT binding molecules are needed, recombinant protein production of such HTT binding molecules is the first choice (rather than purification from sera etc.). This is cost effective and it implies that the protein is small and robust with respect to correct folding and timely high yield production in mammalian cells, yeast, bacteria or plant protein production systems.

Since proper use of apheresis devices may also require recycling (desorbtion) that may be conducted by pH shock, preferred adsorbers should be pH resistant, i.e. the HTT binding molecule should refold correctly so that its affinity and specificity is not hampered.

Preferred HTT binding molecules should also be immobilized effectively on the matrix support, preferably by covalent, oriented/directed immobilization (especially by one defined reactive group on the molecule (cysteine, primary amine, artificially introduced aldehydes etc. —see e.g. the review by van Vught R et al. Comput Struct Biotechnol J. 2014; PMID: 24757499)) which is applicable to any recombinant protein such as a recombinant mAB or preferentially a smaller entity such as a Fab or scFv, etc.

The (extracorporal) blood or plasma flow (optionally containing HTT to be removed from the blood of a patient having Huntington's disease) is conducted over this solid surface to specifically remove HTT by binding HTT to the HTT binding molecules on the solid surface of the apheresis device according to the present invention. In particular antibodies that target particularly immunogenic epitopes of HTT such as the polyproline-rich region or other structurally exposed sites such as e.g. the region around a previously described protease cleavage site at amino acid position 586 of the Huntingtin protein may be used in the apheresis device according to the present invention. In the following, this etiologically/functionally important cleavage region will be referred to as "caspase region 586". Graham et al., 2006 have shown that preventing caspase 6 cleavage by genetic means inhibited the phenotype in mice carrying a mutant human Huntingtin transgene. Wong et al. (Wong 2014) provided evidence that other proteases can also access this region With the present invention it is the first time proposed to target plasma Huntingtin by apheresis to combat Huntington's disease. So far, (extracellular) plasma HTT has not been considered as target for treating this disease. Moreover, mode of action mechanisms are plausibly provided by the present invention (yet, without limiting the invention to such mechanisms) by in vitro phagocytosis assay and by in vivo lowering of HTT levels in apheresis-treated animals and phenotypic effects in animal models providing convincing P.O.C. (proof of concept) showing that plasma HTT targeting is also beneficial in human patients.

Moreover, HTT-derived peptides that provide antibodies to be used in the apheresis device according to the present invention are provided with the present invention. In the course of the present invention, core epitopes of the most relevant peptides for providing such antibodies are defined. Peptides derived from the caspase region of HTT are provided that are used for providing and inducing antibodies (AB's) that specifically bind to HTT. These peptides were used to generate various monoclonal antibodies (mABs) that are also useful in diagnosis and therapy of Huntington's disease by therapeutic apheresis (alone or in combination with vaccination), as a tool for HTT level determination in biomarker evaluation/discovery and as tool for (companion-) diagnostics, etc.

"Huntingtin", "Huntingtin protein" or "HTT" as used herein refers to the expression product of the Huntingtin gene. The protein details are available (and relied upon herein) under P42858 (HD_HUMAN) in the UniProtKB/Swiss-Prot database (Version 148, last modified 14 May 2014). Due to variations in the polyQ region starting at amino acid position 18 of HTT, the caspase cleavage site is referred to in the UniProt database entry as between amino acid 584 and 585. In the scientific literature and also herein, the caspase cleavage site is referred to as being between amino acid residues 586 and 587 (i.e. after "VLD" and before "GTD", i.e. between D and G). Accordingly, the "C6 cleavage region" or "C6 cleavage region 586" according to the present invention corresponds to amino acid 584 in the P42858 (HD_HUMAN) UniProtKB/Swiss-Prot database entry.

For example, the antibodies used in the apheresis device according to the present invention may target a second, functionally defined region of Huntingtin, called the PRR domain (standing for Proline-Rich Region). This region has previously been shown to be implicated in intracellular protein interactions such as e.g. with PACSIN1 (Modregger et al., 2002) and evaluated as a potential intrabody targeting region using single chain Fv fragments (Southwell et al., 2011).

In an embodiment of the invention, antibodies provided with the invention can be used in plasma apheresis to reduce plasma levels of Huntingtin, a strategy, which has not been proposed previously since a pathogenetic role for Huntingtin in the plasma has not previously been recognized, e.g. as shown in Example 6.

The present invention discloses peptides derived from the PRR and the c6 region. The peptides according to the present invention have a significant beneficial technical relationship which is reflected by several common features: (1) All PRR- and C6-derived peptides according to the present invention share particular immunogenicity; their epitopes are particularly accessible (in contrast to e.g. peptides from the very N-terminus or the polyQ region as shown in example 1); in particular, targeting their epitopes is highly relevant for achieving a therapeutic effect as shown in the functional in vivo examples in the example section below. (2) The peptides according to the present invention are mapping to regions of HTT for which structural/functional relevance such as protease accessibility or protein-protein interaction has been demonstrated. (3) Most importantly, the combinatorial targeting of these two epitopes provides efficient therapeutic effect (in contrast to using one single epitope).

In this connection, it has to be noted that not any HTT derived peptide can be used for the treatment of HTT. This is also shown in the example section below. In fact, certain peptides are more immunogenic than others. Moreover, the combination of certain peptides shows stronger effectivity (for example the combination of PRR- and C6-region peptides with respect to HTT plasma clearance ad motoric effects). The present invention also provides advantageous combinations of peptides for the treatment of HTT. As already mentioned, with the present invention, therapeutic vaccines are provided which target (as the therapeutic principle) extracellular HTT. This alone is already a completely novel strategy, since HTT has always been known as intracellularly aggregating protein.

The peptides according to the present invention and the present vaccine targeting regions were defined (1) according to the accessibility and (2) immunogenicity of the regions/peptides. In addition, certain combinations of peptides (as shown in the in vivo examples below) provide enhanced HTT clearance and phenotypic (motoric and histologic) changes. These changes can be explained by Fc receptor-mediated clearance mechanisms (phagocytosis) as also shown in the examples. Fc-receptor mediated phagocytosis requires polyvalency of antigen-antibody complexes explaining the higher effectivity of targeting HTT on two or more rather than one single epitope: An antigen/antibody complex presenting multiple Fc portions is more likely to be cleared by phagocytosis than a single HTT molecule bound by one single antibody.

This was neither disclosed nor suggested by the prior art. For example, the therapeutic peptides pep4 and pep42 disclosed in WO 2012/140376 A1 or the peptides derived from the N-terminus of HTT reported by Miller et al. (2003) are derived from different regions of HTT than the peptides according to the present invention. Even more important, these peptides described e.g. in WO 2012/140376 A1 were never intended or used for any therapeutic purpose such as e.g. vaccines (i.e. for the induction of B-cell immune responses in a living organism). Instead, WO 2012/140376 A1 discloses peptides that can be used for aggregation inhibition (i.e. by direct interference with HTT or its fragments), which does not relate to inducing immune responses such as needed for a vaccine. The antibodies in WO 2010/015592 A2 were generated as probes for the detection of HTT (or its aggregates or fragments) by a FRET assay or other in vitro analytical means. The purpose for providing these antibodies was—again—experimental/analytical or diagnostic but not therapeutic. In general, it has never previously been proposed nor demonstrated that anti HTT antibodies could be used for therapeutic purposes for the treatment of Huntington's disease. Moreover, not any of the antibodies from WO 2010/015592 A2 has an overlap with the vaccination peptides according to the present invention. Finally, peptides "HP1" and "HP12" cited in Persichetti et al. (1995) were used for the generation of polyclonal antisera in order to provide analytical probes for HTT detection under experimental conditions (e.g. such as HTT detection by Western Blot or IHC) but not for the use in vaccine therapy. The same counts for monoclonal antibodies such as e.g. described in Ko et al. (2001) (e.g. HW1-8) that were generated by a polyQ-HTT-GST fusion protein but not by peptide immunization.

It is therefore important to note that the peptides according to the present invention are suitable for the generation of therapeutic vaccines, whereas the prior art peptides for generating polyclonal or monoclonal antibodies were designed to provide probes for analytical or diagnostic use.

Accordingly, the peptides according to the present invention derived from the PRR and the C6 region are specifically advantageous. Both groups are highly immunogenic, especially SEQ ID Nos. 1, 4, 16, 19 and 28; and 2, 3, 6-18 and 20-50; with SEQ ID Nos. 1-4 being highly preferred due to their functional performance in the in vivo experiments.

The immunogenic peptides of the HTT protein for providing the antibodies used in the apheresis device according to the present invention, comprise p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p7543a (DNQYLGLQIC; SEQ ID No. 88), especially the derivatives p9394 (KTDNQYLGLQIGKC; SEQ ID No. 91), p9395 (GTDNQYLGLQIGXKC; SEQ ID No. 92), p9396 (KTDNQYLGLQIKKGC; SEQ ID No. 93), p9397 (KDNQYLGLQIKKGC; SEQ ID No. 94); p7543b (TDNQYLGLQIC; SEQ ID No. 89), p7543c (TDNQYLGLQIGC; SEQ ID No. 90), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), and p8346 (CGPAVAEEPLHRP, SEQ ID No. 5). The "C" residue in these sequences is always used (and has been introduced) as a linker; this cysteine linker at the N- or C-terminus can (as any other linker, such as -GC, -GGC, -KC, -KCC, -KCC, -KKC, -KKG, -KCG, -KGC, -KKGC (SEQ ID No. 99), -KKCG (SEQ ID No. 100) (and the N-terminal variants thereof, such as CG-, CGG-, etc.) or similar combinations of cysteine with amino acids such as e.g. beta-alanine or lysine as a spacer as e.g. used in peptides p6775, p6768, p9394, p9395, p9396 or p9397 respectively, or as other chemical moieties that provide linker or spacer function or improved peptide solubility without impeding immunological properties) be present or not or provided alternatively at C- or N-terminus of the peptide (i.e. at the alternative end of the peptide chain). Such combinations of linker peptides with solubility improvers are provided e.g. in the lysine derivatives p9394-p9397. In other embodiments, a linker can also be provided in at other amino acid positions than the N- or C-terminus, e.g. at an amino acid with a functional group, such as serine, lysine, arginine, tyrosine, threonine, aspartic or glutanic acid, asparagine or glutamine, histidine, methionine, etc. (especially the derivatives p9394 (KTDNQYLGLQIGKC; SEQ ID No. 91), p9395 (GTDNQYLGLQIGKKC; SEQ ID No. 92), p9396 (KTDNQYLGLQIKKGC; SEQ ID No. 93), p9397 (KDNQYLGLQIKKGC; SEQ ID No. 94)); however, in such embodiments, care must be taken that the immunological properties of the peptides are not severely impeded by such linking.

Further antibody eliciting immunogenic peptides are selected from the group consisting of p8855 (SDSSEIVLDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ ID No. 11), p8869 (CTDNQYLGLQIGQ, SEQ ID No. 12), p8868 (CGTDNQYLGLQIG, SEQ ID No. 13), p8870 (CDNQYLGLQIGQP, SEQ ID No. 14), p8871 (CNQYLGLQIGQPQ, SEQ ID No. 15), p6772 (CPQLPQPPPQAQPLLP, SEQ ID No. 16), p8864 (TDNQYLGLQIGQC, SEQ ID No. 17), p8865 (DNQYLGLQIGQPC, SEQ ID No. 18), p6775 (PPPQLPQPPPQAQPLLPQPQPaC, SEQ ID No. 19), p8854 (PSDSSEIVLDGTC, SEQ ID No. 20), p8856 (DSSEIVLDGTDNC, SEQ ID No. 21), p8857 (SEIVLDGTDNQYC, SEQ ID No. 22), p8866 (NQYLGLQIGQPQC, SEQ ID No. 23), and p8867 (QYLGLQIGQPQDC, SEQ ID No. 24), wherein the N- or 2-terminal cysteine residue (C) may be present or not or provided alternatively at the C- or N-terminus.

Other suitable antibody eliciting immunogenic peptides are selected from the group consisting of p6763 (CaMATLEKLMKAFESLKSFQ, SEQ ID No. 25), p6764 (CaKLMKAFESLKSFQ, SEQ ID No. 26), p6765 (CEEQQRQQQQQQQ, SEQ ID No. 27), p6768 (QQQQQQPPPPPPPPaKKKC, SEQ ID No. 28), p7541 (CSEIVLD, SEQ ID No. 29), p7552 (CSSEIVLD, SEQ ID No. 30), p7562 (CDSSEIVLD, SEQ ID No. 31), p7563 (CSDSSEIVLD, SEQ ID No. 32), p7567 (CEIVLD, SEQ ID No. 33), p7568 (CIVLD, SEQ ID No. 34), p2605 (CSEIVL, SEQ ID No. 35), p6776 (CSEIVLDGTDNQYL, SEQ ID No. 36), p6777 (CSDSSEIVLDGTDN, SEQ ID No. 37), p6776b (SEIVLDGTDNQYLC, SEQ ID No. 38), p7752 (CAEIVLDGTDNQYL, SEQ ID No. 39), p7753 (CSAIVLDGTDNQYL, SEQ ID No. 40), p7754 (CSEAVLDGTDNQYL, SEQ ID No. 41), p7755 (CSEIALDGTDNQYL, SEQ ID No. 42), p7756 (CSEIVADGTDNQYL, SEQ ID No. 43), p7757 (CSEIVLAGTDNQYL, SEQ ID No. 44), p7758 (CSEIVLDATDNQYL, SEQ ID No. 45), p7745 (CSEIVLDGADNQYL, SEQ ID No. 46), p7746 (CSEVLDGTANQYL, SEQ ID No. 47), p7747 (CSEIVLDGTDAQYL, SEQ ID No. 48), p7748 (CSEIVLDGTDNAYL, SEQ ID No. 49), p7749 (CSEIVLDGTDNQAL, SEQ ID No. 50), and p7750 (CSEIVLDGTDNQYA, SEQ ID No. 51), wherein the N- or C-terminal cysteine residue (C) may be present or not or provided alternatively at the C- or N-terminus.

According to the present invention, immunogenicity is the ability of a particular substance, such as an antigen or an epitope, to elicit antibodies to the given peptide.

Preferably, these peptides are at least 7 amino acids long, and preferred lengths may be up to 16, preferably up to 14 or 20 amino acids residues (e.g. 7 or 8 to 20, 7 or 8 to 16 etc.). The "C" at the N- or the C-terminus of the peptides of SEQ ID NOs 1 to 51 has been provided as a linker which may or may not be present or replaced by another amino acid or chemical linker allowing for immobilization to a carrier. Further linking amino acids may be provided at this end of the peptide, either immediately before the "C" (cysteine residue) or immediately after the "C". The "C" may also be omitted, if it is not needed for coupling and/or if immunogenicity is safeguarded by other means than "C"-binding to a carrier. Alternatively, also fragments of these peptides may be used according to the present invention, preferably with a minimum length of 7 amino acid residues, wherein one or more amino acids before the cysteine residue are omitted. Alternatively, polar or charged amino acids not affecting immunogenicity and specificity of the immunogenic peptide can be used to increase peptide solubility. Thus, the peptide used to provide antibodies for the apheresis device of the present invention comprises 7 to 30, preferably 7 to 20, more preferably 7 to 16, most preferably 8, amino acid residues. However, also longer peptides may very well be employed as anti-HTT-antibody-inducing antigens, e.g. as shown in Example 1.

Prevention of Huntington's disease according to the present invention is defined as preventing or delaying the outbreak and/or onset of Huntington's disease associated symptoms such as motoric and psychiatric symptoms or immunologic and metabolic changes in individuals with a propensity to develop Huntington's disease symptoms based on their elevated number of GAG repeats in at least one HTT allele.

Treatment of Huntington's disease according to the present invention is defined as ameliorating Huntington's disease associated motoric symptoms such as chorea and psychiatric, or immunologic and metabolic changes in individuals, which were genetically identified to carry the mutated HTT (i.e. individuals who carry more than 26 GAG repeats in at least one HTT allele) and have been diagnosed positive for Huntington's disease based on their symptoms and genotype such as shown by inducing phenotypic changes in animal models for Huntington's disease, e.g. as in Example 2 and 3.

The antibodies to be used in the apheresis device according to the present invention may be provided from a polyclonal antibody serum specifically recognising at least one peptide of the HTT protein as disclosed herein.

The antibodies to be used in the apheresis device according to the present invention may be purified e.g. from antibody serum or hybridoma supernatant according to techniques known to a person skilled in the art, such as affinity chromatography. The antibodies to be used in the present apheresis device according to the present invention may also be obtained by overexpression of the corresponding cDNA in suitable protein expression vectors known to a person skilled in the art using mammalian cell expression systems or baculovirus-, yeast-, plant- or bacterial expression systems or alternatively using coupled in vitro transcription/translation systems to gain control over in vitro production conditions.

For example, the polyclonal antibody serum comprised in said pharmacological composition is raised against at least one peptide selected from the group consisting of p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p7543a (DNQYLGLQIC; SEQ ID No. 88), especially the derivatives p9394 (KTDNQYLGLQIGKC; SEQ ID No. 91), p9395 (GTDNQYLGLQIGKKC; SEQ ID No. 92), p9396 (KTDNQYLGLQIYKGC; SEQ ID No. 93), p3397 (KDNOYLGLQIKKGC; SEQ ID No. 94); p7543b (TDNOYLGLQIC; SEQ ID No. 89), p7543c (TDNQYLTGQIGC; SEQ ID No. 90), p6771 (LPQPPPQAQPLLPC, SEQ ID No. 4), p8346 (CGPAVAEEPLHRP, SEQ ID No. 5), p8855 (SDSSEIVLDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ II) No. 11), p8869 (CTDNQYLGLQIGQ, SEQ ID No. 12), p8868 (CGTDNQYLGLQIG, SEQ ID No. 13), p8870 (CDNQYLGLQIGQP, SEQ ID No. 14), p8871 (CNQYLGLQIGQPQ, SEQ ID No. 15), p6772 (CPQLPOPPIPQAQPLLP, SEQ ID No. 16), p8864 (TDNQYLGLQIGQC, SEQ ID No. 17), p8865 (DNQYLGLQIGQPC, SEQ ID No. 18), p6775 (PPPQLPQPPPQAQPLLPQPQPaC, SEQ ID No. 19), p8854 (PSDSSEIVLDGTC, SEQ ID No. 20), p8856 (DSSEIVLDGTDNC, SEQ ID No. 21), p8857 (SEIVLDGTDNQYC, SEQ ID No. 22), p8866 (NQYLGLQIGQPQC, SEQ ID No. 23), p8867 (QYLGLQIGQPQDC, SEQ ID No. 24), p6763 (CaMATLEKLMKAFESLKSFQ, SEQ ID No. 25), p6764 (CaKLMKAFESLKSFQ, SEQ ID No. 26), p6765 (CEEQQRQQQQQQQ, SEQ ID No. 27), p6768 (QQQQQQPPPPPPPaKKKC, SEQ ID No. 28), p7541 (CSEIVLD, SEQ ID No. 29), p7552 (CSSEIVLD, SEQ ID No. 30), p7562 (CDSSEIVLD, SEQ ID No. 31), p7563 (CSDSSEIVLD, SEQ ID No. 32), p7567 (CEIVLD, SEQ ID No. 33), p7568 (CIVLD, SEQ ID No. 34), p7605 (CSEIVL, SEQ ID No. 35), p6776 (CSEIVLDGTDNQYL, SEQ ID No. 36), p6777 (CSDSSEIVLDGTDN, SEQ ID No. 37), p6776b (SEIVLDGTDNQYLC, SEQ ID No. 38), p7752 (CAEIVLDGTDNQYL, SEQ ID No. 39), p7753 (CSAIVLDGTDNQYL, SEQ ID No. 40), p7754 (CSEAVILDGTDNQYL, SEQ ID No. 41), p7755 (CSEIALDGTDNQYL, SEQ ID No. 42), p7756 (CSEIVADGTDNQYL, SEQ ID No. 43), p7757 (CSEIVLAGTDNQYL, SEQ ID No. 44), p7758 (CSEIVLDATDNQYL, SEQ ID No. 45), p7745 (CSEIVLDGADNQYL, SEQ ID No. 46), p7746 (CSEIVLDGTANQYL, SEQ ID No. 47), p7747 (CSEIVLDGTDAQYL, SEQ ID No. 48), p7748 (CSEIVLDGTDNAYL, SEQ ID No. 49), p7749 (CSEIVLDGTDNQAL, SEQ ID No. 50), and p7750 (CSEIVLDGTDNQYA, SEQ ID No. 51), preferably p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), p8346 (CGPAVAEEPLHRP, SEQ ID No. 5), p8855 (SDSSEIVLDGTDC, SEQ ID No. 6), p8858 (EIVLDGTDNQYLC, SEQ ID No. 7), p8859 (IVLDGTDNQYLGC, SEQ ID No. 8), p8860 (VLDGTDNQYLGLC, SEQ ID No. 9), p8861 (LDGTDNQYLGLQC, SEQ ID No. 10), p8862 (DGTDNQYLGLQIGC, SEQ ID No. 11), p8869 (CTDNQYLGLQIGQ, SEQ ID No. 12), p8868 (CGTDNQYLGLQIG, SEQ ID No. 13), p8870 (CDNQYLGLQIGQP, SEQ ID No. 14), p8871 (CNQYLGLQIGQPQ, SEQ ID No. 15), p6772 (CPQLPQPPPQAQPLLP, SEQ ID No. 16), p8864 (TDNQYLGLQIGQC, SEQ ID No. 17), p8865 (DNQYLGLQIGQPC, SEQ ID No. 18), p6775 (PPPQLPQPPPQAQPLLPQPQPaC, SEQ ID No. 19), p8854 (PSDSSEIVLDGTC, SEQ ID No. 20), p8856 (DSSEIVLDGTDNC, SEQ ID No. 21), p8857 (SEIVLDGTDNQYC, SEQ ID No. 22), p8866 (NQYLGLQIGQPQC, SEQ ID No. 23), and p8867 (QYLGLQIGQPQDC, SEQ ID No. 24), especially p6773 (LPQPPPQAQPLLPQPQPC, SEQ ID No. 1), p7564 (CPSDSSEIVLD, SEQ ID No. 2), p7543 (GTDNQYLGLQIGC, SEQ ID No. 3), p6771 (LPQPPPQAQPLLPC, SEQ ID No. 4), p6776 (CSEIVLDGTDNQYL, SEQ ID No. 36), p6777 (CSDSSEIVLDGTDN, SEQ ID No. 37), and p8346 (CGPAVAEEPLHRP, SEQ ID No. 5).

The polyclonal antibody serum from which the apheresis antibodies can be obtained are raised against at least one peptide of p6773 (SEQ ID No. 1) and p6771 (SEQ ID No. 4). Alternatively or in combination, the polyclonal antibody serum may be raised against peptide p7543 (SEQ ID No. 3).

Alternatively or in combination, the polyclonal antibody serum may be raised against pep ide p7564 (SEQ ID No. 2).

Alternatively or in combination, the polyclonal antibody serum may be raised against peptide p6776 (SEQ ID No. 36).

According to another aspect, the present invention relates to an apheresis device comprising monoclonal antibodies against HTT or naturally occurring fragments thereof. The monoclonal (as well as the polyclonal) antibodies according to the present invention are immobilised on the surface of an apheresis device to be contacted to the blood or plasma flow of a patient having Huntington's disease as "isolated antibodies". An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). Such purity is usually needed to safeguard the prerequisites of quality control for apheresis devices. For a monoclonal antibody, also the nucleic acid encoding the antibody is available. Such nucleic acid molecules encoding antibody heavy and light chains (or fragments thereof), including such nucleic acid molecule(s) in a single vector or separate vectors, and such nucleic acid molecule(s) present at one or more locations in a host cell may be used to produce the antibodies for the apheresis device according to the present invention.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-, yeast- or mammalian cell-display methods, and methods utilizing transgenic animals containing all or part of the human immunoglobulin loci, such methods and other exemplary methods for making monoclonal antibodies being described herein.

The present invention also provides a monoclonal antibody "PRR13" for use in the present apheresis device having a binding domain capable of binding to an epitope of the HTT protein having the sequence "LLPQP" (SEQ ID No. 78) contained within peptide p6773 (SEQ ID No. 1), especially to the core epitope LLPQP (SEQ ID No. 78). With the present invention, mABs against this minimal core epitope that has been provided with the experiments according to the present invention are provided, i.e. against the core epitope LLPQP (SEQ ID No. 78). In a preferred embodiment, said monoclonal antibody is characterised as being the monoclonal antibody PRR13, which comprises a heavy chain variable region CDR1 comprising the peptide sequence GYSFTDFY (SEQ ID No. 54), a heavy chain variable region CDR2 comprising IDPKNGDT (SEQ ID No. 55), a heavy chain variable region CDR3 comprising ATYYGYTMDY (SEQ ID No. 56), a light chain variable region CDR comprising SSVTSSY (SEQ ID No. 57), a light chain variable region CDR2 comprising STS (SEQ ID No. 58) and a light chain variable region comprising HQYRRPPRT (SEQ ID No. 59), e.g. as shown in Example 5.

CDR are complementarity determining regions and represent variable regions of antibodies, with which the antibody binds to its specific epitope. The type and number of heavy chain determines the class of antibody, i.e. IgA, IgD, IgE, IgG and IgM antibodies, respectively. Antibodies contain also two identical light chains, which can be of lambda or kappa type.

According to the present invention the monoclonal antibodies for use in the present apheresis device are preferably engineered antibodies where CDRs of non-human antibodies were transferred into a human antibody framework and thereby adapted in sequence such that affinity and specificity of the original hybridoma-derived mouse antibody is at least maintained and T-cell and B-cell immunogenicity to humans of the newly engineered protein is minimized (humanized monoclonal antibodies). This is especially required if undesired, minimal amounts of adsorber protein is leaking into the blood of the patient (possibly due to the generation of cleavage fragments e.g. by proteolysis or other protein degradation processes affecting the immobilized adsorber protein). CDRs can also be transferred into other engineered formats such as bispecific or chimeric monoclonal antibodies, antibodies with enhanced stabilization functions. The antibodies for use in the present apheresis device are preferably human anti HTT antibodies.

Whereas human or humanised antibodies can have advantages in the present invention, also other HTT binding molecules, such as murine antibodies may be used in the apheresis device according to the present invention. A specifically preferred embodiment of the present invention employs more than a single type of HTT binding molecule, e.g. at least two anti-HTT antibodies (or HTT-binding antibody fragments) that bind to different regions of HTT. They may also be of different origin (e.g. a human or humanised antibody and a murine antibody). The HTT binding molecules may also be selected by their stability and immobilisation behaviour (e.g. their recyclability) or by their affinity and specificity. The affinity of such an antibody as defined by the equilibrium dissociation constant (Kr) preferably ranges between $10^{-7}$ to $10^{-9}$ i.e. in the nanomolar (nM) range providing a reasonably high on rate. In order to increase specificity and avidity, it is generally preferable to combine two or more antibodies. In analogy to the in vivo effects of vaccine treatments (see below), an avidity/combinatorial effect of two or more antibodies is preferred in order to achieve efficient clearance of the target protein from the plasma.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al, Sequences of Proteins of immunological Interest, 5th ed., Bethesda MD (1991), NIH Publication 91-3242, Vols. 1-3. In one embodiment, for the VL, the subgroup is subgroup kappa I as in Kabat et al, supra. In one embodiment, for the VH, the subgroup is subgroup III as in Kabat et al, supra.

A "humanized" antibody refers to a chimeric antibody comprising amino acid residues from non-human HVRs and amino acid residues from human FRs. "Framework" or "FR" refers to variable domain residues other than hypervariable region (HVR) residues. The FR of a variable domain generally consists of four FR domains: FR1, FR2, FF3, and FF4. Accordingly, the HVR and FR sequences generally appear in the following sequence in VH (or VL): FR1-H1 (L1)-FR2-H2 (L2)-FR3-H3 (L3)-FR4. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized variant" of an antibody, e.g., a non-human antibody, refers to an antibody that has undergone humanization. In one preferred embodiment, a murine HVR is grafted into the framework region of a human antibody to prepare the "humanized antibody". The murine variable region amino acid sequence is aligned to a collection of human germline antibody V-genes, and sorted according to sequence identity and homology. The acceptor sequence is selected based on high overall sequence homology and optionally also the presence of the right canonical residues already in the acceptor sequence. The germline V-gene encodes only the region up to the beginning of HVR3 for the heavy chain, and till the middle of HVR3 of the light chain. Therefore, the genes of the germline V-genes are not aligned over the whole V-domain. The humanized construct comprises the human frameworks 1 to 3, the murine HVRs, and the human framework 4 sequence derived from the human JK4, and the JH4 sequences for light and heavy chain, respectively. Before selecting one particular acceptor sequence, the so-called canonical loop structures of the donor antibody can be determined. These canonical loop structures are determined by the type of residues present at the so-called canonical positions. These positions lie (partially) outside of the HVR regions, and should be kept functionally equivalent in the final construct in order to retain the HVR conformation of the parental (donor) antibody. In WO 2004/006955 A1 a method for humanizing antibodies is reported that comprises the steps of identifying the canonical HVR structure types of the HVRs in a non-human mature antibody; obtaining a library of peptide sequence for human antibody variable regions; determining the canonical HVR structure types of the variable regions in the library; and selecting the human sequences in which the canonical HVR structure is the same as the non-human antibody canonical HVR structure type at corresponding locations within the non-human and human variable regions. Summarizing, the potential acceptor sequence is selected based on high overall homology and optionally in addition the presence of the right canonical residues already in the acceptor sequence. In some cases simple HVR grafting only result in partial retention of the binding specificity of the non-human antibody. It has been found that at least some specific non-human framework residues are required for reconstituting the binding specificity and have also to be grafted into the human framework, i.e. so called "back mutations" have to be made in addition to the introduction of the non-human HVRs (see e.g. Queen et al., PNAS 86 (1989), 10029-10033). These specific framework amino acid residues participate in FR-HVR interactions and stabilized the conformation (loop) of the HVRs. In some cases also forward-mutations are introduced in order to adopt more closely the human germline sequence. Thus "humanized variant of an antibody according to the invention" (which is e.g. of mouse origin) refers to an antibody, which is based on the mouse antibody sequences in which the VH and VL are humanized by above described standard techniques (including HVR grafting and optionally subsequent mutagenesis of certain amino acids in the framework region and the HVR-H1, HVR-H2, HVR-L1 or HVR-L2, whereas HVR-H3 and HVR-L3 remain unmodified).

In general, techniques for developing antibodies suitable for use in treatment of human patients from murine or other primarily selected mABs are well established (reviewed in Safdari et al 2013; PMID: 24568279). The antibodies disclosed herein may therefore be subjected to such development processes for providing improved antibodies by applying such validated techniques, especially CDR-grafting based methods (such as e.g. reviewed by Kim & Hong Methods Mol Biol. 2012; 907:237-45 [PMID: 22907355] or Whitelegg, N. & Rees, AR Antibody variable Regions: Towards a Unified modeling method. In: Methods in Molecular Biology, Biotechnology and Medicine, (Ed. Lo, B), 2004; 248:51-91) [PMID: 14970491], germline humanization or "super-humanization" (such as reviewed by Pelat, T. Et al., *Mini Rev Med Chem.* 2009 December; 9(14):1633-8) [PMID: 20105119] and resurfacing (such as described by Mader and Kunert et al., Prot. Eng. Des. Selec. 2010, 23, 947-954) [PMID: 21037278] or related methods that are based on these established techniques.

The term "hypervariable region," or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs are disclosed herein.

According to the present invention, also anti HTT antibodies that comprises a heavy chain variable domain (VH) sequence and/or light chain variable domain (VL) sequence having at least 90%, 91%, 92%, 93%, 94%, 95%, 96%, 97%), 98%), 99%), or 100% sequence identity to the amino acid sequence of SEQ ID NOs: 60 to 65 may be used in the present apheresis device. In certain embodiments, a VH sequence having at least 90%>, 91%>, 92%, 93%, 94%, 95%, 96%, 97%, 98%, or 99% identity contains substitutions (e.g. conservative substitutions), insertions, or deletions relative to the reference sequence, but an anti HTT antibody comprising that sequence retains the ability to bind to HTT, especially the epitope given. In certain embodiments, a total of 1 to 10 amino acids have been substituted, inserted and/or deleted in SEQ ID NOs: 60 to 65. In certain embodiments, substitutions, insertions, or deletions occur in regions outside the HVRs (i.e. in the FRs).

Preferred variants of the anti HTT antibodies according to the present invention are i.a. disclosed in FIG. 27 (i.e. variants hPRR13-2 to -16 and hC6-17-2 to -16). Accordingly, anti HTT antibodies with the amino acid exchanges in the H/L framework are specifically preferred according to the present invention. Moreover, all combinations of these variants are also specifically preferred. For example, for the heavy chain of the PRR antibody there are 1 wt+3 mutations, for the light chain there are also 1 wt+3 mutations. This provides a possible combination space of 4×4 variants as listed in the table of FIG. 27. For the mAB huC6-17, the following combinations are preferred: light chain: 1 wt+1 mut; heavy: 1 wt+7 mutations, making a total of 16 variants.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software or the "needle" pairwise sequence alignment application of the EMBOSS software package. Those skilled in the art can determine appropriate parameters for aligning sequences, including any algorithms needed to achieve maximal alignment over the full length of the sequences being compared. For purposes herein, however, % amino acid sequence identity values are calculated using the sequence alignment of the computer programme "needle" of the EMBOSS software package (publicly available from European Molecular Biology Laboratory; Rice et al., EMBOSS: the European Molecular Biology Open Software Suite, Trends Genet. 2000 June; 16(6):276-7, PMID: 10827456).

The needle programme can be accessed or downloaded for local installation as part of the EMBOSS package. It runs on many widely-used UNIX operating systems, such as Linux.

To align two protein sequences, the needle programme is preferably run with the following parameters:
Commandline: needle-auto-stdout-asequence SEQUENCE_FILE_A-bsequence SEQUENCE_FILE_B-datafile EBLOSUM62-gapopen 10.0-gapextend 0.5-endopen 10.0 -endextend 0.5-aformat3 pair-sprotein1-sprotein2 (Align_format: pair Report_file: stdout).

The % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the traction $X/Y$ where X is the number of amino acid residues scored as identical matches by the sequence alignment program needle in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, an antibody provided herein is a chimeric antibody. Certain chimeric antibodies are described, e.g., in U.S. Pat. No. 4,816,567 A; and Morrison et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity. Humanized antibodies and methods of making them are reviewed, e.g., in WO 2004/006955 A1 (approach via canonical structures).

In certain embodiments, an antibody provided herein is a human antibody. Human antibodies can be produced using various techniques known in the art. Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23 (2005) 1117-1125, U.S. Pat. Nos. 6,075,181 and 6,150,584 describing XENOMOUSE™ technology; U.S. Pat. No. 5,770,429 A describing HuMab® technology; U.S. Pat. No. 7,041,870 A describing K-M MOUSE® technology, and US 2007/0061900 A1, describing Veloci-Mouse® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. Human antibodies generated via human B-cell hybridoma technology are also described in Li et al, PNAS 103 (2006) 3557-3562. Additional methods include those described, for example, in U.S. Pat. No. 7,189,826 (describing production of monoclonal human IgM antibodies from hybridoma cell lines) or made by the Trioma technology. Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies to be used in the apheresis device according to the present invention may also be isolated by screening combinatorial libraries for antibodies with the desired activity or activities. For example, a variety of methods are known in the art for generating phage display libraries and screening such libraries for antibodies possessing the desired binding characteristics. Such methods are further described, e.g., in Fellouse, PNAS (2004) 12467-12472.

In certain phage display methods, repertoires of VH and VL genes are separately cloned by polymerase chain reaction (PCR) and recombined randomly in phage libraries, which can then be screened for antigen-binding phage. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization. Finally, naive libraries can also be made synthetically by cloning non-rearranged V-gene segments from stem cells, and using PCR primers containing random sequence to encode the highly variable CDR3 regions and to accomplish rearrangement in vitro. Further publications describing human antibody phage libraries include, for example: U.S. Pat. No. 5,750,373 A, US 2005/0079574 A1, US 2005/0119455 A1, US 2005/0266000 A1 (U.S. Pat. No. 7,785,903), US 2007/0117126 A1, US 2007/0160598 A1 (U.S. Pat. No. 8,679,490), US 2007/0237764 A1, US 2007/0292936 A1, and US 2009/0002360 A1 (U.S. Pat. No. 8,054,268). Antibodies or antibody fragments isolated from human antibody libraries are considered human antibodies or human antibody fragments herein.

In certain embodiments, an antibody to be used in the apheresis device herein is a multispecific antibody, e.g. a bispecific antibody. Multispecific antibodies are monoclonal antibodies that have binding specificities for at least two different sites. In certain embodiments, both of the binding specificities are for HTT helping to increase avidity and/or specificity to HTT protein or fragments thereof by simultaneously binding to more than one epitopes of the target. In certain embodiments bi- or multispecific antibodies are used to address more than one epitopes of HTT if separate plasma HTT protein fragments need to be adsorbed, each on ecarrying a distinct epitope. As an example, one epitope lies on one fragment whereas the other epitope(s) lie(s) on a physically distinct fragment of HTT. If both fragments need to be adsorbed from the plasma, it will be necessary to dispose over an adsorber targeting at least two epitopes, each one present on a separate fragment of the HTT protein. In certain embodiments, one of the binding specificities is for HTT and the other is for any other antigen that should also be extracted from the blood of a patient with Huntington's disease such as ex. an HTT-interacting protein present in the plasma in physical association with HTT or fragments thereof. Bispecific antibodies can be prepared as full length antibodies or antibody fragments. Techniques for making multispecific antibodies include, but are not limited to, recombinant co-expression of two immunoglobulin heavy chain-light chain pairs having different specificities (WO 93/08829 A, U.S. Pat. No. 5,731,168 A). Multi-specific antibodies may also be made by engineering electrostatic steering effects for making antibody Fc-heterodimeric molecules (WO 2009/089004 A); cross-linking two or more antibodies or fragments (e.g. U.S. Pat. No. 4,676,980 A); using leucine zippers to produce bi-specific antibodies; using "diabody" technology for making bispecific antibody fragments (e.g., Holliger et al, PNAS 90 (1993) 6444-6448); and using single-chain Fv (sFv) dimers; and preparing trispecific antibodies. Engineered antibodies with three or more functional antigen binding sites, including "Octopus antibodies" are also included herein (e.g. US 2006/0025576 A1). The antibody or fragment to be used herein also includes a "Dual Acting Fab" or "DAF" comprising an antigen binding site that binds to HTT as well as another, different antigen (see US 2008/0069820 A1, for example). The antibody or fragment herein also includes multispecific antibodies described in WO 2009/080251 A, WO 2009/080252 A, WO 2009/080253 A, WO 2009/080254 A, WO 2010/112193 A, WO 2010/115589 A, WO 2010/136172 A, WO 2010/145792 A, and WO 2010/145793 A.

A specifically preferred bispecific antibody comprises more than one binding region to HTT, especially binding regions to both, PRR and C6, as defined herein.

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the HVRs and FRs. Conservative substitutions are shown in the following table under the heading of "preferred substitutions". More substantial changes are provided below in reference to amino acid side chain classes. Amino acid substitutions may be introduced into an antibody of interest and the products screened for a desired activity, especially retained/improved antigen binding, or improved stability.

| Original Residue | Exemplary Substitution | Preferred Substitution |
|---|---|---|
| Ala (A) | Val, Leu, Ile, | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. One type of substitutional variant involves substituting one or more hypervariable region residues of a parent antibody (e.g. a humanized or human antibody). Generally, the resulting variant (s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process, and/or SDRs (a-CDRs), with the resulting variant VH or VL being tested for binding affinity. Affinity maturation is effected by constructing and reselecting from secondary libraries. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modelling. CDR-H3 and CDR-L3 in particular are often targeted.

In certain embodiments, substitutions, insertions, or deletions may occur within one or more HVRs so long as such alterations do not substantially reduce the ability of the antibody to bind HTT. For example, conservative alterations (e.g. conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions. A useful method for identification of residues or regions of an antibody that may be targeted for mutagenesis is called "alanine scanning mutagenesis". In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighbouring residues may be targeted or eliminated as candidates for substitution. Variants may be screened to determine whether they contain the desired properties. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

The PRR (proline-rich-region) site of Huntingtin is located close to the poly-Q sequence of the protein. It is known from the literature that the PRR region is functionally relevant to the Huntingtin protein (Modregger et al 2002). An intrabody derived from a recombinant scFv library targeting the PRR region of Huntingtin inside the cell was shown to be beneficial in an animal model for Huntington's disease (Southwell et al., 2011) by selectively increasing the intracellular turnover of the mutant form of HTT protein. Monoclonal antibodies recognizing the polyproline stretches flanking the PRR region, have previously been published as probes (mAB MW7 by Ko et al. 2001) however no therapeutic use in Huntington's disease had been considered or could be demonstrated because of the low complexity of its epitope consisting of a polyproline stretch not unique for Huntingtin within the human proteome. More generally, targeting of Huntingtin by apheresis has not previously been considered because Huntingtin had always been regarded as intracellular target suited only for intracellular targeting. In contrast to monoclonal antibody MW7, that binds epitopes with more than 5 consecutive prolines (Ko et al., 2001), mAB PRR13 provided with the present invention has a complex epitope and specifically and selectively binds to its core epitope contained on p6773, e.g. as demonstrated in Example 5; however, both antibodies may be used in the apheresis device according to the present invention.

According to the present invention it is especially preferred to use immobilised anti-HTT monoclonal antibodies in the present apheresis device.

The present invention provides a monoclonal antibody for use in the present apheresis device having a binding domain capable of binding to HTT protein or a fragment thereof containing the sequence of p7543 (SEQ ID No. 3) or preferably the core epitope of C6-17, e.g. as determined in Example 4. In a preferred embodiment said monoclonal antibody is characterised as being the monoclonal antibody C6-17, which comprises a heavy chain variable region CDR1 comprising GYTFTEYT (SEQ ID No. 66), a heavy chain variable region CDR2 comprising INPNNGGT (SEQ ID No. 67), a heavy chain variable region CDR3 comprising ASLDGRDY (SEQ ID No. 68), a light chain variable region CDR1 comprising QSLLNSRTRKNY (SEQ ID No. 69), a light chain variable region CDR2 comprising WAS (SEQ ID No. 7δ) and a light chain variable region comprising KQSYNLLT (SEQ ID No. 71), e.g. as shown in Example 5.

According to the present invention, caspase region 586 is referred to a region on the HTT protein surrounding a previously defined caspase cleavage site at Position 586 of the Huntingtin protein that is susceptible to protease cleavage by caspase 6 and other proteases such as caspase 2, 8, or 10 (Wong et al. 2014). The etiological role of protease cleavage within this region was previously established by Graham et al. 2006 and prevention or reduction of the resulting Huntingtin fragment has been recognized as beneficial. In the present invention, it is demonstrated that particular peptides derived from this region can effectively induce antibodies with unexpectedly stronger accessibility to Huntingtin than neighbour peptides from the same region, e.g. as shown in Example 1 and 7. Antibodies generated by these peptides are preferred for use in the apheresis device according to the present invention.

In yet another embodiment, the present invention provides a monoclonal antibody for use in the present apheresis device having a binding domain capable of binding to a peptide of the HTT protein having a sequence of p7564 (SEQ ID No. 2) or preferably the epitope of MIDI, e.g. according to Example 5, FIG. 17. In a preferred embodiment said monoclonal antibody is characterised as being the monoclonal antibody M1D1, which comprises a heavy chain variable region CDR1 comprising GFTFNTYA (SEQ ID No. 72), a heavy chain variable region CDR2 comprising IRSKSNNYAT (SEQ ID No. 73), a heavy chain variable region CDR3 comprising VRHGEYGNPWFAY (SEQ ID No. 74), a light chain variable region CDR1 comprising QSLVHSNGNTY (SEQ ID No. 15), a light chain variable region CDR2 comprising KVS (SEQ ID No. 76) and a light chain variable region comprising SQSTHVPYT (SEQ ID No. 77), e.g. as described in Example 5.

In contrast to prior art monoclonal and polyclonal antibodies derived from a peptide $^{583}$IVLD$^{586}$ (SEQ ID No. 101) occurring at high frequency within the human proteome (Warby et al., 2008), antibody M1D1 recognizes a core epitope consisting of the Huntingtin-derived sequence SSEIVLD (SEQ ID No. 102) containing a free C-terminal aspartic acid that is unique within the human RefSeq protein database thereby providing high specificity towards caspase cleaved Huntingtin protein, e.g. as shown in Example 4 FIG. 12 and Example 5 FIG. 17. In contrast to the antibody of Warby et al, the antibody according to the present invention is more specific. It also has a different core epitope than "IVLD" (SEQ ID No. 101) (see Example 1, FIG. 3). This higher specificity is also due to the fact that "IVLD" (SEQ ID No. 101) (according to Warby) occurs more than several 100 times within the human proteome, whereas the M1D1 epitope occurs only once according to BLAST-RefSeq analysis. M1D1 as provided with the present invention is a distinct clone with unique CDR's—isotype IgM. However, as already stated, all these antibodies may be used in the apheresis device according to the present invention due to their specificity for HTT. According to a preferred embodi- Hament, a combination of mABs is used according to the present invention. Such combination can be beneficial due to the combinatorial/avidity aspect. The specificity of M1D1 for the neoepitope generated by capsase 6 cleavage of HTT is particularly beneficial for apheresis since it will specifically deplete the previously described toxic N-terminal fragment of HTT (e.g. Graham et al 2006 and citations therein).

According to a preferred embodiment, the antibody according to be used in the apheresis device of the present invention comprises the following VH and VL amino acid sequences:

>C6-17 VH Consensus Amino Acid Sequence:
(SEQ ID No. 60)
MGWSCIMLFLLSGTAGVLSEVQLQQSGPELVKPGASVKISCKTSGYTFTE

YTMHWVKQSHGKSLEWIGGINPNNGGTRYNQKFKGKATLTVDRSSSTAYM

ELRSLTSEDSAVYYCASLDGRDYWGQGTTLTVSSAKTTAPSVFPLA

>C6-17 VL Concensus Amino Acid Sequence:
(SEQ ID No. 61)
MVLMLLLLWVSGTCGDIVMSQSPSSLAVSAGEKVTMSCKSSQSLLNSRTR

KNYLAWYQQKPGQSPKLLIYWASTRESGVPDRFTGSGSGTDFTLTISSVQ

AEDLAVYSCKQSYNLLTFGAGTKLELKRADAAPTVSIFPPSSEQLTSGGA

SVVCFLNNFYPK

According to a preferred embodiment, the antibody according to be used in the apheresis device of the present invention comprises the following VH and VL amino acid sequences:

>PRR13 VH Consensus Amino Acid Sequence:
(SEQ ID No. 62)
MGWSWVMLFLLSGTGGVLSEVQLQQSAPELVKPGASVKMSCKASGYSFTD

FYMKWVKQSHGKGLEWIGDIDPKNGDTFYNQKFKGRATLTVDKSSSTAYM

QLNSLTTEDSAVYYCATYYGYTMDYWGQGTSVTVSSAKTTAPSVYPLAPV

CGDTTGSSVTLGCLVKGYF

>PRR13 VL Consensus Amino Acid Sequence:
(SEQ ID No. 63)
MDFQVQIFSFLLISASVIMSRGQIVLTQSPAIMSASLGERVTMTCTASSS

VTSSYLHWYQQKPGSSPKLWIYSTSNLASGVPARFSGSGSGTSYSLTISS

MEAEDAATYYCHQYRRPPRTFGGGTKLEIKRADAAPTVSIFPPSSEQLTS

GGASVVCFLNNFYPR

According to a preferred embodiment, the antibody according to be used in the apheresis device of the present invention comprises the following VH and VL amino acid sequences:

>M1D1 VH Consensus Amino Acid Sequence:
(SEQ ID No. 64)
MDFGLSWVFFVVFYQGVHCEVQLVESGGGLVQPKGSLKLSCAASGFTFNT

YAMNWVRQAPGKGLEWVARIRSKSNNYATYYADSVKDRFTISRSSDQSML

YLQMNNLKTEDTAMYYCVRHGEYGNPWFAYWGQGTLVTVSAESQSFPNVF

PL

>M1D1 VL Consensus Amino Acid Sequence:
(SEQ ID No. 65)
MKLPVRLLVLMFWIPASSSDVVMTQTPLSLPVSLGDQASISCRSSQSLVH

SNGNTYLHWYLQKPGQSPKLLIYKVSNRFSGVPDRFSGSGSGTDFTLKIS

RVEAEDLGVYFCSQSTHVPYTFGGGTKLEIKRADAAPTVSIFPPSSEQLT

SGGASVVCFLNNFYPK.

According to a preferred embodiment, the antibody according to the present invention is a humanised antibody, especially an antibody comprising the following VH and VL amino acid sequence:

>hPRR13 VL (heavy chain variable region):
(SEQ ID No. 95)
EIVLTQSPSSLSASVGDRVTITCTASSSVTSSYLHWYQQKPGKAPKLLIY

STSNLASGVPSRFSGSGSGTDFTFTISSLQPEDIATYYCHQYRRPPRTFG

GGTKLEIKR

>hPRR13 VH (heavy chain variable region):
(SEQ ID No. 96)
EVQLVESGPEVKKPGATVKISCKVSGYTFTDFYMKWVQQAPGRGLEWMGD

IDPKNGDTFYNQKFKGRVTMTADTSTGTAYMQLSSLTSEDTAVYFCASYY

GYTMDYWGQGTTVTVAS

>hC6-17 VL (light chain variable region):
(SEQ ID No. 97)
DIVMTQSPDSLAVSLGERATINCKSSQSLLNSRTRKNYLAWYQQKPGQPP

KLLIYWASTRESGVPDRFSGSGSGTDFTLTISSLQAEDVAVYYCKQSYNL

LTFGGGTKLEIK

>hC6-17 VH (heavy chain variable region):
(SEQ ID No. 98)
QVQLVQSGAEVKKPGASVKVSCKASGYTFTEYTMHWVRQAPGRGLEWMGG

INPNNGGTRYNQKFKGRVTMTRDTSIRTAYVELSRLTSDDTAVYYCASLD

GRDYWGQGTLVTVSS]

The present invention provides an antibody or a HTT binding molecule for use in the prevention and/or treatment of Huntington's disease, wherein the antibody or the HTT binding molecule or a derived fragment (such as Fab or F(ab)2 thereof) is used as adsorber for depletion of soluble or aggregated HTT and HTT-derived fragments from plasma in therapeutic apheresis. Such antibodies for use in apheresis are preferably polyclonal or monoclonal antibodies binding an immunogenic peptide of HTT. Specifically, monoclonal antibodies or antibody-derived fragments binding to the immunogenic peptides p6773 (SEQ ID No. 1) or p7543 (SEQ ID No. 3) or p7564 (SEQ 1 No. 2) and binding to the immunologically accessible regions PRR and caspase cleavage region 586 as demonstrated in Example 1 are particularly preferred for use in apheresis as demonstrated for mAB PRR13 and mAB C6-17, e.g. as in Example 6 FIG. 18. It is also preferred to use a combination of antibodies, e.g. a combination of two or more of the antibodies disclosed herein. Preferably, the anti HTT antibodies according to the present invention are coupled to a solid carrier which is suitable for contacting with the blood stream, more specifically with the plasma of a human individual.

According to the present invention plasma apheresis is defined as a medical technology in which the blood of a patient is passed through an apparatus that separates out one particular constituent and returns the remainder to the circulation. According to the invention, apheresis is used to separate out soluble or aggregated Huntingtin, or fragments derived thereof from the plasma by use of the antibodies or their derivatives provided in the present invention. According to the present invention an apheresis device comprises a solid column which can be brought into contact with the blood or with the plasma flux and which has receptors that bind the HTT protein. A sterile and pyrogen-free column is preferably used as apheresis carrier. Herein, "column" is defined as a module of any shape having a matrix material to which proteins can be chemically coupled. Specific receptors that bind the HTT protein and that are coupled to the column can be for instance antigen-binding molecules, such as antibodies, Fab, Fd, Fab', F(ab')2, Fv, or ScFv fragments. When the receptors coupled to the matrix material of the column comprises antibodies, the antibodies can be polyclonal antibodies raised by well-known means in animals such as sheep, rabbits, goats, camelids or sharks. Alternatively the antibodies bound to the columns may be monoclonal antibodies produced by well-known means using human HTT or fragments thereof as an antigen. When the antigen-binding molecule to be coupled to the column is raised in an animal, it is especially important to assure that any viruses present in the animal serum are inactivated, e.g. by heat treatment (U.S. Pat. No. 5,817,528 A) or any other technique known to a person skilled in the art. Once the animal serum or other source of antibody or antigen-binding molecule has been validated as pathogen-free, it is preferably purified to select the appropriate antigen-binding molecules destined for coupling to the therapeutic column product according to U.S. Pat. No. 5,817,528 A. Suitably, the purification step involves passage of the antigen-binding molecule solution over a first column ("pre-column") containing a matrix material having albumin coupled thereto and then over a second column ("working column") containing a matrix material containing human Huntingtin coupled thereto. The solution of antigen-binding molecules destined for coupling to the therapeutic column is purified by passage over the pre-column to which non-desired substances bind. The elutant from the pre-column is then passed over the working column, which binds the desired antigen-binding molecules while allowing undesired substances to flow out of the column. Sterile buffers are used for all processes. Then the desired antigen-binding molecules are eluted from the working column in a functional state using for instance successive sodium-citrate/citric acid and sodium-acetate/acetic acid elution buffers as disclosed by U.S. Pat. No. 5,817,528 A or any other technique known to the skilled artisan. The collected antigen-binding molecules are then coupled to a sterile matrix material under sterile conditions. Preferably, the matrix material is a carbohydrate based material such as Sepharose™, dextrane, agarose or cellulose. Other suitable matrix materials include autoclavable matrices such as beads, fibres and membranes or films composed of glass or synthetic polymers such as polymethacrylates, polystyrenes and polyamides. In cases where beads are used, the diameter of the beads is not limited as long as the liquid phase of the apheresis can circulate. However to reduce the flow resistance, those beads having a diameter of 50 to 0.3000 µm, especially 200 to 3000 µm are preferably used. The matrix material is sterilised by pre-rinses with a sterile solution and additional steam treatment at low temperature according to U.S. Pat. No. 5,817, 528 A or any other technique known to the skilled artisan. The sterile and pyrogen-free matrix material is then activated by incubation with cyanogen-bromide solution as described in U.S. Pat. No. 5,817,528 A or any other technique known to a person skilled in the art. Successively the desired antigen-binding molecules are coupled to the column by incubation. Alternatively activation and coupling can also be achieved simultaneously by incubation of the antigen-binding molecules together with 1,1'carbonyldiimidazole according to U.S. Pat. No. 5,817,526 A or any other technique known to a person skilled in the art. Once the coupling procedure is finished, the matrix material having antibodies coupled thereto is extensively washed and tested for cyanate ester, sterility and pyrogenicity. The amount of the antibody to be immobilised in the column and the size of the column are not restricted. The coupled matrix material is also tested for total bound protein, and binding activity of the coupled protein. The coupled matrix material is then filled under aseptic conditions into sterile, depyrogenated, silanized glass housings to form sterile and pyrogen-free protein-coupled columns. The flow rate through the apheresis device may be controlled by appropriately selecting the inner diameters of the tubes of the circuit or by using an auxiliary pump (U.S. Pat. No. 4,770,774 A). The column of the invention can be repeatedly used by eluting the absorbed HTT protein or fragments thereof.

The present invention moreover provides an apheresis device comprising a solid carrier capable of being contacted with the blood or plasma flow, characterised in that the solid carrier includes a specific and selective HTT-binding receptor or adsorber. The carrier of the apheresis device is further defined as being a sterile and pyrogen-free column.

According to the present invention the herein provided apheresis device is preferentially used for providing a prevention and/or treatment device for preventing and/or treating Huntington's disease.

The present invention further provides a kit for use in preventing and/or treating Huntington's disease comprising a solid apheresis carrier containing Huntingtin-binding receptors or adsorbers, wherein said carrier is again a sterile and pyrogen-free column.

In yet another embodiment, the present invention provides a method for diagnosing in vitro Huntington's disease in a mammal, comprising the steps of: determining the level of free, aggregated, complexed or fragmented HTT in a sample of a mammal using the antibodies according to the present invention, especially the antibody PRR13, M1D1 and C6-17, in order to diagnose Huntington's disease, monitor disease progression or otherwise use HTT as biomarker if the level of HTT in said sample is increased in comparison to a reference sample of healthy or individuals, who are genetically unaffected by Huntington's disease. In the course of the present invention it was shown that the pathology of Huntington's disease also correlates with the (low) amount of HTT present in plasma and other body fluids and tissue material. Determination of changes in such (low) HTT levels turned out to be possible with the antibodies according to the present invention, but are, of course, enabled also for other techniques after the disclosure of the present invention that changes in the HTT level are correlating to the disease and the disease status. It is therefore not only possible to diagnose the disease with the present tools but also to monitor the treatment of the disease. This diagnosis aspect may be combined with the present apheresis technology to diagnose and monitor patients that are planned to be or are treated with the apheresis device according to the present invention.

Accordingly, the present invention provides a method for diagnosing in vitro Huntington's disease in a mammal, comprising the steps of:

determining the level of wild type or mutated Huntingtin or fragments thereof in a sample of a mammal using antibodies PRR13, M1D1 or C6-17 alone or in combination;

diagnosing Huntington's disease if the level of wt or mutated Huntingtin in said sample is increased in comparison to a reference sample of healthy individuals, who are genetically unaffected by Huntington's disease;

and, optionally, monitoring the effect of Huntingtin-lowering therapeutic strategies in pre-manifest or manifest Huntington's disease patient samples, wherein the therapeutic strategies are preferably selected from active or passive vaccination.

According to the present invention the determination of the level of mutated HTT in a sample involves preferentially immunoprecipitation- or capture-based assays such as Enzyme-linked Immunosorbent Assay (ELISA), enzyme-linked Immunoassay (EIA), Immunoprecipitations or other surfaces and carriers such as resins and beads, mass spectrometry, western Blot or immune-histochemistry and immunofluorescence-based analysis such as FRET-based assays or suitable imaging methods (e.g. PET, SPECT) and Flow cytometry or any other techniques known to a person skilled in the art.

According to the present invention the sample is preferably obtained from cerebrospinal fluid (CSF), blood, plasma, serum, urine saliva, sweat, or lacrimal fluid, or other body fluids or tissue- and cell extracts, especially brain tissue, muscle tissue and blood-derived cells, where (mutant) Huntingtin expression and structure is changed.

According to the present invention the mammal is preferentially a human being.

Moreover, the present invention provides a method for determining in vitro the stage of Huntington's disease or the effect of a new Huntingtin targeting therapy such as the represent active or passive vaccination approach in a mammal, comprising the steps of:

determining the level of wild type or mutated Huntingtin or fragments thereof in a sample of a mammal using antibodies PRR13, M1D1 or C6-17 alone or in combination (these antibodies can be used alone or in combination for capturing an detecting Huntingtin protein or fragments with subsequent, detection by biochemical means, Mass spectrometry or other analytical methods); and determining the stage of Huntington's disease.

Such determination is also possible via the levels of HTT in the given patient: This can be used to monitor the development of disease by comparing the (change of) HTT levels of a given patient over time (relative determination in the same individual) but also for initial diagnosing of the disease stage (absolute determination in correlation to a cohort of patients with a cohort of patients with a known disease status). The "change of HTT levels" will—at least in the longer run of treatment"—be a reduction in HTT levels so that e.g. plasma HTT levels in patients treated according to the present invention will go down (as e.g. depicted in FIG. 9). However, it is also possible that in some patients or at some stage of the disease (especially if combined with other treatments strategies), at the beginning of the treatment an increase of HTT levels may occur. This, nevertheless, is also indicative of a successful treatment, because e.g. an antibody can paradoxically stabilize a protein in the plasma but at the same time it blocks its pathological activity. This phenomenon was e.g. seen in paradoxic IgE increase after anti-IgE treatment. Another example are antibodies against growth hormone which lead to unexpected increase or its growth promoting effect due to stabilization.

Additionally, the present invention provides a method to monitor the progress of Huntington's disease or to monitor the effectiveness of treatment of Huntington's disease in a mammal, comprising the steps of:

determining the level of mutated HTT in a sample of a mammal using PRR13, M1D1 and C6-17 according to the present invention and determining the progress of Huntington's disease or the effectiveness of treatment of Huntington's disease by comparing the obtained level of mutated HTT with the level of mutated HTT obtained in the first measurement of mutated HTT levels, preferably in a measurement at the time of diagnosis of the disease associated symptoms, wherein a change (which "change" is usually a lowering of HTT levels, at least in the longer run, as explained above) of the HTT level is indicative of a successful therapy and is preferably used for prognostic purpose and adjustment of the therapy.

Again, this method is enabled by the present invention because effectivity of depletion of extracellular HTT as a therapeutic target has been shown for the first time.

In the apheresis method according to the present invention it is not critical to use antibodies that distinguish between "healthy" and "pathological" HTT (i.e. "wild type" or "mutated" HTT). This means that also antibodies that cannot distinguish between these two forms (but bind to both forms) can be used for binding HTT in the apheresis device (or in the diagnostic methods according to the present invention) and are generally preferred in these methods.

The apheresis device according to the present invention may comprise specific Huntingtin caspase region 586 antibodies and antisera and structures derived thereof such as scFv's, Fab, Fd, Fab', F(ab')2, scFAB, intrabodies or Fv, or any other format, especially any of the preferred formats disclosed herein (as a single HTT binding molecule species or as a combination of two or more HTT binding molecules in order to increase avidity and specificity).

In a specifically preferred embodiment of the present invention antibodies or antigen-binding molecules targeting caspase region 586 of Huntingtin (HTT) are used in the apheresis device that are generated by immunisation with the above specified peptides comprising at least one immunogenic peptide of the caspase region 586 of Huntingtin as specified above or in combination, e.g. as demonstrated in Examples 2 and 3.

The invention is further disclosed by the following examples and the figures, yet without being limited thereto.

FIG. 22-23 show examples for antibody humanization.

EXAMPLES

Figure 1:
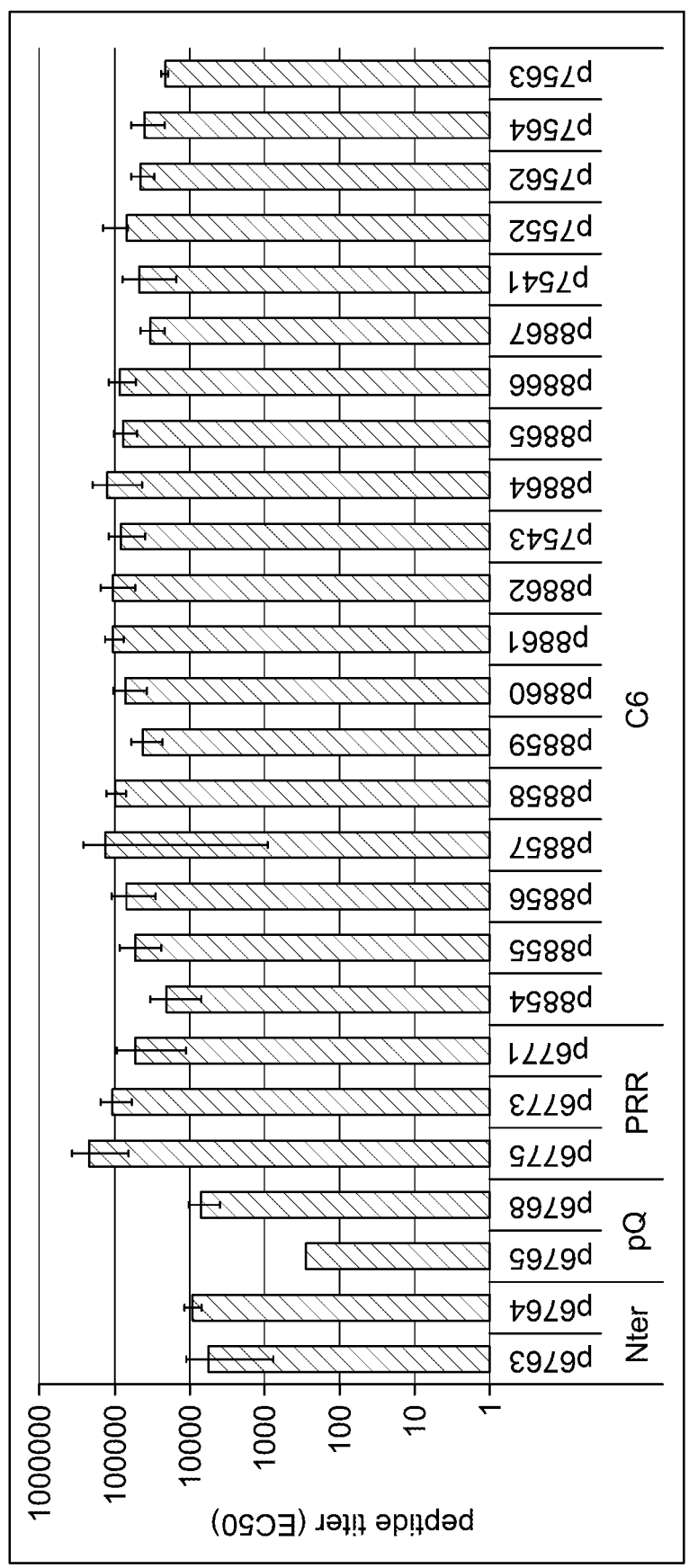
FIG. 1 shows immune-titer analysis by ELISA of peptides derived from the PRR region and caspase region 586 of human Huntingtin (indicated as PRR and C6, respectively) in comparison to the less immunogenic N-terminal and poly-Q region of Huntingtin.

Example 1: —Identification of Peptides Targeting the Huntingtin N-Terminus

Animal Immunizations

Anti-HTT antibody inducing peptides were coupled to KLH carrier using GMBS as amine-sulfhydryl crosslinker (Thermo/Pierce, CatNr. 22309) according to standard recommended procedures for peptide coupling via Cystein. The conjugated peptide was formulated with Aluminium Hydroxide Gel adjuvant (1 µg/ml final concentration; Alhydrogel; Brenntag, CatNr. 21645-51-2) using 30 µg coupled peptide in a volume of 200 µl per injection. Immunizations were typically performed in female BALB/c mice (typically 5 mice per group, aged 10 weeks) using above formulations. Control groups were immunized with non-conjugated KLH and/or PBS and adjuvant alone. Animals were vaccinated 3-6 times in regular intervals of 2 weeks and plasma or serum was collected one day before each boost and at final bleeding.

Peptide ELISA.

Peptide-induced immune responses in mice were determined by ELISA using heparin as anticoagulant. ELISA plates (Nunc Maxisorb) were coated with maleimide activated BSA as carrier to which Cystein containing peptides were coupled via stable thioether bonds. For titrations, plasma dilutions were added and peptide-specific antibodies were quantified by biotinylated anti-mouse IgG (Southern Biotech, CatNr. 1034-08) as detection antibody combined with Streptavidin-POD (Roche, CatNr. 1089153) and subsequent color reaction using ABTS. EC50 values were determined using curve fitting with a 4-parameter logistic using GraphPad Prism (GraphPad Software).

Generation of Cell Extracts Containing N-Terminal Huntingtin Fragment recHTT610.

A DNA covering the coding region of the N-terminal 610 aminoacids of human Huntingtin protein extended by two C-terminal V5 tags were synthesized and cloned via XbaI and BamHI restriction sites into eukaryotic expression vector pCDH-EF1-MCS IRES Puro (SBI; CatNr. CD532A1) yielding plasmid precHTT610. Cloning procedures were performed according to standard molecular biology procedures essentially as indicated by manufacturers including restriction digestions and ligation reactions (NEB Quick ligase kit; CatNr. M2200L), bacterial transformation followed by clone selection and analysis. DNA fragment preparations from agarose gels were performed using standard DNA purification kits (Quiagen; CatNr. 27106). REK293 freestyle cells (Invitrogen; CatNr. R790-07) were grown in medium as indicated by the manufacturer and transiently transfected with precHTT610 (or empty vector as control) using MAXreagent (invitrogen; CatNr. 16447-100) and Optimem (Gibco; CatNr. 31985). 24-48 h after transfection, HEK cell lysates were obtained by cell lysis with NP-40 extraction buffer (150 mM NaCl, 1% NP-40, 50 mM Tris pH), aliquoted and stored at −80° C. Protein concentrations were determined using Qubit (Invitrogen; CatNr. Q32866) according to the manufacturer's instructions.

Detection of Huntingtin by Protein Capture ELISA

Binding of antibodies to N-terminal fragment HTT610 was determined by a standard protein capture ELISA procedure using Maxisorb™ ELISA plates (Thermo; CatNr. 439454), coated with 50 µl of a 1:5000 rabbit anti V5 mAB (Sigma, CatNr. V8137), blocking with blocking buffer (PBS, 1% BSA, 0.1% Tween 20), capturing of recombinant Huntingtin from HEK cell extracts (100 ng/μl total protein) followed by incubation with several dilutions of mouse anti HTT sera (1:100; 1:300 and 1:900) or with mAB2166 as reference (diluted 1:2000; Millipore, Cat Nr. MAB2166) for 1 hour at RT. ELISA incubations, washing and detection procedures were performed according to standard procedures.

Affinity Purification of Antibodies from Plasma

Iodoacetyl-activated magnetic beads (BcMag™; Bioclone CatNr. FG-102) were conjugated with cysteine-containing peptides according to the manufacture's protocol. After plasma/mAB incubation for 2 h at RT, beads were washed with high salt buffer (PBS, 0.2% Triton X-100 supplemented to a final NaCl concentration of 350 mM), bound antibodies were recovered by acid elution (4 elution steps with 100 mM Glycine; pH2.8). After neutralization with a final concentration of 75 mM HEPES pH8, antibodies were concentrated to a volume of 100 μl using Spin-X UF500 tubes (Corning, CatNr. CLS431478), protein concentration was measured as described for protein extracts.

Results

Immune sera from Huntingtin peptide-immunized mice show that peptides derived from the polyproline rich region (PRR) and caspase region 586 (C6) of the Huntingtin protein generally provide higher titers in peptide ELISA analysis (FIG. 1) than comparable peptides derived from the polyglutamine (polyQ) or N-terminal region (comprising the first 17 amino acids) of the protein, respectively. When analysed by protein ELISA (FIG. 2), PRR- and caspase region 586-derived immunsera, show differences in anti-huntingtin protein signal intensity (FIG. 4) and protein specificity (FIG. 2) depending on the peptide sequences of the immunization peptides, allowing for the definition of specific and immunogenic peptide candidates. Peptide p7564 induces immunsera specifically recognizing Huntingtin sequences containing Aspartic Acid at the C-terminus (FIG. 3) thereby providing a means for addressing a disease-specific Huntingtin neo-epitope generated by caspase cleavage of Huntingtin at position 586. FIG. 1: Immune-titer analysis by ELISA reveals that peptides derived from the PRR region and caspase region 586 of human Huntingtin (indicated as PRR and C6, respectively), provide on average titers above 1:10000 in peptide immunized mice, as opposed to animals immunized with polyglutamine region- or N-terminus-derived peptides (indicated as polyQ and Nter, respectively), where the average titers are below 1:10000. Titers are expressed as mean EC50 from 5 individual sera; error bars show standard deviations.

Figure 2:
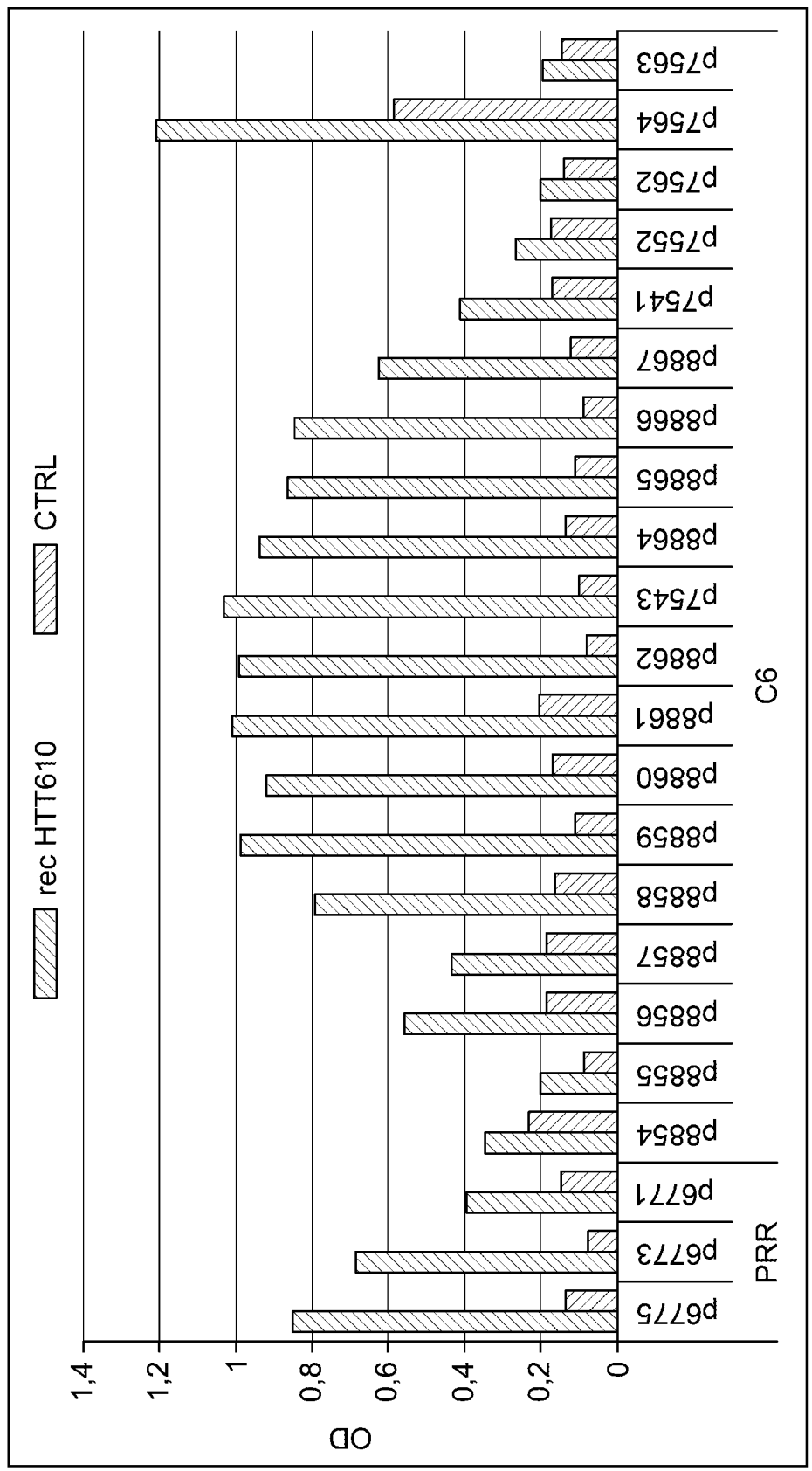
FIG. 2 shows mouse immunsera induced by peptides derived from the PRR and caspase region 586 of human Huntingtin. A recombinant 610 amino acids N-terminal Huntingtin fragment was captured from extracts of transiently transfected HEK293 cells in ELISA setup and incubated with immunesera thereby showing binding and specificity of induced antibodies.

FIG. 2: Mouse immunsera from peptide derived from the PRR and caspase region 586 of human Huntingtin were screened by protein capture ELISA against a recombinant 610 aminoacids N-terminal Huntingtin fragment captured from extracts of transiently transfected HEK cells. Anti-Huntingtin ("recHTT610") and background signals ("CTRL") differ between different peptides despite a homogenous anti-peptide signal distribution as seen in peptide ELISA (shown in FIG. 1). Bars represent signals from 5 pooled immunsera each, tested either against recombinant Huntingtin (CD[recHTT610 extract]; light grey bars) or control extracts (OD[mock transfected ctrl extract]; dark grey bars), respectively at serum dilutions of 1:100.

Figure 3:
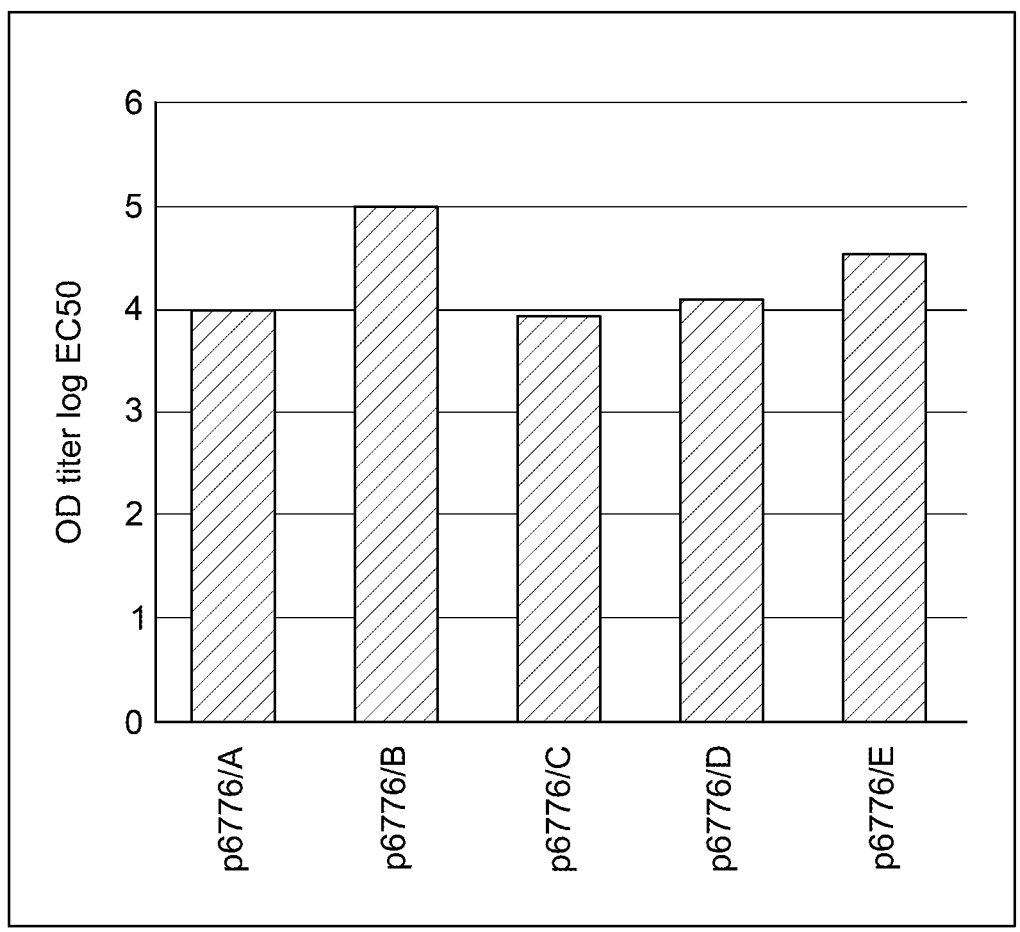
FIG. 3 shows that individual immunsera raised against immunization peptide p6776 provide comparable anti-peptide ELISA titers against the immunization peptide (indicated as log EC50).

FIG. 3: 5 Individual immunsera raised against immunization peptide p6776 provide comparable anti-peptide ELISA titers against the immunization peptide (indicated as log EC50).

Figure 4:
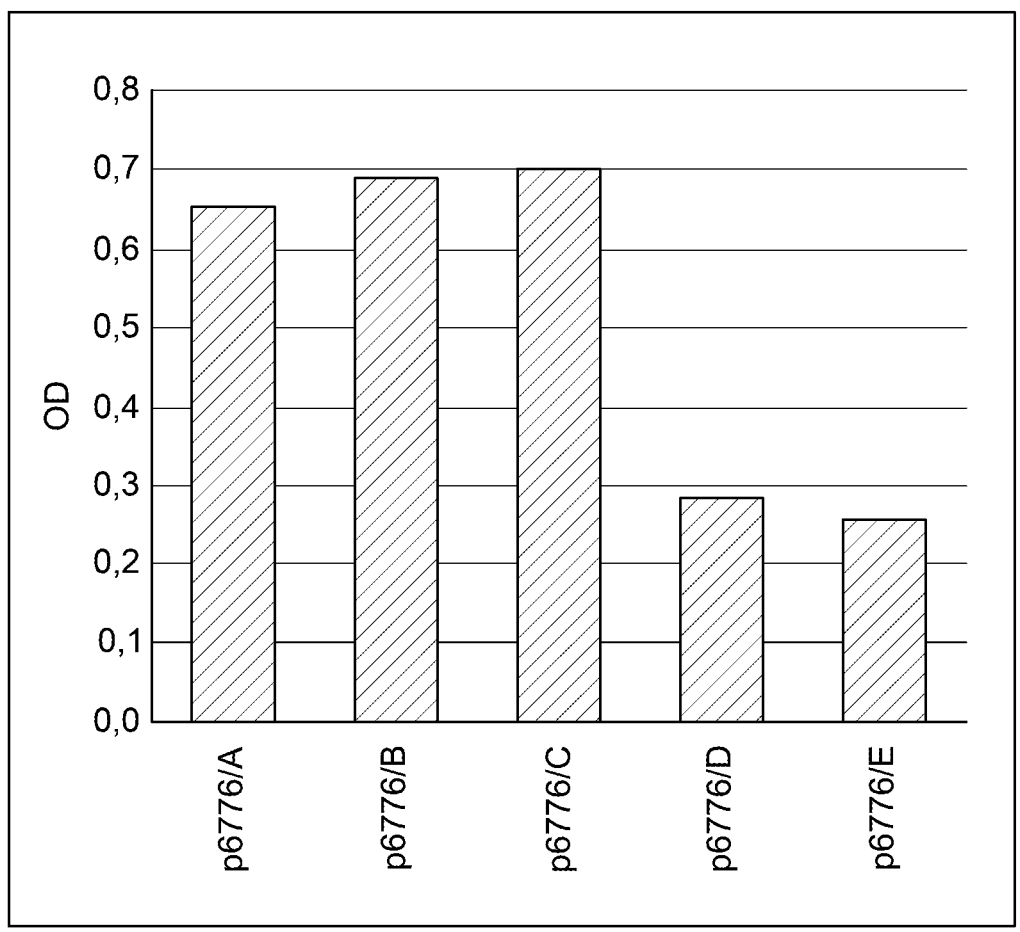
FIG. 4 shows that the same immunsera of FIG. 3 show differences in anti recombinant Huntingtin signals as measured by protein capture ELISA (OD; anti recHTT610) thereby demonstrating individual variation of the immune response.

FIG. 4: In contrast to anti-peptide titers (shown in FIG. 3), the same immunsera show differences in anti recombinant Huntingtin signals as measured by protein capture ELISA (OD; anti recHTT610) thereby demonstrating individual variation of the immune response.

Example 2: —Peptide Immunization of Transgenic R6/1 Mice Overexpressing the First Exon of Mutant Human Huntingtin Provides Beneficial Changes Reflected by Neuropathological Markers in Basal Ganglia R6/1 mice expressing exon 1 of human mutant Huntingtin under a relatively strong promoter (see Bard et al. 2014 and citations therein) were subjected to vaccine injections at week 8, 10, 14 and 24 formulated as in Example 1. For monitoring titers, plasma was collected at 8, 16, 28 and 32 weeks.

Immunohistochemistry

Analysis by immunohistochemistry was essentially performed as described in Mandler et. al. 2014 (PMID: 245257651 using antibodies EM48, SY38, GFAP and NeuN for marker protein detection basal ganlia (Millipore, CatNr. MAB5374, MAB5258, AB5804 and MAB377, respectively).

Results

Immunohistochemical analysis of basal ganglia of peptide immunized 6 months old transgenic R6/1 mice, overexpressing the first exon of mutant human Huntingtin. The effect of peptide immunisation was compared by histopathological comparison of peptide p6771 and p6773-immunized with control groups (KLH, PBS). A clear neuroprotective and Huntingtin-reducing effect in synapses was observed upon immunisation with PRR-derived vaccines thereby demonstrating that peptide-induced anti HTT antibodies are capable of providing a beneficial effect in vivo with respect to the HTT phenotype.

Figure 5:
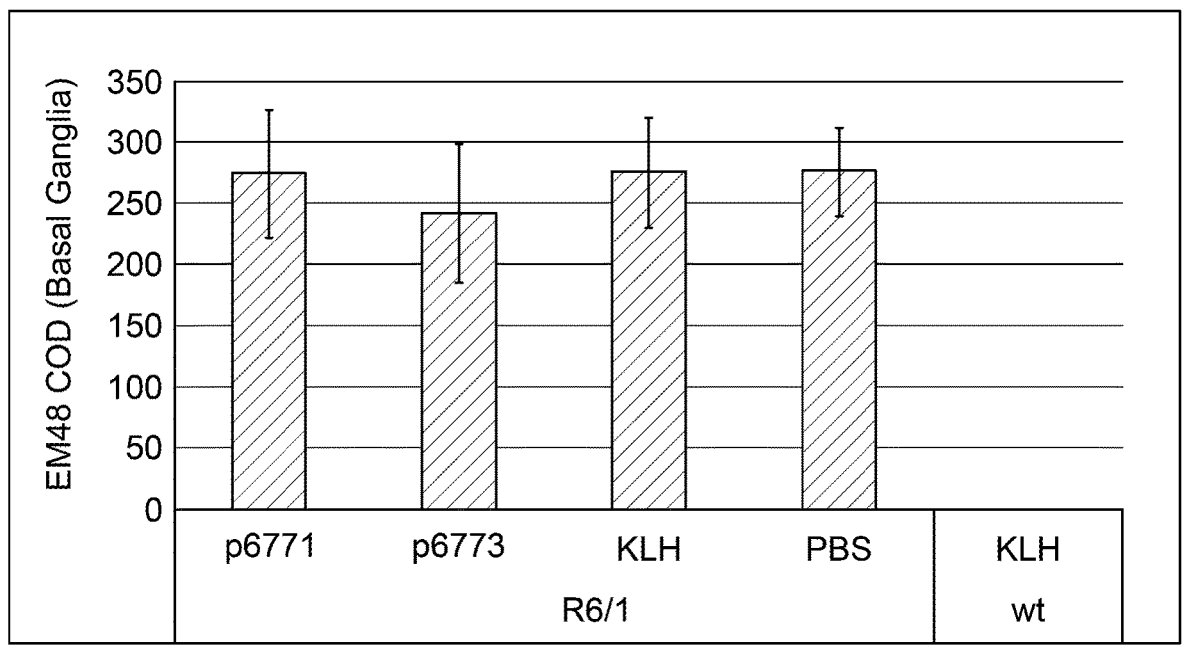
FIG. 5 shows no changes of Huntingtin signals (EM48) in peptide vaccine (p6771, p6773) treated R6/1 mice when comparing to KLH-carrier or PBS treated R6/1 mice or KLH-carrier-treated wild type mice (numbers indicate Corrected Optical Density (CODI using Huntingtin-specific mAB EM48; error bars=standard deviations; n=10).

FIG. 5: No changes of Huntingtin signals (EM48) in peptide vaccine (p6771, p6773) treated R6/1 mice when comparing to KLH-carrier or PBS treated R6/1 mice or KLH-carrier-treated wild type mice (numbers indicate Corrected Optical Density [COD] using Huntingtin-specific mAB EM48; error bars=standard deviations; n=10).

Figure 6:
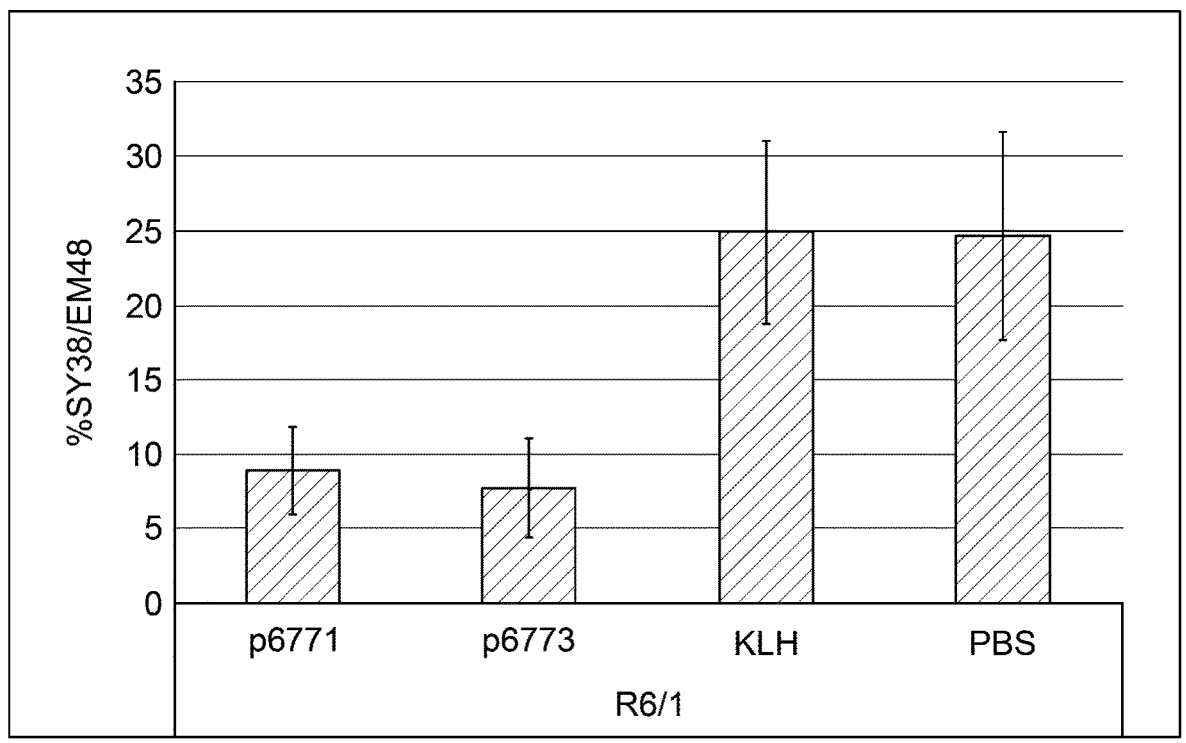
FIG. 6 shows that in contrast to the results from FIG. 5, the number of Synaptophysin-marked synapses (using mAB SY38) containing mutated human HTT (marked by EM48) is significantly reduced (p=0,001) in peptide vaccine-treated R6/1 mice (p6771, p6773) when compared to KLH treated R6/1 mice suggesting a beneficial effect of peptide treatment.

FIG. 6: In contrast, the number of Synaptophysin-marked synapses (using MAB SY38) containing mutated human HTT (marked by EM48) is significantly reduced (p=0.001) in peptide treated R6/1 mice (p6771, p6773) when compared to KLH treated R6/1 mice (Student's ttest; n=10 animals per treatment group). Numbers indicate the ratio (in %) of SY38-positive synapses co-localizing with EM48 signals (error bars=standard deviations; COD=Corrected Optical Density).

Figure 7:
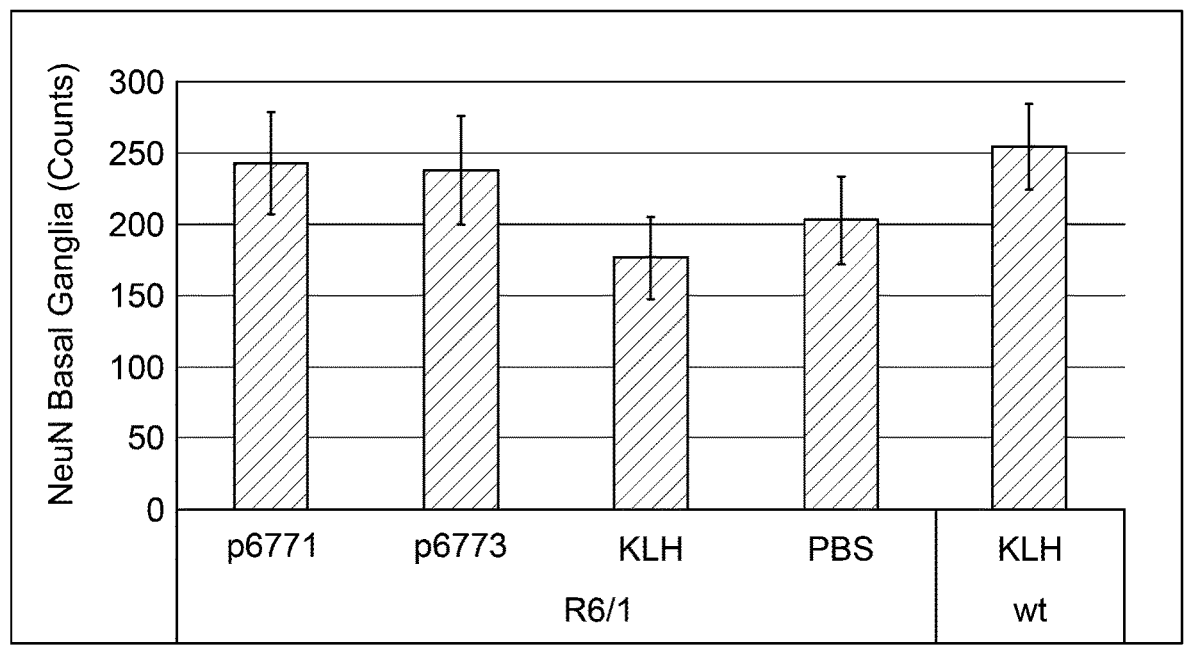
FIG. 7 shows that using neuron-specific marker NeuN, R6/1 mice display a significant neuroprotective effect in basal ganglia in the peptide vaccine-treated groups (p6771, p6773) when compared to control groups treated with KLH or PBS.

FIG. 7: Using neuron-specific marker NeuN, R6/1 mice display a significant neuroprotective effect in basal ganglia in the peptide treated groups (p6771, p6773) when compared to control groups treated with KLH or PBS (p=0.002 and p=0.01, resp. Student's ttest; n=10). Wt KLH=wild type controls; numbers indicate Corrected Optical Density (COD); error bars=standard deviations.

Figure 8:
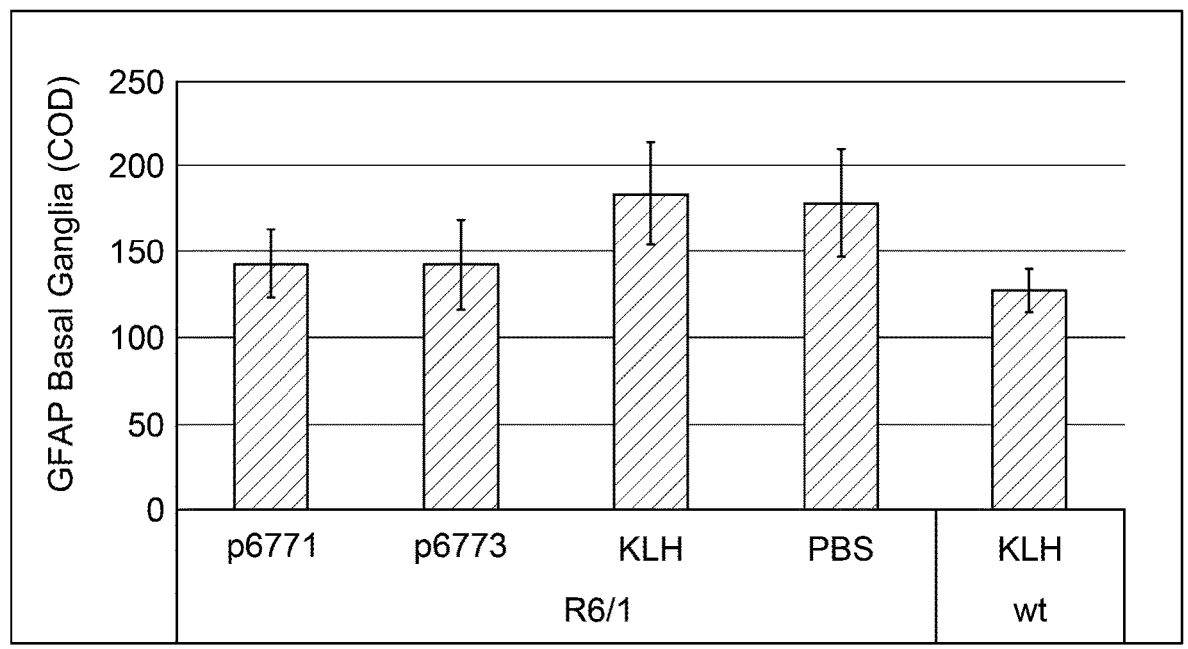
FIG. 8 shows that GFAP staining of basal ganglia shows non-significant reduction of astroglial activation in peptide vaccine treated R6/1 animals (p6771, p6773) when compared to KLH and PBS controls, respectively.

FIG. 8: GFAP staining of basal ganglia shows non-significant reduction of astroglial activation in peptide treated Y6/1 animals (p6771, p6773) when compared to KLH and PBS controls, respectively (COD-Corrected Optical Density; wt KLH=wild type controls; error bars=standard deviations).

Example 3: Combinatorial Vaccine Treatment Leads to Reduced Plasma Huntingtin Levels in YAC128 Transgenic Mice Combined with Motoric Improvement as Measured by Rotarod Test in 4-12 Months Old Animals Thereby Demonstrating that Combined Peptide-Induced Anti HTT Antibodies are Capable of Providing a Beneficial Effect In Vivo with Respect to the HTT Phenotype YAC128 Mouse Immunisations Five cohorts of full length mutant human Huntingtin expressing YAC128 mice (see Bard et al. 2014 and citations therein) and WT control littermates were assembled consisting of 150 total YAC128 and 25 total WT. WT mice were treated with KLH control. YAC128 mice were divided into 6 treatment groups including 5 experimental peptide treatments and a KLH control group. Mice received treatments by s.c. injection at 1, 2, 3, 6 and 9 months of age as in Example 1. For combination immunization, the total peptide amount of 30 µg per dose was kept by combining two peptides at 15 µg+15 µg each per 200 µl volume dose.

Determination of Plasma Huntingtin Levels in Vaccine Treated YAC128 Mice

Plasma Huntingtin levels were determined by FRET (Förster resonance energy transfer)-based detection assay yielding the ratio between the two detection antibodies as previously described by Weiss et al. 2009 [PMID: 19664996]. The correlation between plasma HTT reduction by anti-HTT antibodies and the associated phenotypic changes in YAC128 mice provides evidence for the usefulness of an antibody-based therapeutic strategy for plasma HTT reduction. It is demonstrated that reduction of plasma HTT by peptide induced antibodies is beneficial, therefore it can be expected that the corresponding derived monoclonal antibodies are beneficial for a therapeutic apheresis approach in order to specifically reduce plasma HTT such as demonstrated here.

Rotarod Test

Two-month-old YAC128 mice were trained over 3 consecutive days on the rotarod (Ugo Basille) at a fixed speed of 18 revolutions per minute (RPM). Mice received 3×120 s training trials per day with a 1 h inter-trial interval (ITI). Mice that fell from the rod were immediately replaced for the duration of the trial. The latency to the first fall and number of falls for each training trial were recorded. The average of the 3 trials for each mouse was scored. For longitudinal rotarod testing at 2 month intervals from 2 to 12 months of age, an accelerating program from 5 RPM to 40 RPM over 300 s was used. Mice received 3 trials with a 1 h ITI and the latency to the first fall was recorded. The average of the 3 testing trials was scored.

Results

Figure 9:
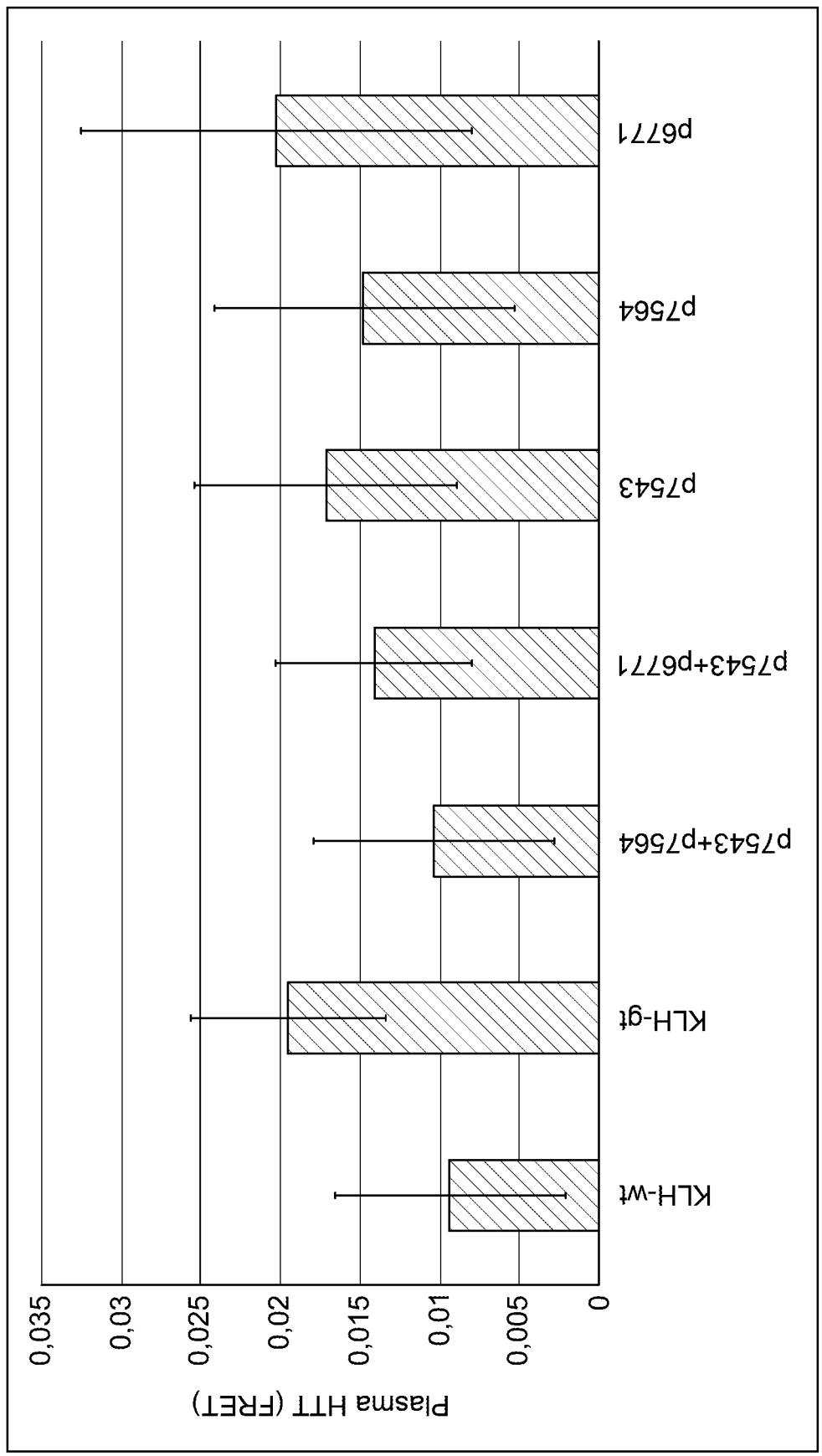
FIG. 9 shows plasma Huntingtin determination by FRET analysis in wt and YAC128 transgenic animals, respectively, at 12 months after single vaccine, combinatorial vaccine or carrier control (KLH) treatment.

FIG. 9: Plasma Huntingtin determination by FRET analysis in wt and YAC128 transgenic animals, respectively, at 12 months after single immunization, combinatorial immunization or carrier control (KLH) treatment. Peptides from the PRR and caspase region 586 regions were used (p6771 and p7564&p7543, respectively). Significant reduction of plasma Huntingtin can be achieved by combinatorial treatment using peptide combinations p7543+p7564 or p7543+ p6771, when comparing plasma Huntingtin levels to carrier control treatment (KLH) (p<0.001 and p<0.01, respectively; Student's ttest; n=25 animals per treatment group). Numbers indicate relative units (FRET); error bars indicate standard deviations.

Figure 10:
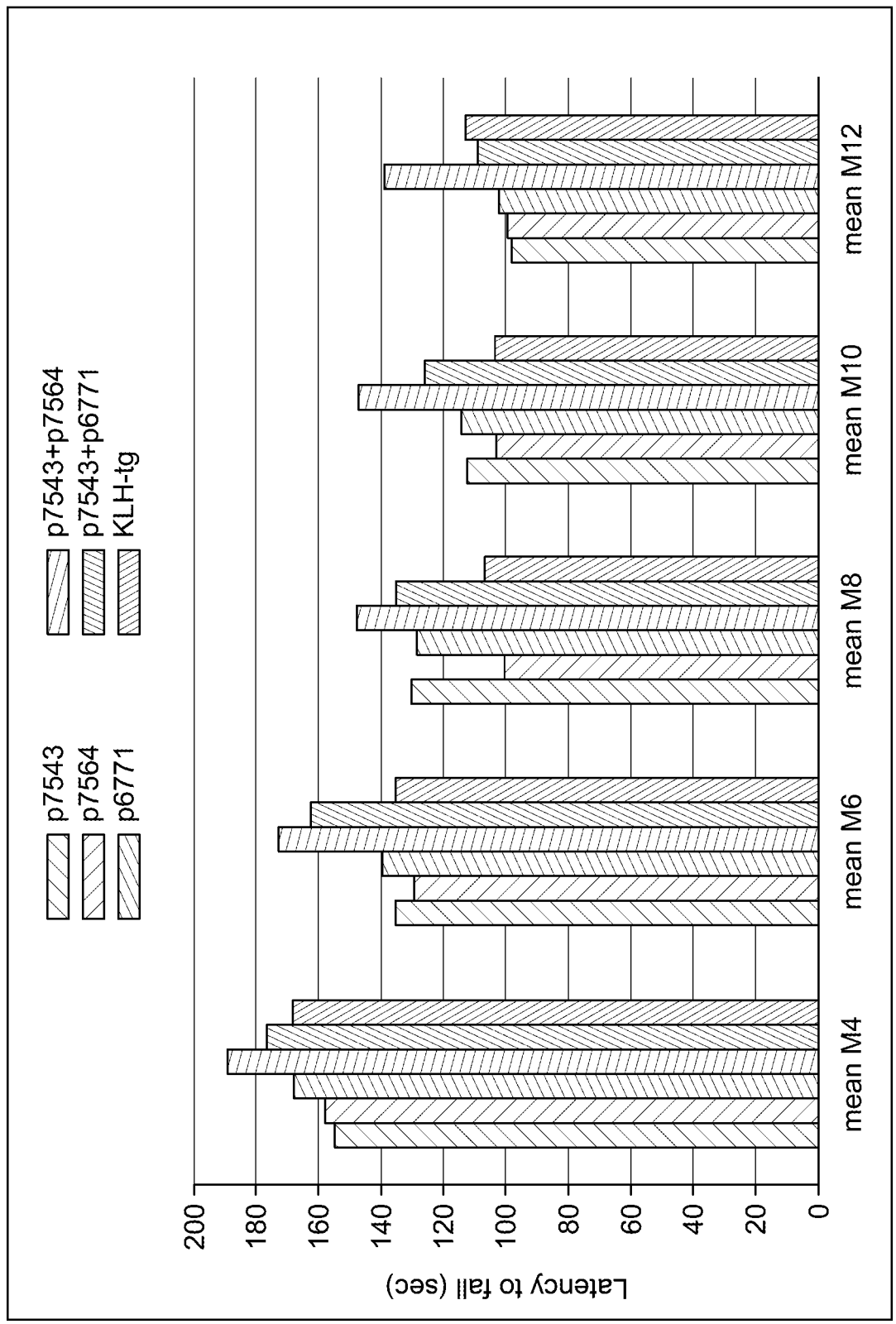
FIG. 10 shows Rotarod test in treated and control YAC128 mice measuring latency to fall (indicated as mean value in seconds; n=25 animals per group) performed at 4, 6, 8, 10 and 12 months (indicated as "mean M4"-"mean M12") in transgenic YAC128 mice treated with various single and combinatorial peptide vaccines as indicated.

FIG. 10: Rotarod test in treated and control YAC128 mice measuring latency to fall (indicated as mean value in seconds; n=25 animals per group) performed at 4, 6, 8, 10 and 12 months (indicated as "mean M4"-"mean M12") in transgenic YAC128 mice treated with various single and combinatorial peptide immunizations as indicated. Notably, the combinatorial groups "p2543+7564" and "p7543+p6771" showed overall better performance in this test when compared to single peptide treated groups p7543, p6771 and 7564, respectively. Motoric improvement was significantly improved at M4-M10 in combination group p7543+7564 when compared to carrier control groups (p<0.03, 0.02, 0.01, resp.; Student's ttest, n=25). This finding parallels plasma Huntingtin reduction as described in FIG. 9 and shows that reduction of HTT in the Blood Stream of a Huntington Patient is Beneficial.

Example 4: Epitope Mapping of Monoclonal and Polyclonal Antibodies Obtained by Immunisation with Peptides p6773, p7564 and p7543

Determination of Core Epitopes

Peptide epitope mapping was performed using alanine substitution scanning by determination of titer values (OD [EC50]) by ELISA as explained in Example 1 or alternatively by applying peptide microarrays as described by Stadler et al. 2008. In brief, peptides containing single alanine-substitutions each position of the peptide were spotted on the arrays, and the loss of signal due to substitutions at single positions was determined by fluorescence labelled secondary antibodies in combination with a Odyssey Imaging System by LI-COR Biosciences. This allowed for an evaluation of the contribution of each individual amino acid of the peptide to the epitope. Using this method, the original immunization peptide to be mapped plus single alanine-substituted variants for each individual position or the peptide were spotted onto microarrays and hybridized by the respective monoclonal antibodies or immune sera to be tested. When the resulting signal from an alanine-substituted peptide was reduced to less than 70% of the signal from the original immunization peptide, the respective alanine-substituted amino acid position was defined as part of the core epitope. Resulting core epitope sequences are provided below from individual sera or mAB's.

Results

Polyclonal, affinity purified antibodies and monoclonal antibodies were derived from individual mice immunized with PRR-region derived peptides (including p6771 and p6773) and caspase region 586-derived peptides (including p7543 and p6776). Epitopes were mapped using alanine scanning. In brief, epitopes of individual sera and monoclonal antibodies were determined by testing antibodies against peptides with single amino acid substitutions for each position using either peptide microarrays or conventional peptide ELISA (as exemplified in FIG. 11)

Peptide and epitope alignments for PRR region-derived peptides p6771 and p6773 as determined by alanine substitution scanning:

```
LPQPPPQAQPLLPC......                        (SEQ ID No. 1)
immunization peptide p6771

(SEQ ID No. 4)
LPQPPPQAQPLLPQPQPC..
immunization peptide p6773

(SEQ ID No. 78)
..........LLPQP.....
epitope mapped for mAB PRR13

(SEQ ID No. 79)
....PPQAQPL.........
epitope mapped for polyclonal p6773 serum 1

(SEQ ID No. 80)
....PPQAQP..........
epitope mapped for polyclonal p6773 serum 2

(SEQ ID No. 81)
........QPLL........
epitope mapped for polyclonal p6773 serum 3

(SEQ ID No. 82)
.....PQAQPLL........
epitope mapped for polyclonal p6773 serum 4
```

Peptide and epitope alignment of p7543 vaccine induced polyclonal immunsera and mAB C6-17 as determined by alanine substitution scanning:

```
                                            (SEQ ID No. 3)
GTDNQYLGLQIGC
immunization peptide p7543

(SEQ ID No. 83)
   QYLGLQIG
epitope mapped for monoclonal AB C6-17

(SEQ ID No. 84)
    YLGLQIG
epitope mapped for polyclonal p7543 serum 1

(SEQ ID No. 85)
  DNQYLGLQIG
epitope mapped for polyclonal p7543 serum 2

(SEQ ID No. 86)
  DNQYLGL
epitope mapped for polyclonal p7543 serum 3

(SEQ ID No. 87)
    YLGLQIG
epitope mapped for polyclonal p7543 serum 4
```

Figure 11:
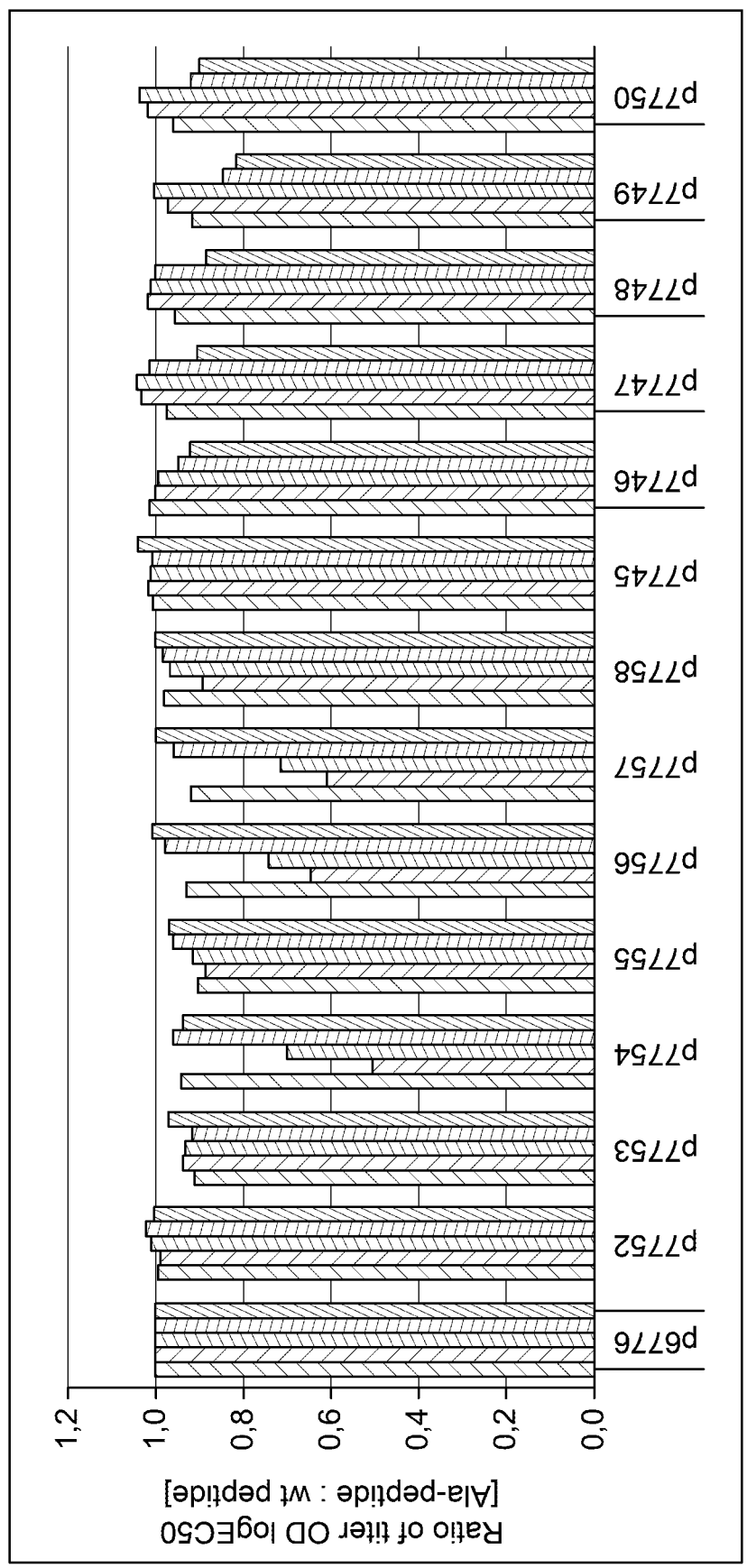
FIG. 11 shows the core epitope of 5 p6776 vaccine-induced immunsera determined by alanine substitution scanning by peptide ELISA using indicated peptides containing single amino acid alanine substitutions.

Peptide and epitope alignments for caspase region 586 derived peptides spanning aspartic acid 586:

FIG. 11: The core epitope of 5 p6776 induced immunsera was determined by alanine substitution scanning by peptide ELISA using indicated peptides containing single amino acid alanine substitutions. The 5 sera (represented by dark to bright bars) were hybridized to alanine substituted peptides as indicated (for peptide sequences see table 1). As a result, 2 out of 5 animals showed signal reduction upon alanine substituted peptides p7754, p7756, p7757 and p7758, respectively, thereby delineating a core epitope with the amino acid sequence IVLD (SEQ ID NO:101). Numbers indicate the ration of titer OD (log $EC_{50}$) [Ala-substituted peptide: wt-peptide].

Figure 17:
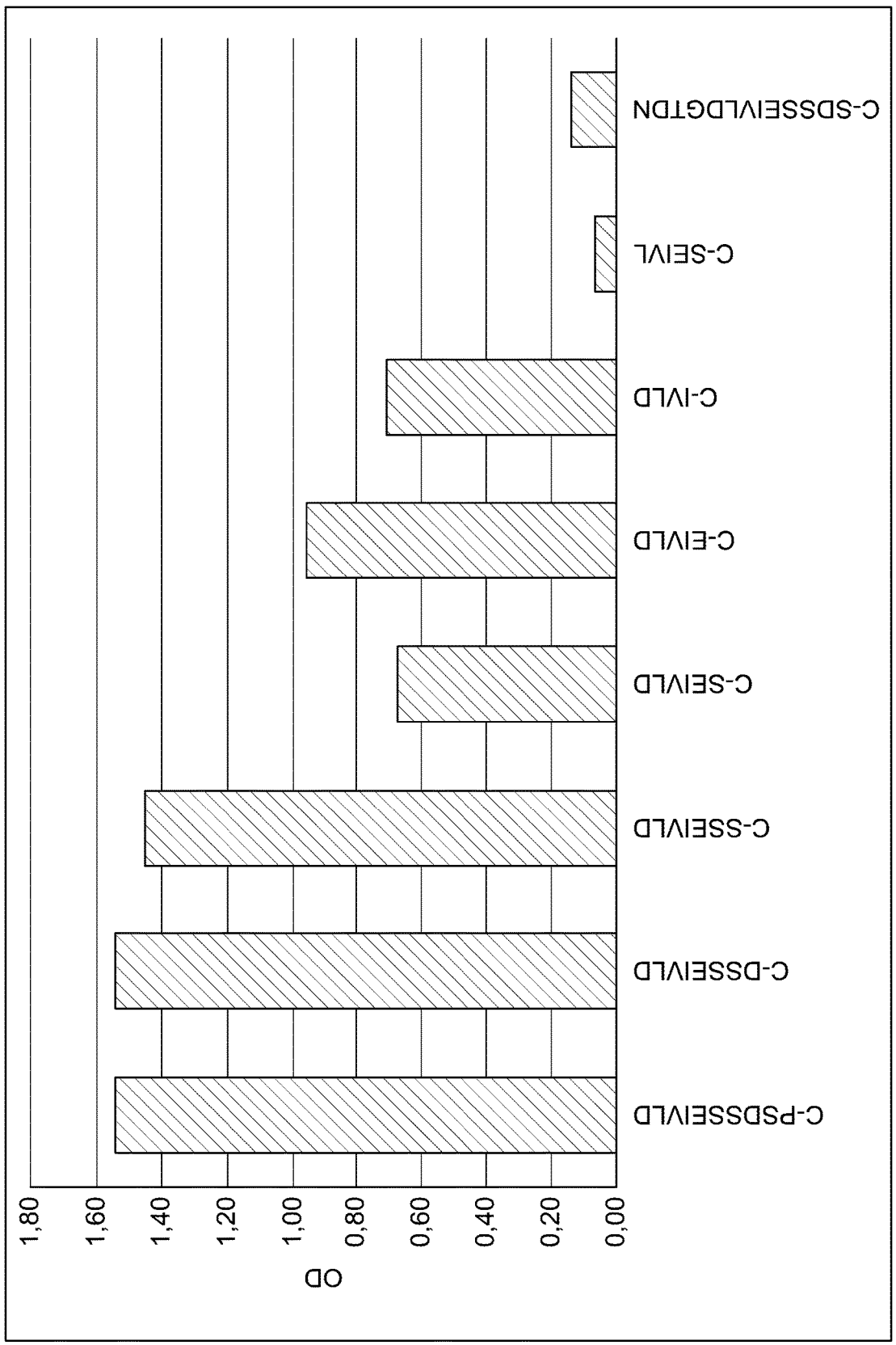
FIG. 17 shows that mAB M1D1 recognizes Huntingtin peptides from the caspase 6 cleavage region of at least 7AA length containing free C-terminal Aspartic Acid.

Epitope mapping of p7564 induced antisera and mAB M1D1 is provided in Example 5, FIG. 17.

FIG. 22: mAB M1D1 specifically recognizes recombinant Huntingtin fragment with free aspartic acid 586 at the C-terminus stronger than recHTT610. Protein ELISA (performed as in Example 1) using recombinant Huntingtin with 610 and 586 amino acids length (HTT610 and HTT586, respectively). Values indicate the ratio of the mAB M1D1 signal (OD; protein capture ELISA as explained in Example 1) to the mAB 2166 control antibody signal. Values were normalized to reference mAB 2166 recognizing an internal epitope present in both fragments as protein loading control.

Example 5: Generation and Characterisation of Monoclonal Antibodies PRR13, C6-17 and M1D1

Monoclonal Antibodies

For the production and isolation of monoclonal antibodies, the ClonaCell-HY Hybridoma Cloning Kit (STEMCELL technologies, CatNr. 28411) was used according to the instructions of the manufacturer. In brief, hybridoma fusions were performed with myeloma cell line SP2-0 under HAT selection and supernatants were initially screened by peptide ELISA using the immunization peptide, respectively, and an irrelevant control peptide for background determination. In the case of M1D1, ELISA against peptide p6776 containing free C-terminal aspartic acid was used in order to determine specificity to cleaved peptide with free C-terminal aspartic acid as indicated in Example 5. Candidate mABs were affinity purified as described and tested against recHTT610 by protein ELISA as indicated in Example 1. The number of screened fusion clones was typically 500 for each fusion, respectively. For VL and VH region sequencing, mRNA from fusion clones was extracted, reverse transcribed using Oligo(dT) primers and PCR amplified using variable domain primers to amplify both the VH and VL regions. VH and VL products were cloned using standard PCR cloning procedures (Invitrogen, CatNr. K4560-01), transformed into TOP10 cells and screened by PCR for positive transformants. Selected colonies were picked and analyzed by DNA sequencing on an ABI3130x1 Genetic Analyzer.

Affinity Purification of Antibodies mABs and polyclonal antibodies were isolated from hybridoma supernatant (SN) and plasma, respectively using BcMag™ Iodoacetyl activated magnetic beads (Bioclone, FG-102) to which cysteine containing peptides were linked according to the manufacture's protocol. After plasma/SN incubation for 2 h at RT, beads were washed with high salt buffer (PBS, 0.2% Triton X-100, supplemented with NaCl to a final concentration of 350 mM) and the bound antibodies eluted 4 times with acidic elution buffer (Thermo, CatNr. 21004). After neutralization in HEPES pH8 (75 mM end concentration), eluted antibodies were concentrated and buffer was exchanged to PBS to a volume 100 µl using Spin-X UF500 tubes (Corning, CLS431478). Antibody concentrations were determined with the Qubit system (Invitrogen, CatNr. Q32866) according to the manufacturer's protocol.

Results

Figure 12:
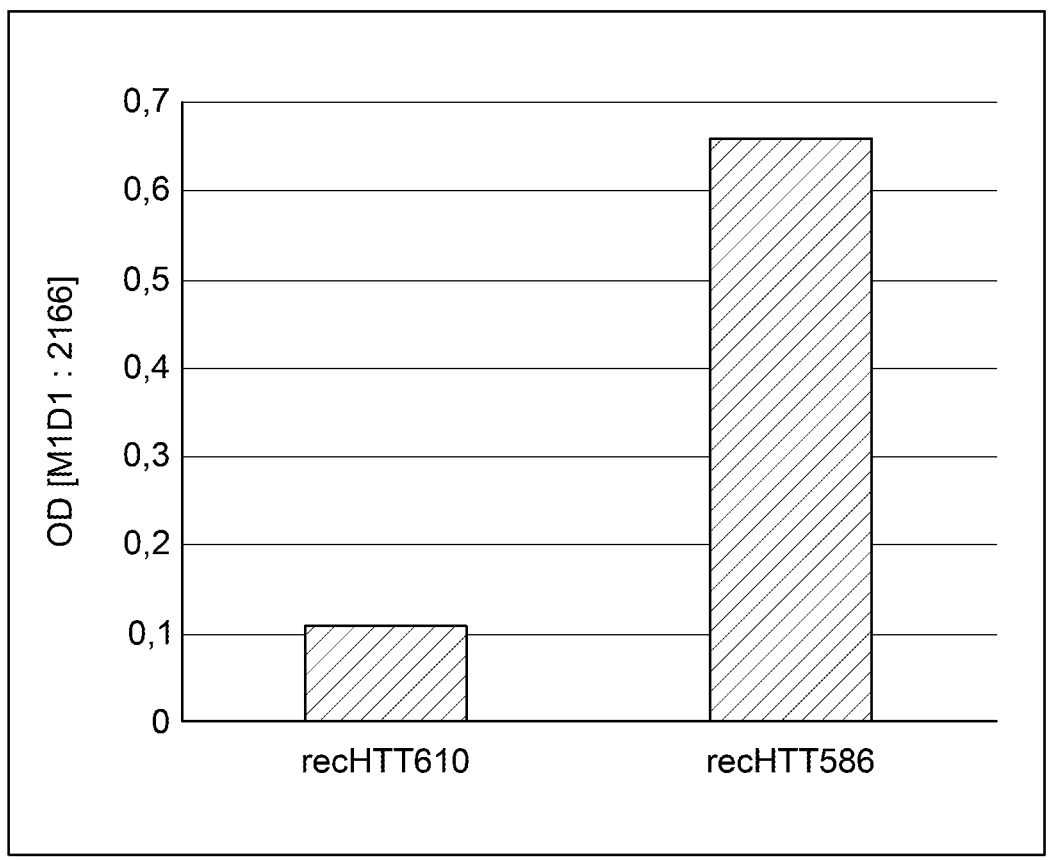
FIG. 12 shows that mAB M1D1 specifically recognizes recombinant. Huntingtin fragment with free aspartic acid 586 at the C-terminus stronger than recHTT610.

Antibody PRR13 was generated by hybridoma technique using peptide p6773 as immunogen. Peptide p6773 shows beneficial neuroprotective effects in active immunization of R6/1 transgenic animals as shown in Example 2 and overlaps with p6771. PRR13 was selected from 9 preselected candidate mABs recognizing a PRR-derived peptide as shown in FIG. 11. Out of the candidate mABs listed in FIG. 13, PRR13 was selected based on its favorable signal/noise ratio when hybridized to recombinant HTT610 as shown in FIG. 12.

Figure 13:
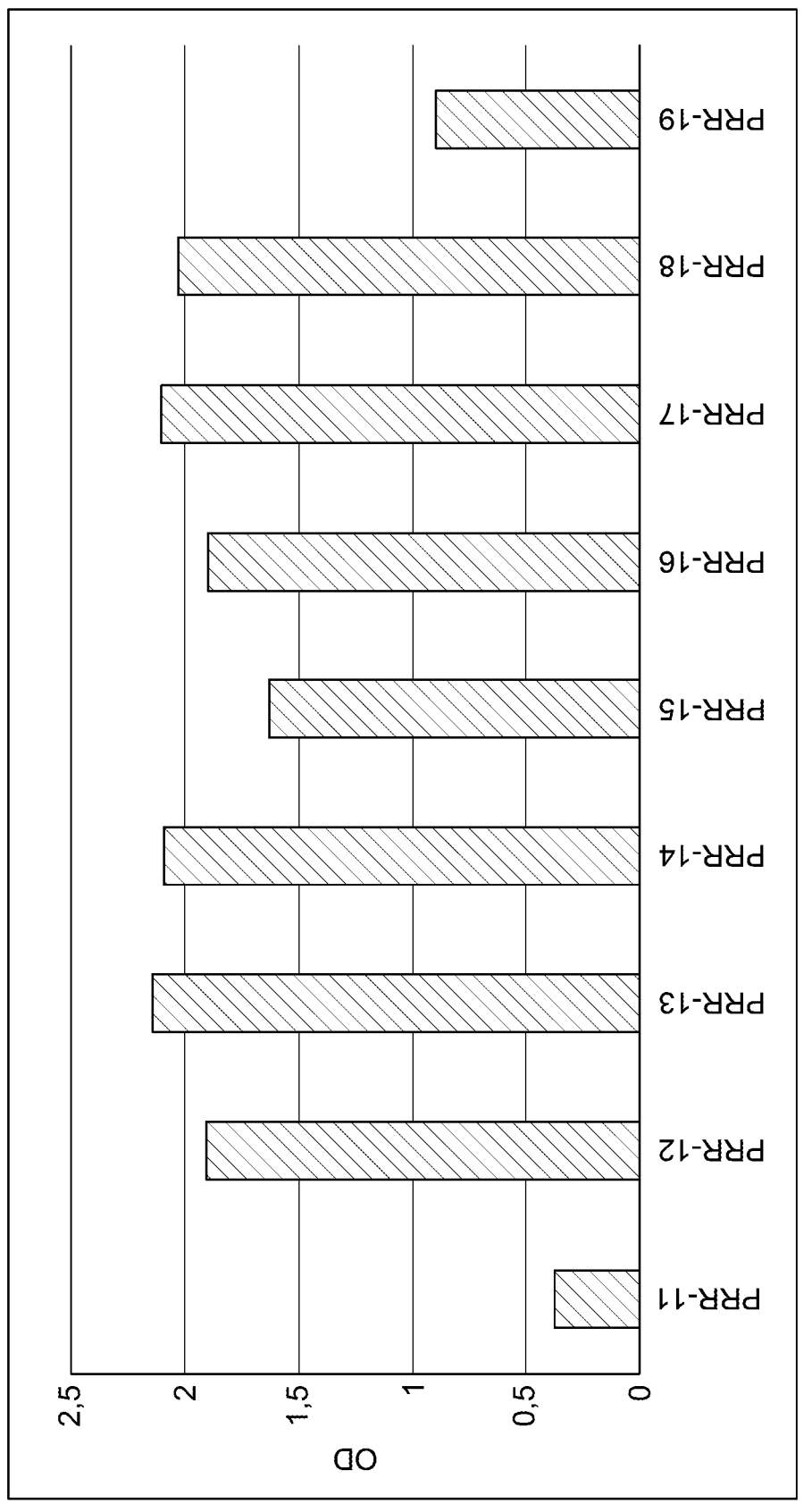
FIG. 13 shows that supernatants from hybridoma derived from mice immunized with peptide p6773 provide strong recognition of the immunization peptide in 7 out of 9 pre-screened candidate clones when tested by peptide ELISA.

FIG. 13: Supernatants from hybridoma derived from mice immunized with peptide p6773 provide strong recognition of the immunization peptide in 7 out of 9 pre-screened candidate clones when tested by peptide ELISA.

Figure 14:
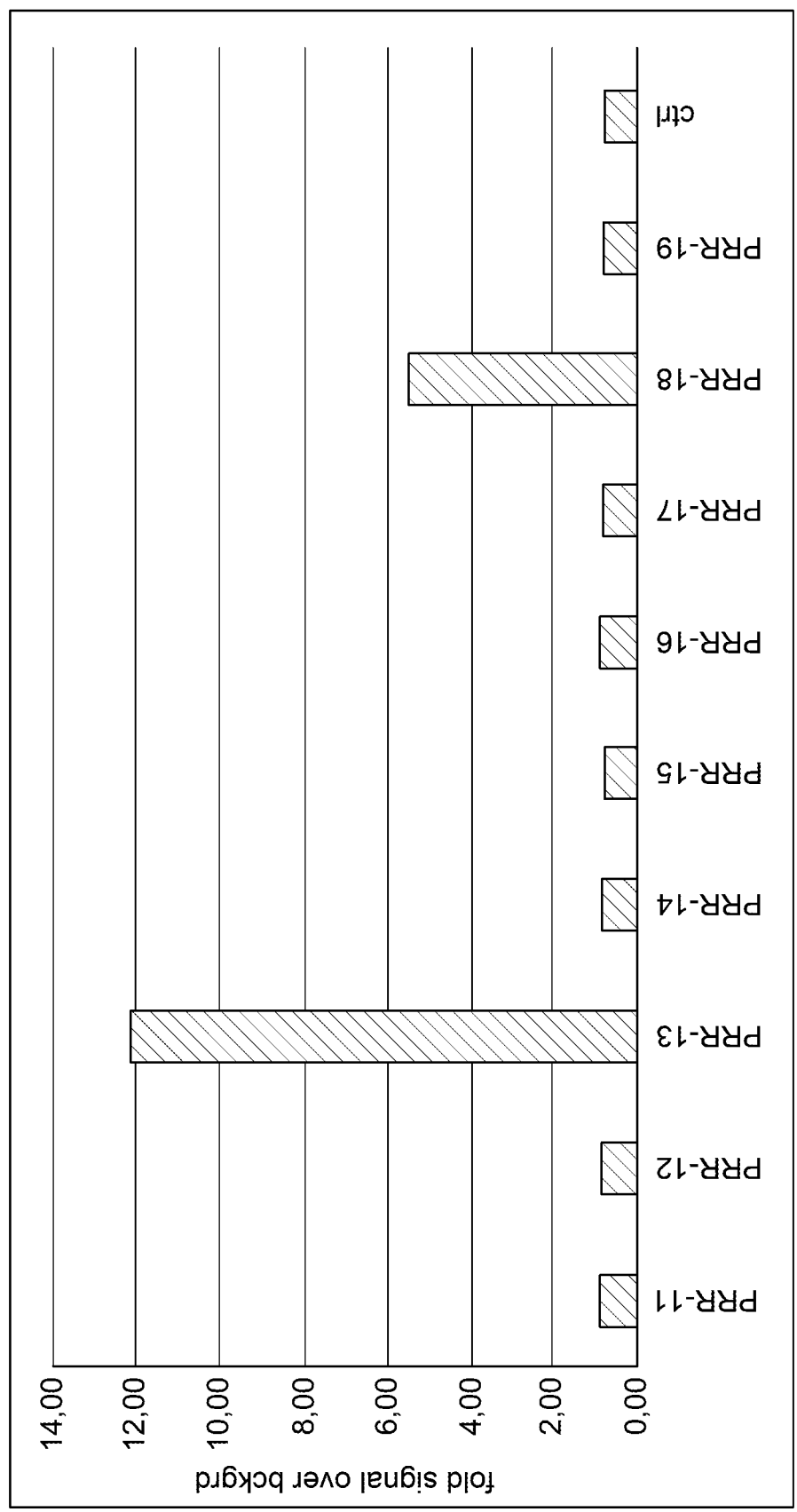
FIG. 14 shows that only 2 out of 9 mAB candidates shown in FIG. 13, namely PRR13 and PRR18, specifically recognize recombinant Huntingtin when tested by recHTT610 capture ELISA.

FIG. 14: In contrast to specific anti peptide signals (FIG. 11), only 2 out of 9 mAB candidates, namely PRR13 and PRR18, specifically recognize recombinant Huntingtin when tested by recHTT610 capture ELISA (as explained in Example 1). These two candidates provided an outstanding signal to noise ratio (i.e. >=4; calculated reHTT610-specific signal: HEK ctrl extracts), and PRR13 was selected for epitope characterization (see Example 4) and variable chain sequencing (see below). PRR13 was determined as IgG subtype mouse IgG2a.

```
>PRR13 VH Consensus Amino Acid Sequence
(SEQ ID No. 62):
MGWSWVMLFLLSGTGGVLSEVQLQQSAPELVKPGASVKMSCKASGYSFTD

FYMKWVKQSHGKGLEWIGDIDPKNGDTFYNQKFKGRATLTVDKSSSTAYM

QLNSLTTEDSAVYYCATYYGYTMDYWGQGTSVTVSSAKTTAPSVYPLAPV

CGDTTGSSVTLGCLVKGYF

>PRR13 VL Consensus Amino Acid Sequence
(SEQ ID No. 63):
MDFQVQIFSFLLISASVIMSRGQIVLTQSPAIMSASLGERVTMTCTASSS

VTSSYLHWYQQKPGSSPKLWIYSTSNLASGVPARFSGSGSGTSYSLTISS

MEAEDAATYYCHQYRRPPRTFGGGTKLEIKRADAAPTVSIFPPSSEQLTS

GGASVVCFLNNFYPR
```

Figure 15:
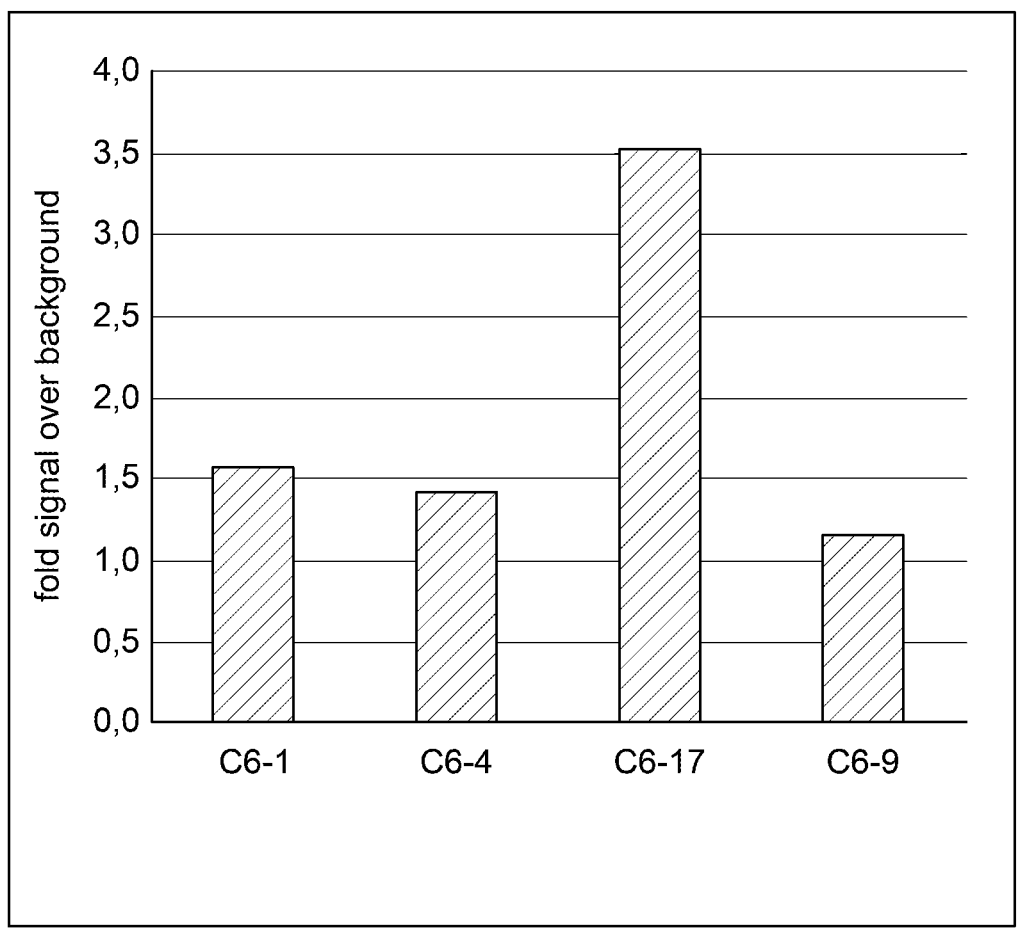
FIG. 15 shows the specificity analysis of 4 preselected anti Huntingtin mAB's derived from peptide p7543 immunized mice.

Antibody C6-17 was generated by hybridoma technique using peptide p7543 as immunogen. Peptide p7543 showed beneficial therapeutic effects in YAC128 transgenic animals as demonstrated in Example 3. Although anti recHTT610 signals were comparable between 4 preselected mABs from this screen as shown in FIG. 13, the signal to noise ratios differed significantly amongst these candidates as shown in FIG. 14 showing a recHTT610 capture ELISA (performed as in Example 1). Based on its specificity and IgG subtype (determined as mouse IgG2a), C6-17 was selected for epitope characterization (see Example 4) and variable chain sequencing:

FIG. 15: Specificity analysis of 4 preselected anti Huntingtin mAB's derived from peptide p7543 immunized mice. Values for 4 mAB candidates represent signal to noise ratios of recombinant Huntingtin-specific CD-signal against control extract (determined by protein capture ELISA as explained in Example 1). mAB C6-17 provides the best signal to noise ratio.

```
>C6-17 VH Consensus Amino Acid Sequence
(SEQ ID No. 60):
MGWSCIMLFLLSGTAGVLSEVQLQQSGPELVKPGASVKISCKTSGYTFTE

YTMHWVKQSHGKSLEWIGGINPNNGGTRYNQKFKGKATLTVDRSSSTAYM

ELRSLTSEDSAVYYCASLDGRDYWGQGTTLTVSSAKTTAPSVFPLA

>C6-17 VL Consensus Amino Acid Sequence
(SEQ ID No. 61):
MVLMLLLLWVSGTCGDIVMSQSPSSLAVSAGEKVTMSCKSSQSLLNSRTR

KNYLAWYQQKPGQSPKLLIYWASTRESGVPDRFTGSGSGTDFTLTISSVQ

AEDLAVYSCKQSYNLLTFGAGTKLELKRADAAPTVSIFPPSSEQLTSGGA

SVVCFLNNFYPK
```

Antibody M1D1 was generated by hybridoma technique using peptide p7564 as immunogen. Peptide p7564 shows beneficial therapeutic effects in YAC128 transgenic animals as demonstrated in Example 3. Monoclonal antibody M1D1 was selected by differential screening of binding to peptides containing a free aspartic acid at the C-terminus against a peptide containing this Aspartic Acid residue embedded within the sequence such as e.g. p6776, as shown in Example 1, FIG. 3. Based on its specificity for the "cleaved" sequence, monoclonal antibody M1D1 was selected for further epitope characterization and variable chain sequencing. It was typed as mouse IgM and it binds to the neo-epitope of a human Huntingtin fragment that is generated upon cleavage of the protein or a corresponding peptide sequence by caspase 6 or any other protease cleaving at amino acid position D586.

Figure 16:
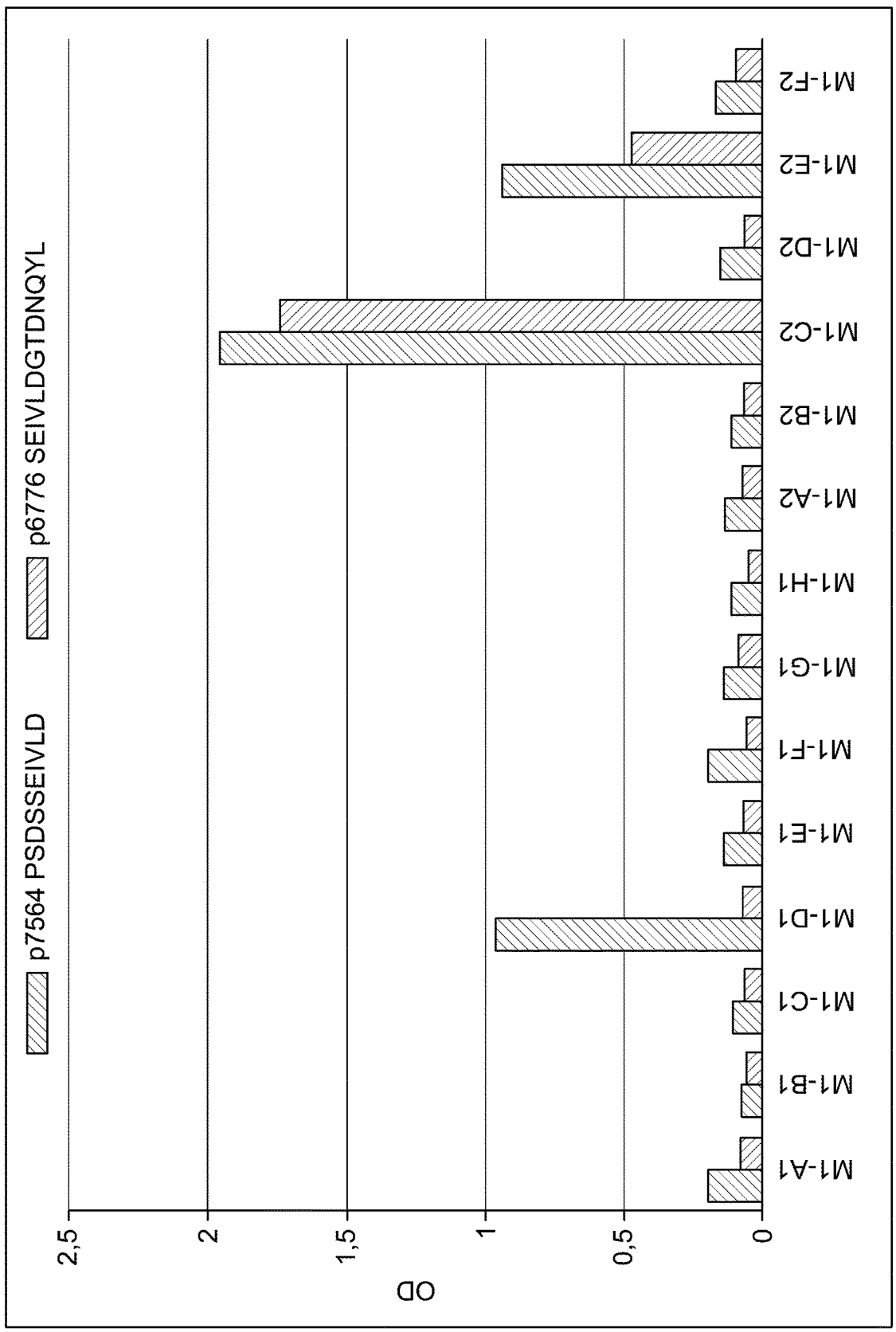
FIG. 16 shows screening of preselected mABs by determination of specificity against. "cleaved" peptide p7564 by peptide ELISA

FIG. 16: Screening of preselected mABs by determination of specificity against "cleaved" peptide p7564 by peptide ELISA (as explained in Example 1). In contrast to e.g. M1-C2, mAB M1D1 shows the most favorable p7564 to p6776 OD signal ratio. M1D1 is therefore specific to the neo-epitope generated by proteolytic cleavage at position 586. The C-terminal aspartic acid of p7564 corresponds to the C-terminal cleavage point generated by caspase 6 and possibly other caspases. It thereby provides the means for specific cleavage detection at this site in analogy to polyclonal antisera generated with therapeutically beneficial peptide p7564 as shown in Example 3.

FIG. 17: mAB M1D1 recognizes Huntingtin peptides from the caspase 6 cleavage region of at least 7AA length containing free C-terminal Aspartic Acid. In contrast, shorter peptides or peptides without free C-terminal Aspartic Acid are not or only weakly recognized by M1D1 thereby demonstrating specificity of this monoclonal antibody for the cleaved sequence with free COOH-terminal aspartic acid such as the free amino acid position 586 of cleaved human Huntingtin protein (Bars represent OD from peptide ELISA at a mAB concentration of 1 ng/µl; peptide designations from left to right are as follows: p7564, p7562, p7552, p7541, p7567, p7568, p7605, p6777).

```
>M1D1 VH Consensus Amino Acid Sequence
(SEQ ID No. 64):
MDFGLSWVFFVVFYQGVHCEVQLVESGGGLVQPKGSLKLSCAASGFTFNT

YAMNWVRQAPGKGLEWVARIRSKSNNYATYYADSVKDRFTISRDDSQSML

YLQMNNLKTEDTAMYYCVRHGEYGNPWFAYWGQGTLVTVSAESQSFPNVF

PL

>M1D1 VL Consensus Amino Acid Sequence
(SEQ ID No. 65):
MKLPVRLLVLMFWIPASSSDVVMTQTPLSLPVSLGDQASISCRSSQSLVH

SNGNTYLHWYLQKPGQSPKLLIYKVSNRFSGVPDRFSGSGSGTDFTLKIS

RVEAEDLGVYFCSQSTHVPYTFGGGTKLEIKRADAAPTVSIFPPSSEQLT

SGGASVVCFLNNFYPK
```

Example 6—Use of Monoclonal Antibodies PRR13 and C6-17 for Depletion of Huntingtin Protein from Human Serum Huntingtin Depletion 100 µg paramagnetic Streptavidin coated beads (Dynabeads T1, CatNr. 65601) were incubated in a buffer volume of 50 µl with 20 ng/µl biotinylated mABs for 1 h at RT. Human serum was diluted 1:4 with PBS and spiked with protein extracts from recHTT610 and mock transfected cells at a final extract concentration was 50-100 ng/µl, respectively obtained as indicated in Example 1. Biotinylated mAB's were coupled to streptavidin beads and incubated o/n at RT with Huntingtin cell extract containing serum. After stringent bead washing (50 mM Tris, 250 mM NaCl, 0.1% Tween), to confirm recHTT610 depletion efficacy by monoclonal antibodies, input serum (containing recHTT610), mock serum and depleted recHTT61.0 containing serum was tested by recHTT610 capture ELISA as in Example 1.

Results

Figure 18:
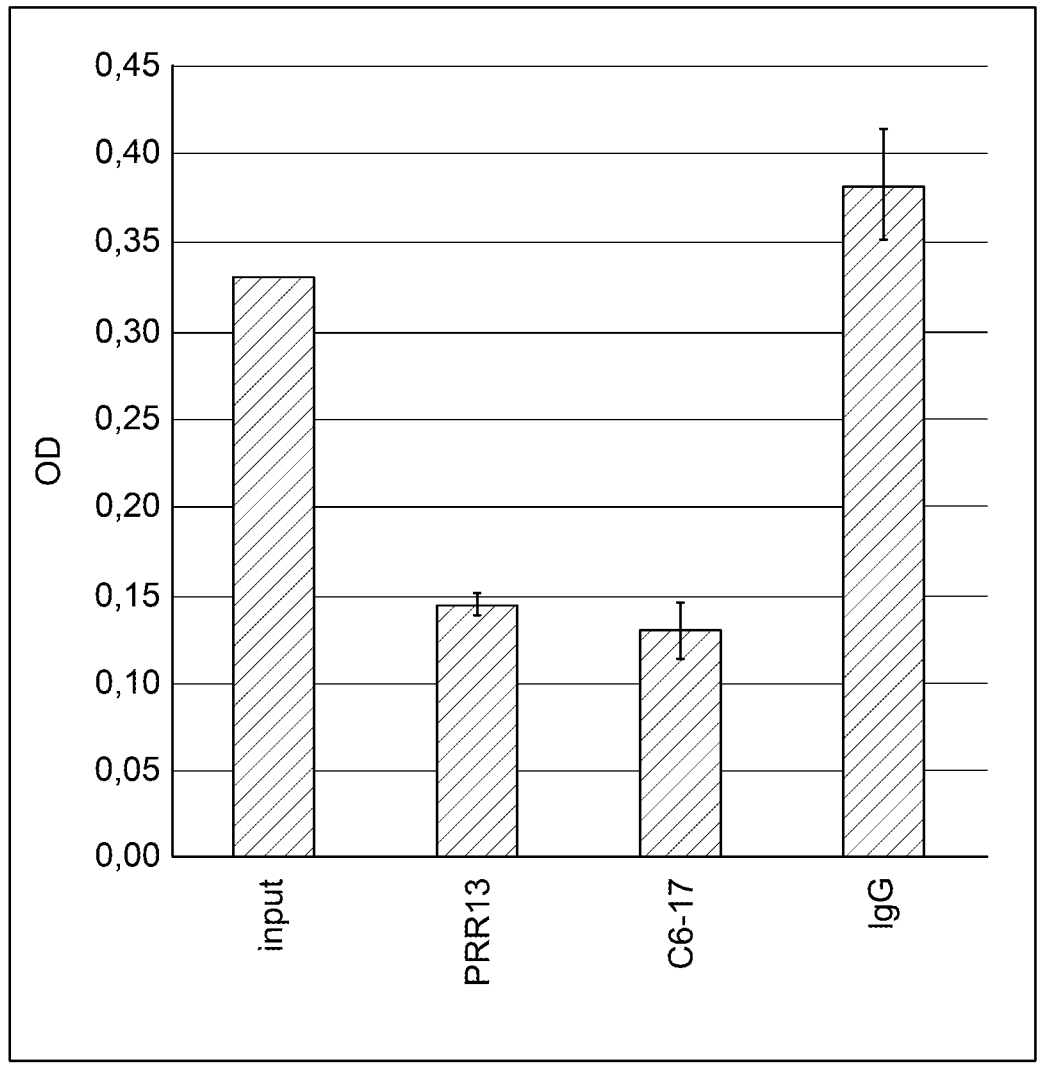
FIG. 18 shows specific depletion of recombinant Huntingtin recHTT61.0 from human serum using mABs PRR13 and C6-17 in comparison to isotype control antibody IgG.

In order to demonstrate that mAbs PPR13 and C6-17 can be utilized as specific adsorbers for therapeutic apheresis of plasma Huntingtin, excess recombinant Huntingtin recHTT610 was added to human sera from healthy donors and subsequently submitted to ex vivo depletion by biotin-immobilized mAB PRR13, C6-17 and control IgG, respectively. As shown in FIG. 18, monoclonal antibodies PRR13 and C6-17 but not IgG efficiently depleted excess Huntingtin from human plasma. These antibodies therefore provide convenient adsorbers for therapeutic apheresis for the treatment of Huntingtin. The usefulness of these antibodies for therapeutic apheresis treatment in Huntington's disease is supported by the fact that mAB PPR13 and C6-17 were generated by using p6773 and p7543 as immunization peptide. Peptides from these targeting regions are capable of inducing antibodies that reduce the Huntington's disease phenotype in transgenic animal models as shown in Example 2 and 0.3, respectively. In analogy corresponding mABs are expected to provide a similar benefit by depleting HTT as demonstrated in FIG. 18.

FIG. 18: Specific depletion of recombinant Huntingtin recHTT610 from human serum using mABs PRR13 and C6-17 in comparison to isotype control antibody IgG. As reflected by reduction of the Huntingtin signal in plasma (determined by protein ELISA such as in Example 1), these mAb's can efficiently adsorb and reduce Huntingtin as required for therapeutic apheresis. The graph represents the amount of Huntingtin signal (as OD; measured by protein capture ELISA) detected prior depletion (Input), after depletion by specific antibodies (mAB PRR13 and C6-17) and after depletion by an isotype control antibody (IgG).

Table 1: Preferred peptide uses (peptide name/peptide region/peptide sequence (C is for coupling to carrier protein; can be provided at N- or C-terminus of the peptide), except for p7564, p7541, p7552, p7562, p7563, p7567 or p7568, where a free C-terminal aspartic acid is required for the epitope); peptide list indicating name designations, mapping to protein region (region: Nter=N-terminus, polyQ=polyglutamine stretch, PR=poly proline rich region, Ex1=mapping to exon 1, C6=caspase cleavage 586 region) and amino acid sequences (single letter code; Nter>Cter; a=beta-alanine; b-biotin)

Figure 19:
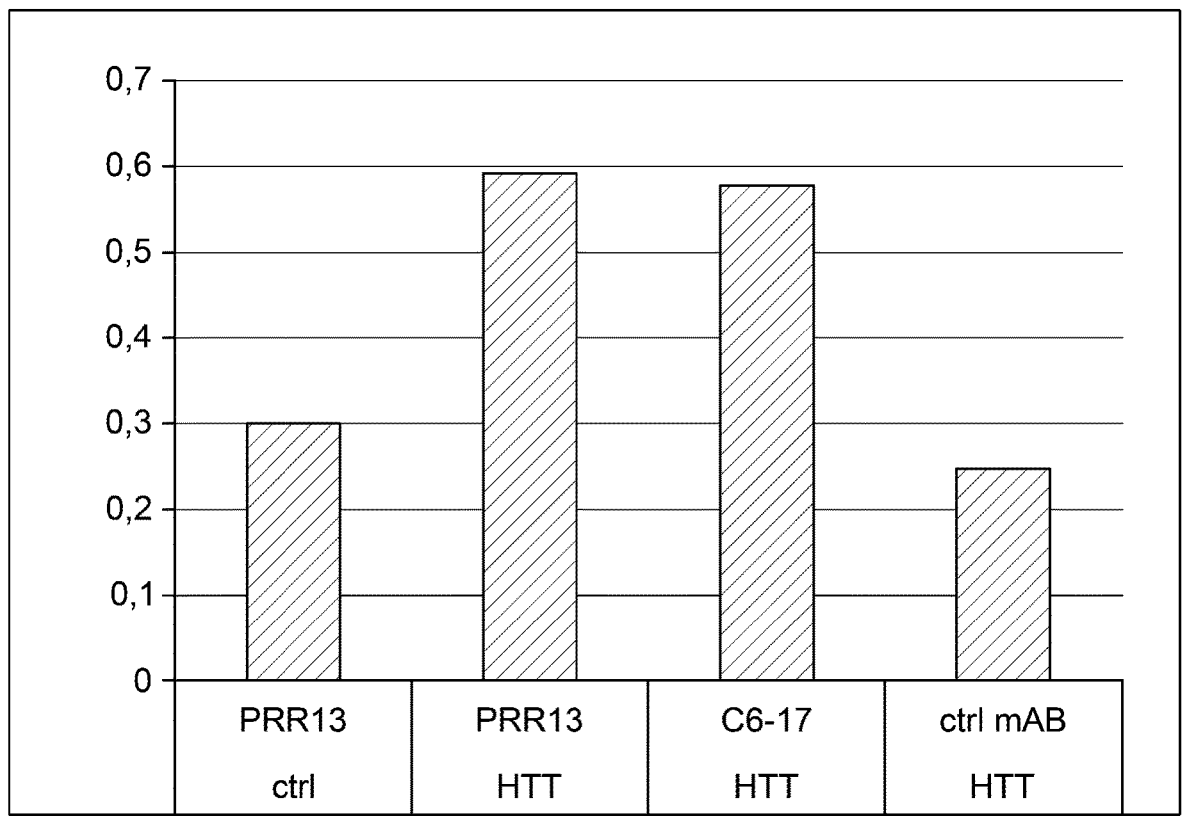
FIG. 19-21 show recognition capacity of the antibodies used according to the present invention.

Example 7—Use of mAB PRR13 or mAB C6-17 as Adsorbers for Therapeutic Apheresis Biotinylated anti HTT antibodies mAB PRR13, mAB C6-17 and an irrelevant control antibody ("ctrl mAB") were immobilized on magnetic streptavidin beads and incubated with 1:1 PBS diluted human serum spiked with cell extract from transiently transfected HEK cells expressing recombinant HTT610 (indicated by "HTT") or with control extract from non-transfected HEK cells (indicated "ctrl"). Adsorber beads coated by mAB PRR13 or mAB C6-17 showed recHTT capturing, respectively (FIG. 19; indicated "PPR13 and C6-17"; y-axis shows OD resulting from anti anti V5 detection of captured recHTT610 protein). Irrelevant CTRL extracts (ctrl) or beads coated by an irrelevant antibody (ctrl mAB) provided background controls. As a conclusion, this provides an example for the use of these antibodies as adsorber for HTT present in serum or other fluids as required for e.g. therapeutic apheresis.

Method: HTT Depletion

100 µg paramagnetic Streptavidin beads (Dynabeads T1, CatNr. 65601) were incubated in a buffer volume of 50 µl with 20 ng/µl biotinylated mABs for 1 h at RT. Human serum was diluted 1:4 with PBS and spiked with protein extracts from recHTT610 and mock transfected HEK293 cells at a final extract concentration of 50-100 ng/µl, prepared as in. Example 1. Biotinylated mAB's were coupled to streptavidin beads and subsequently incubated with recHTT610-extract containing serum o/n at RT. To confirm recHTT610 depletion efficacy, input serum (containing recHTT610), mock serum and recHTT610-depleted serum was using recHTT610 capture ELISA as in example 1. Rec HTT610 depletion of serum by antibody-coated beads was quantified using an on-beads ELISA setting as follows: To detect bound recHTT610, beads were washed stringently using a 50 mM Tris, 250 mM NaCl, 0.1% Tween buffer followed by incubation with a rabbit V5 antibody (1:5000).

Example 8—Use of Supplementary Example #1b: Monoclonal or Polyclonal Antibodies from the Present Invention Recognise Also Mutant HTT (mutHTT) Containing an Extended 82 Amino Acids Long Poly Q Stretch (mutHTT610 Q82)

Figure 20:
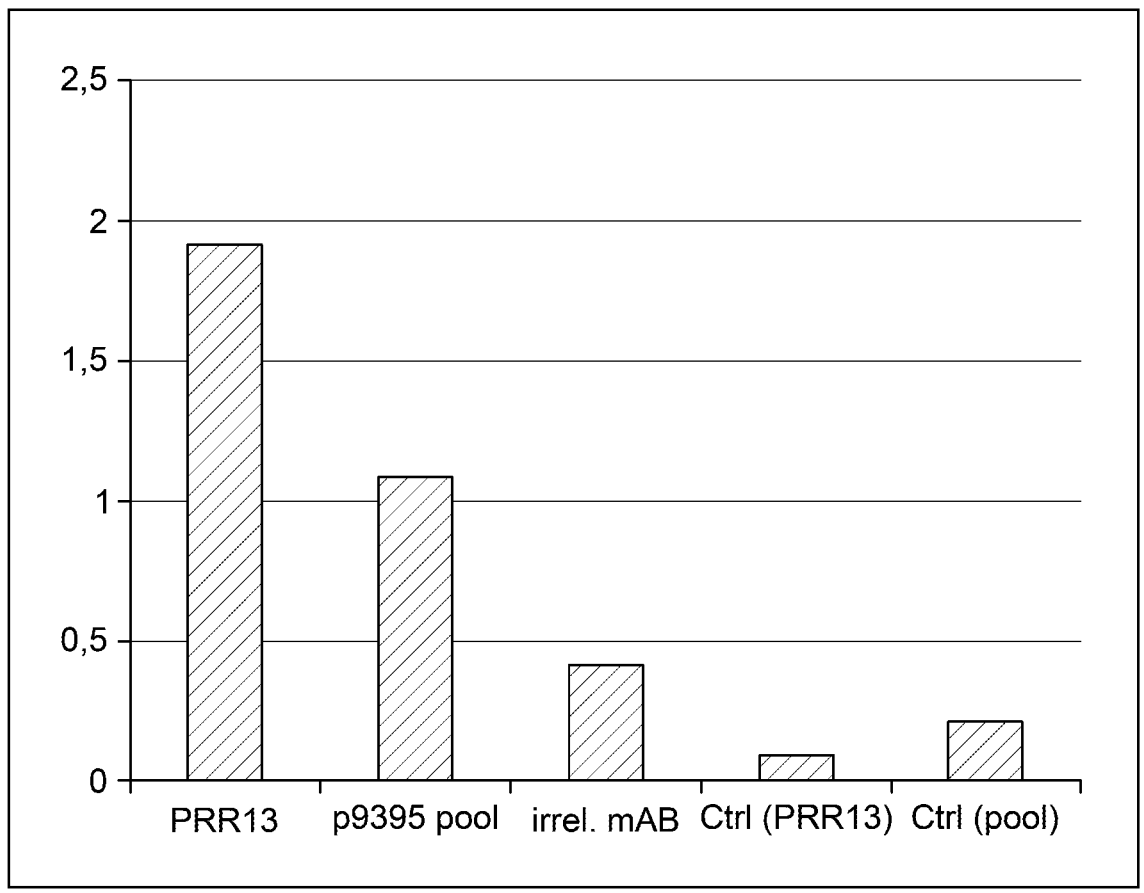

A supernatant derived from HEK cells transiently expressing recombinant mutHTT610 Q82 was directly coated on ELISA plates and subsequently incubated with mAB PRR13 (5 ng/µl), polyclonal p9395 serum mix (1:100 dilution; derived from 5 immunized animals) and an irrelevant mAB (5 ng/µl). Results are depicted in FIG. 20. The Y-axis shows OD values obtained from ELISA using mAB PRR13, pooled serum from five p9395-immunized animals and irrelevant mAB, as indicated, whereby the same ELISA protocol as in Example 1 was applied. To determine the background signals of the ELISA assay, mAB PRR13 and pooled p9395 serum was incubated with 1.25 ng/ml cell extract as indicated.

Figure 21:
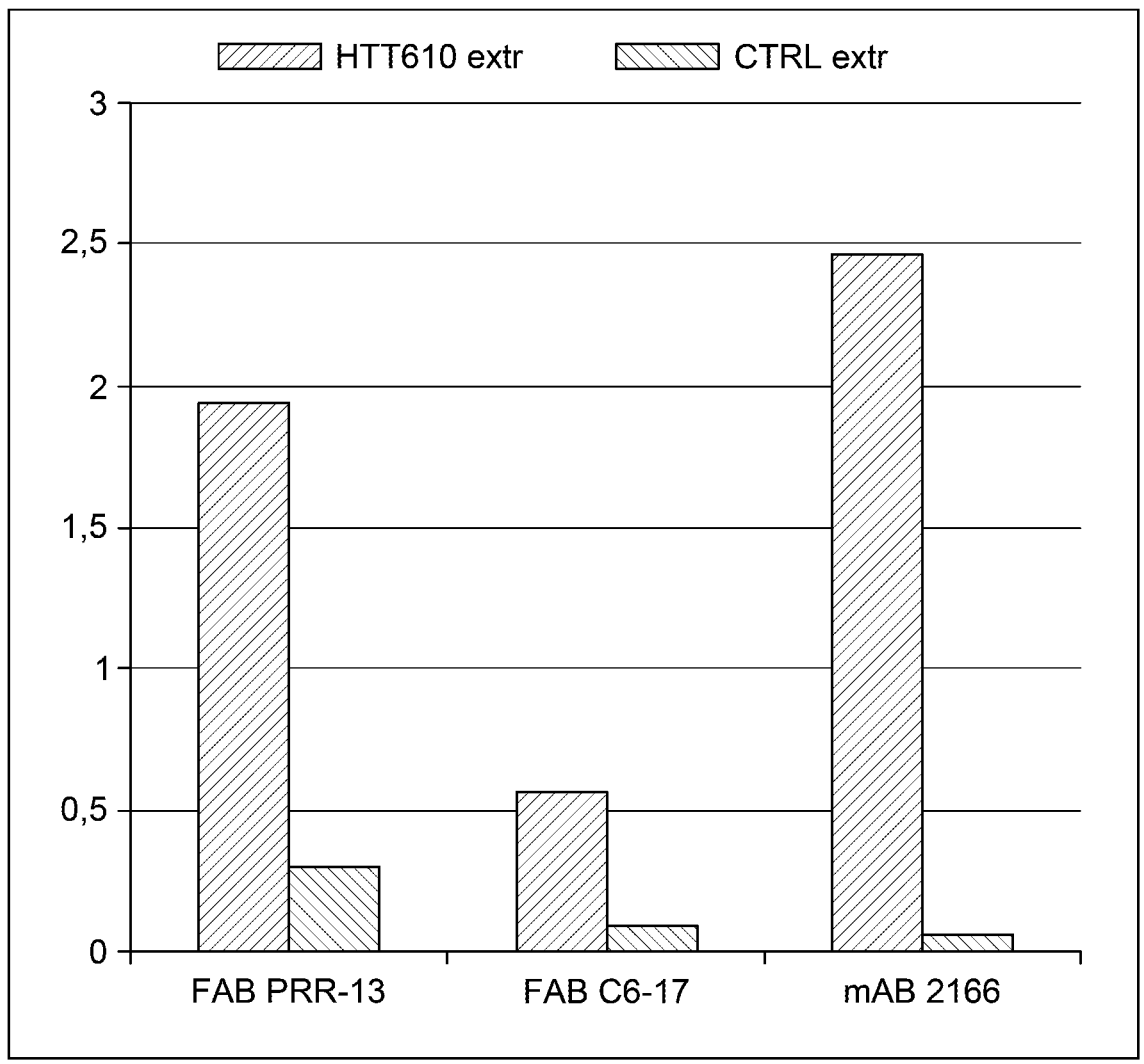

Example 9: Derivatisation of Recombinant Fab's Based on the Sequence Information of mAB PRR13 and C6-17, Respectively PRR13 FAB and C6-17 FAB were transiently transfected in to HEK cells and tested by HTT capture ELISA using cellular extracts from HTT610 transfected HEK cells as shown above. mAB 2166 (1:2000) was used as positive control antibody. The results are depicted in FIG. 21. Binding signals (OD values on y-axis; light grey bars) for FAB PRR13 and FAB C6-17 are shown in direct comparison with anti HTT reference antibody mAB 2166 as indicated on the x-axis. Background signals were determined using control extracts (CTRL extr) derived from non-transfected HEK cells are indicated by dark grey bars. This exemplifies that a derivative of either mABs can also be used as adsorbers.

Method—Fab Expression:

Light chains and heavy chains (w/o the hinge region of IgG) of antibodies PRR13 and C6-17 were cloned into a CMV driven gene expression vector in order to obtain recombinant FAB in the supernatant (SN). SNs were collected after 24 to 48 h post transfection and the expression and binding functionality of these constructs was confirmed by peptide ELISA and rec HTT610 ELISA.

Example 10—Antibody Humanisation a) Antibody humanization of original antibodies PRR13 and hC6-17, respectively was performed as follows: Prototypic frameworks for heavy and light chain variable regions were used for the generation of series hPRR13-1 to -16 and hC6-17-1 to -16, respectively. Series included prototypic variants containing modifications at one or several amino acid positions in the heavy (designated Framework H) and/or light chain (designated Framework L) as indicated in FIG. 22. Numbers reflect amino acid positions within the framework regions indicated for the humanized antibodies below.

hPRR13 series light chain variable region
(SEQ ID No. 95)
[EIVLTQSPSSLSASVGDRVTITCTASSSVTSSYLHWYQQKPGKAPKLLI

YSTSNLASGVPSRFSGSGSGTDFTFTISSLQPEDIATYYCHQYRRPPRTF

GGGTKLEIKR]

hPRR13 heavy chain variable region
(SEQ ID No. 96)
[EVQLVESGPEVKKPGATVKISCKVSGYTFTDFYMKWVQQAPGRGLEWMG

DIDPKNGDTFYNQKFKGRVTMTADTSTGTAYMQLSSLTSEDTAVYFCASY

YGYTMDYWGQGTTVTVAS];

hC6-17 light chain variable region
(SEQ ID No. 97)
[DIVMTQSPDSLAVSLGERATINCKSSQSLLNSRTRKNYLAWYQQKPGQP

PKLLIYWASTRESGVPDRFSGSGSGTDFTLTISSLQAEDVAVYYCKQSYN

LLTFGGGTKLEIK];

hC6-17 heavy chain variable region
(SEQ ID No. 98)
[QVQLVQSGAEVKKPGASVKVSCKASGYTFTEYTMHWVRQAPGRGLEWMG

GINPNNGGTRYNQKFKGRVTMTRDTSIRTAYVELSRLTSDDTAVYYCASL

DGRDYWGQGTLVTVSS]

Figure 23:
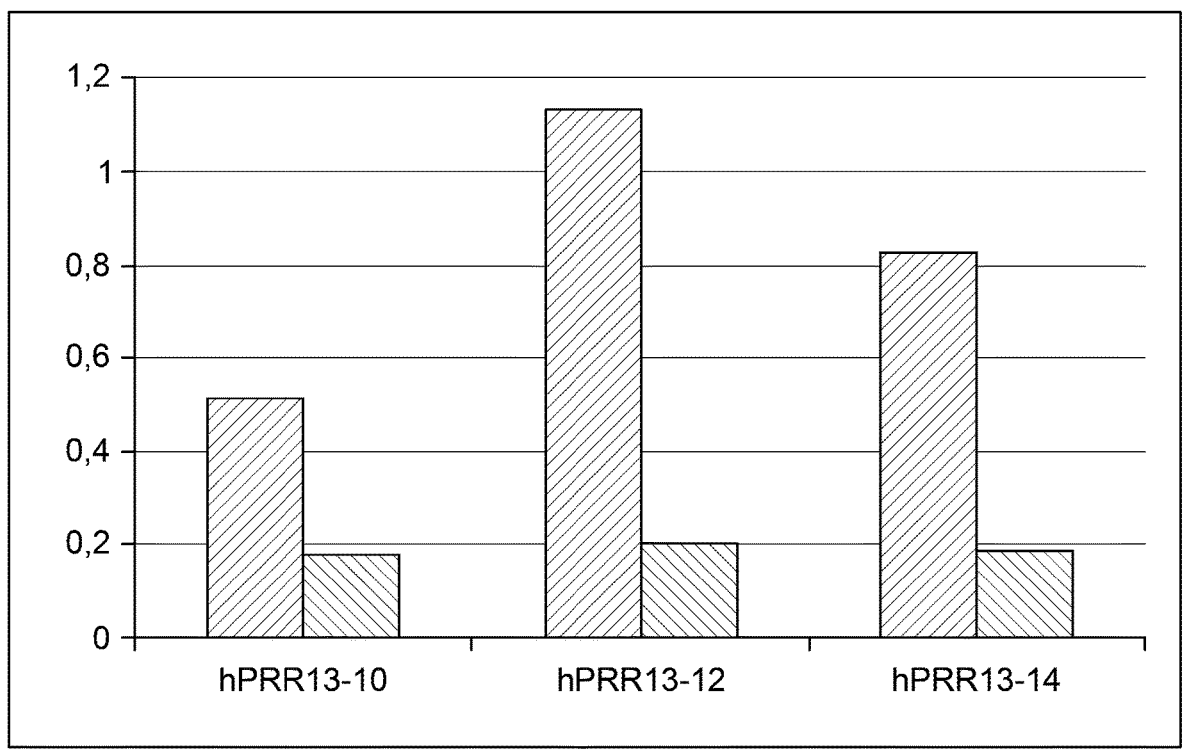

Methods: Human vLC and vHC sequences were synthesized and cloned into the expression vector pFUSE2ss CLg-hk (EcoRI/NheI) and pFUSEss CHIg-hG1 (EcrRI/BsiWI). Cloning procedures were performed according to standard molecular biology procedures essentially as indicated by manufacturers including restriction digestions and ligation reactions (NEB Quick ligase kit; CatNr. M2200L), bacterial transformation followed by clone selection and analysis. DNA fragment preparations from agarose gels were performed using standard DNA purification kits (Quiagen; CatNr. 27106). HEK293 freestyle cells (Invitrogen; CatNr. R790-07) were grown in medium as indicated by the manufacturer and transiently co-transfected with different combinations of hu AB heavy and light chain vectors as indicated in the table. Cell culture SNs were collected 24-48 h after transfection and concentrated 1:30 followed by buffer exchange (PBS) using Spin-X UF500 tubes (Corning, CLS431478). Concentrated human antibody-SNs were tested by in vitro peptide and protein binding using ELISA (as in Example 1). Further characterization was performed as indicated throughout this Example 9.

b) As an example, recognition of recHTT610 protein by humanized mAB PRR13 derivatives hPRR13-10, hPRR13-12 and hPRR13-14 (light grey bars) containing framework mutations as indicated in a) (see FIG. 22) can be demonstrated by protein ELISA (performed as in Example 1; see FIG. 23, y-axis reflects rec Htt610 binding activity[OD]) in comparison to a control extract (dark grey bars).

| | | | SEQ ID No. | | | |
|---|---|---|---|---|---|---|
| P6773 | PRR | LPQPPPQAQPLLPQPQPC | 103 | ++ active vacc. | mAB generation | |
| p7564 | C6 | CPSDSSEIVLD | 104 | ++ active vacc. | mAB generation | |
| p7543 | C6 | GTDNQYLGLQIGC | 105 | ++ active vacc. | mAB generation | C6 inhibition |
| p6771 | PRR | LPQPPPQAQPLLPC | 106 | ++ active vacc. | mAB generation | |
| p8346 | Ex1 | CGPAVAEEPLHRP | 107 | ++ active vacc. | mAB generation | |
| p8855 | C6 | SDSSEIVLDGTDC | 108 | ++ active vacc. | | C6 inhibition |
| p8858 | C6 | EIVLDGTDNQYLC | 109 | ++ active vacc. | | C6 inhibition |
| p8859 | C6 | IVLDGTDNQYLGC | 110 | ++ active vacc. | | C6 inhibition |
| p8860 | C6 | VLDGTDNQYLGLC | 111 | ++ active vacc. | | C6 inhibition |
| p8861 | C6 | LDGTDNQYLGLQC | 112 | ++ active vacc. | | C6 inhibition |
| p8862 | C6 | DGTDNQYLGLQIGC | 113 | ++ active vacc. | | C6 inhibition |
| p8869 | C6 | CTDNQYLGLQIGQ | 114 | ++ active vacc. | | C6 inhibition |
| p8868 | C6 | CGTDNQYLGLQIG | 115 | + active vacc. | | C6 inhibition |

-continued

| | | | SEQ ID No. | | |
|---|---|---|---|---|---|
| p8870 | C6 | CDNQYLGLQIGQP | 116 | + active vacc. | C6 inhibition |
| p8871 | C6 | CNQYLGLQIGQPQ | 117 | + active vacc. | C6 inhibition |
| p6772 | PRR | CPQLPQPPPQAQPLLP | 118 | + active vacc. | C6 inhibition |
| p8864 | C6 | TDNQYLGLQIGQC | 119 | ++ active vacc. | |
| p8865 | C6 | DNQYLGLQIGQPC | 120 | ++ active vacc. | |
| p6775 | PRR | PPPQLPQPPPQAQPLLPQPQPaC | 121 | ++ active vacc. | |
| p8854 | C6 | PSDSSEIVLDGTC | 122 | + active vacc. | |
| p8856 | C6 | DSSEIVLDGTDNC | 123 | + active vacc. | |
| p8857 | C6 | SEIVLDGTDNQYC | 124 | + active vacc. | |
| p8866 | C6 | NQYLGLQIGQPQC | 125 | + active vacc. | |
| p8867 | C6 | QYLGLQIGQPQDC | 126 | + active vacc. | |
| p6763 | Nter | CaMATLEKLMKAFESLKSFQ | 127 | | |
| p6764 | Nter | CaKLMKAFESLKSFQ | 128 | | |
| p6765 | polyQ | CEEQQPQQQQQQQ | 129 | | |
| p6768 | polyQ | QQQQQQPPPPPPPPaKKKC | 130 | | |
| p7541 | C6 | CSEIVLD | 131 | | |
| p7552 | C6 | CSSEIVLD | 132 | | |
| p7562 | C | CDSSEIVLD | 133 | | |
| p7563 | C6 | CSDSSEIVLD | 134 | | |
| p7565 | C6 | CSEIVLDGT | 135 | | |
| p7567 | C6 | CEIVLD | 136 | | |
| p7568 | C6 | CIVLD | 137 | | |
| p7605 | C6 | CSEIVL | 138 | | |
| p6776 | C6 | CSEIVLDGTDNQYL | 139 | ++ active vacc. | C6 inhibition |
| p6777 | C6 | CSDSSEIVLDGTDN | 140 | ++ active vacc. | C6 inhibition |
| p6776b | C6 | SEIVLDGTDNQYLC | 141 | | |
| p7752 | C6 | CAEIVLDGTDNQYL | 142 | | |
| p7753 | C6 | CSAIVLDGTDNQYL | 143 | | |
| p7754 | C6 | CSEAVLDGTDNQYL | 144 | | |
| p7755 | C6 | CSEIALDGTDNQYL | 145 | | |
| p7756 | C6 | CSEIVADGTDNQYL | 146 | | |
| p7757 | C6 | CSEIVLAGTDNQYL | 147 | | |
| p7758 | C6 | CSEIVLDATDNQYL | 148 | | |
| p7745 | C6 | CSEIVLDGADNQYL | 149 | | |
| p7746 | C6 | CSEIVLDGTANQYL | 150 | | |
| p7747 | C6 | CSEIVLDGTDAQYL | 151 | | |
| p7748 | C6 | CSEIVLDGTDNAYL | 152 | | |
| p7749 | C6 | CSEIVLDGTDNQAL | 153 | | |

| | | | SEQ ID No. |
|---|---|---|---|
| p7750 | C6 | CSEIVLDGTDNQYA | 154 |

Especially preferred for active vaccination ("++ active vacc.")
Preferred for active vaccination ("+ active vacc.")
Preferred for mAB generation ("mAB generation")
Preferred for C6 cleavage inhibition ("C6 inhibition")

LITERATURE

Bard et al., 2014, Journal of Biomolecular Screening, Volume 19(2), 191-204
Butler et al., 2012, Progress in Neurobiology, Volume 97(2): 190-204
Davidson, 2012, Molecular Therapy, Volume 20(10): 1838
Ellrichmann et al., 2013, Clin Dev Immunol., 2013; 2013: 541259
Graham et al., 2010, J Neurosci., Volume 30(45):15019-29
Ko et al., 2001, Brain Research Bulletin, Volume 56(3/4): 319-329
Liu, 2007, Journal of the American Society for Mass Spectrometry. Volume 18(7):1249-64
Mandler et al.; Acta Neuropathologica 127 (2014): 861-879
Messer & Joshi, 2013, Neurotherapeutics, Volume 10: 447-458
Modregger et al., 2002, Human Molecular Genetics, Volume 11 (21):2547-58
Novak & Tabrizi, 2011, International Review of Neurobiology, Volume 98: 297-323
O'Hagan & Valiante, 2003, Nature Reviews Drug Discovery, Volume 2(9): 727-35
Singh & O'Hagan, 1999, Nature Biotechnology, Volume 17 (11): 1075-81
Southwell et al., 2011, PloS ONE, Volume 6(1): 16676
Stadler et al.; Angewandte Chemie International Edition England 2008; Vol 47 (37):7132-5 Tezel et al., 2012, Investigative Ophthalmology & Visual Science Volume 53(13): 8222-31
Träger et al., 2014, Brain, Volume 137(3):819-33
Warby et al., 2008, Human Molecular Genetics, Volume 17(15): 2390-2404
Weiss et al., Analytical Biochemistry 2009; Vol 395(1):8-15
Weiss et al., 2012, The Journal of Clinical Investigation, Volume 122 (10): 3731-3736
Weiss et al. 2014, 9th Annual Huntington's Disease Therapeutics Conference (CHDI); Palm Springs USA, Abstract.
Wong et al. 2014; 9th Annual Huntington's Disease Therapeutics Conference (CHDI); Palm Springs USA, Abstract.
Yu et al., 2014, Trends in Pharmacological Sciences, Volume 35 (2): 53-62
Zhang et al.; Current Protocols in Immunology 2008; Chapter: Unit-14.1
Zheng & Diamond, 2012, Progress in Molecular Biology and Translational Science, Volume 107: 189-214

The invention claimed is:

1. A monoclonal antibody having a binding domain that binds to a peptide of the Huntingtin (HTT) protein having the sequence of p7543 (SEQ ID No. 3) and
- wherein the monoclonal antibody comprises a heavy chain variable region CDR1 comprising GYTFTEYT (SEQ ID No. 66), a heavy chain variable region CDR2 comprising INPNNGGT (SEQ ID No. 67), a heavy chain variable region CDR3 comprising ASLDGRDY (SEQ ID No. 68), a light chain variable region CDR1 comprising QSLLNSRTRKNY SEQ ID No. 69), a light chain variable region CDR2 comprising WAS$\underline{X}$ (SEQ ID No. 70) and a light chain variable region comprising KQSYNLLT (SEQ ID No. 71); or
- wherein the monoclonal antibody comprises a light chain variable region comprising SEQ ID NO:97 and a heavy chain variable region comprising SEQ ID NO:98.

2. The monoclonal antibody according to claim 1, which comprises a heavy chain variable region CDR1 comprising GYTFTEYT (SEQ ID No. 66), a heavy chain variable region CDR2 comprising INPNNGGT (SEQ ID No. 67), a heavy chain variable region CDR3 comprising ASLDGRDY (SEQ ID No. 68), a light chain variable region CDR1 comprising QSLLNSRTRKNY SEQ ID No. 69), a light chain variable region CDR2 comprising WAS$\underline{X}$ (SEQ ID No. 70) and a light chain variable region comprising KQSYNLLT (SEQ ID No. 71).

3. The monoclonal antibody according to claim 1, which comprises a light chain variable region comprising SEQ ID NO:97 and a heavy chain variable region comprising SEQ ID NO:98.

* * * * *

SEQUENCE LISTING

```
<160> NUMBER OF SEQ ID NOS: 154

<210> SEQ ID NO 1
<211> LENGTH: 18
<212> TYPE: PRT
<213> ORGANISM: Artificial Sequence
<220> FEATURE:
<223> OTHER INFORMATION: Huntingtin peptide

<400> SEQUENCE: 1

Leu Pro Gln Pro Pro Pro Gln Ala Gln Pro Leu Leu Pro Gln Pro Gln
1               5                   10                  15

Pro Cys

<210> SEQ ID NO 2
<211> LENGTH: 11
<212> TYPE: PRT
<213> ORGANISM: Artificial Sequence
<220> FEATURE:
<223> OTHER INFORMATION: Huntingtin peptide

<400> SEQUENCE: 2

Cys Pro Ser Asp Ser Ser Glu Ile Val Leu Asp
1               5                   10

<210> SEQ ID NO 3
<211> LENGTH: 13
<212> TYPE: PRT
<213> ORGANISM: Artificial Sequence
<220> FEATURE:
```

```
<223> OTHER INFORMATION: Huntingtin peptide

<400> SEQUENCE: 3

Gly Thr Asp Asn Gln Tyr Leu Gly Leu Gln Ile Gly Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 4

Leu Pro Gln Pro Pro Pro Gln Ala Gln Pro Leu Leu Pro Cys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 5

Cys Gly Pro Ala Val Ala Glu Glu Pro Leu His Arg Pro
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 6

Ser Asp Ser Ser Glu Ile Val Leu Asp Gly Thr Asp Cys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 7

Glu Ile Val Leu Asp Gly Thr Asp Asn Gln Tyr Leu Cys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 8

Ile Val Leu Asp Gly Thr Asp Asn Gln Tyr Leu Gly Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Huntingtin peptide
```

<400> SEQUENCE: 9

Val Leu Asp Gly Thr Asp Asn Gln Tyr Leu Gly Leu Cys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 10

Leu Asp Gly Thr Asp Asn Gln Tyr Leu Gly Leu Gln Cys
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 11

Asp Gly Thr Asp Asn Gln Tyr Leu Gly Leu Gln Ile Gly Cys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 12

Cys Thr Asp Asn Gln Tyr Leu Gly Leu Gln Ile Gly Gln
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 13

Cys Gly Thr Asp Asn Gln Tyr Leu Gly Leu Gln Ile Gly
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 14

Cys Asp Asn Gln Tyr Leu Gly Leu Gln Ile Gly Gln Pro
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Huntingtin peptide

```
<400> SEQUENCE: 15

Cys Asn Gln Tyr Leu Gly Leu Gln Ile Gly Gln Pro Gln
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Huntingtin peptide

<400> SEQUENCE: 16

Cys Pro Gln Leu Pro Gln Pro Pro Pro Gln Ala Gln Pro Leu Leu Pro
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 17

Thr Asp Asn Gln Tyr Leu Gly Leu Gln Ile Gly Gln Cys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 18

Asp Asn Gln Tyr Leu Gly Leu Gln Ile Gly Gln Pro Cys
1               5                   10

<210> SEQ ID NO 19
<211> LENGTH: 23
<212> TYPE: PRT
<213> ORGANISM: Artificial Sequence
<220> FEATURE:
<223> OTHER INFORMATION: Huntingtin peptide
<220> FEATURE:
<221> NAME/KEY: misc_feature
<222> LOCATION: (22)..(22)
<223> OTHER INFORMATION: Xaa can be any naturally occurring amino acid

<400> SEQUENCE: 19

Pro Pro Pro Gln Leu Pro Gln Pro Pro Pro Gln Ala Gln Pro Leu Leu
1               5                   10                  15

Pro Gln Pro Gln Pro Xaa Cys
                20

<210> SEQ ID NO 20
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 20

Pro Ser Asp Ser Ser Glu Ile Val Leu Asp Gly Thr Cys
1               5                   10

<210> SEQ ID NO 21
```

```
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 21

Asp Ser Ser Glu Ile Val Leu Asp Gly Thr Asp Asn Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 22

Ser Glu Ile Val Leu Asp Gly Thr Asp Asn Gln Tyr Cys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 23

Asn Gln Tyr Leu Gly Leu Gln Ile Gly Gln Pro Gln Cys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 24

Gln Tyr Leu Gly Leu Gln Ile Gly Gln Pro Gln Asp Cys
1               5                   10

<210> SEQ ID NO 25
<211> LENGTH: 20
<212> TYPE: PRT
<213> ORGANISM: Artificial Sequence
<220> FEATURE:
<223> OTHER INFORMATION: Huntingtin peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 25

Cys Xaa Met Ala Thr Leu Glu Lys Leu Met Lys Ala Phe Glu Ser Leu
1               5                   10                  15

Lys Ser Phe Gln
            20

<210> SEQ ID NO 26
<211> LENGTH: 15
<212> TYPE: PRT
<213> ORGANISM: Artificial Sequence
<220> FEATURE:
<223> OTHER INFORMATION: Huntingtin peptide
<220> FEATURE:
<221> NAME/KEY: misc_feature
```

```
<222> LOCATION: (2)..(2)
<223> OTHER INFORMATION: Xaa can be any naturally occurring amino acid

<400> SEQUENCE: 26

Cys Xaa Lys Leu Met Lys Ala Phe Glu Ser Leu Lys Ser Phe Gln
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: Huntingtin peptide

<400> SEQUENCE: 27

Cys Glu Glu Gln Gln Arg Gln Gln Gln Gln Gln Gln
1               5                   10

<210> SEQ ID NO 28
<211> LENGTH: 19
<212> TYPE: PRT
<213> ORGANISM: Artificial Sequence
<220> FEATURE:
<223> OTHER INFORMATION: Huntingtin peptide
<220> FEATURE:
<221> NAME/KEY: MOD_RES
<222> LOCATION: (15)..(15)
<223> OTHER INFORMATION: bAla

<400> SEQUENCE: 28

Gln Gln Gln Gln Gln Gln Pro Pro Pro Pro Pro Pro Pro Xaa Lys
1               5                   10                  15

Lys Lys Cys

<210> SEQ ID NO 29
<211> LENGTH: 7
<212> TYPE: PRT
<213> ORGANISM: Artificial Sequence
<220> FEATURE:
<223> OTHER INFORMATION: Huntingtin peptide

<400> SEQUENCE: 29

Cys Ser Glu Ile Val Leu Asp
1               5

<210> SEQ ID NO 30
<211> LENGTH: 8
<212> TYPE: PRT
<213> ORGANISM: Artificial Sequence
<220> FEATURE:
<223> OTHER INFORMATION: Huntingtin peptide

<400> SEQUENCE: 30

Cys Ser Ser Glu Ile Val Leu Asp
1               5

<210> SEQ ID NO 31
<211> LENGTH: 9
<212> TYPE: PRT
<213> ORGANISM: Artificial Sequence
<220> FEATURE:
<223> OTHER INFORMATION: Huntingtin peptide

<400> SEQUENCE: 31

Cys Asp Ser Ser Glu Ile Val Leu Asp
1               5
```

<210> SEQ ID NO 32
<211> LENGTH: 10
<212> TYPE: PRT
<213> ORGANISM: Artificial Sequence
<220> FEATURE:
<223> OTHER INFORMATION: Huntingtin peptide

<400> SEQUENCE: 32

Cys Ser Asp Ser Ser Glu Ile Val Leu Asp
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Huntingtin peptide

<400> SEQUENCE: 33

Cys Glu Ile Val Leu Asp
1               5

<210> SEQ ID NO 34
<211> LENGTH: 5
<212> TYPE: PRT
<213> ORGANISM: Artificial Sequence
<220> FEATURE:
<223> OTHER INFORMATION: Huntingtin peptide

<400> SEQUENCE: 34

Cys Ile Val Leu Asp
1               5

<210> SEQ ID NO 35
<211> LENGTH: 6
<212> TYPE: PRT
<213> ORGANISM: Artificial Sequence
<220> FEATURE:
<223> OTHER INFORMATION: Huntingtin peptide

<400> SEQUENCE: 35

Cys Ser Glu Ile Val Leu
1               5

<210> SEQ ID NO 36
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 36

Cys Ser Glu Ile Val Leu Asp Gly Thr Asp Asn Gln Tyr Leu
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 37

Cys Ser Asp Ser Ser Glu Ile Val Leu Asp Gly Thr Asp Asn
1               5                   10

```
<210> SEQ ID NO 38
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 38

Ser Glu Ile Val Leu Asp Gly Thr Asp Asn Gln Tyr Leu Cys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 39

Cys Ala Glu Ile Val Leu Asp Gly Thr Asp Asn Gln Tyr Leu
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 40

Cys Ser Ala Ile Val Leu Asp Gly Thr Asp Asn Gln Tyr Leu
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 41

Cys Ser Glu Ala Val Leu Asp Gly Thr Asp Asn Gln Tyr Leu
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 42

Cys Ser Glu Ile Ala Leu Asp Gly Thr Asp Asn Gln Tyr Leu
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 43

Cys Ser Glu Ile Val Ala Asp Gly Thr Asp Asn Gln Tyr Leu
1               5                   10

<210> SEQ ID NO 44
```

```
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 44

Cys Ser Glu Ile Val Leu Ala Gly Thr Asp Asn Gln Tyr Leu
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 45

Cys Ser Glu Ile Val Leu Asp Ala Thr Asp Asn Gln Tyr Leu
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 46

Cys Ser Glu Ile Val Leu Asp Gly Ala Asp Asn Gln Tyr Leu
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 47

Cys Ser Glu Ile Val Leu Asp Gly Thr Ala Asn Gln Tyr Leu
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 48

Cys Ser Glu Ile Val Leu Asp Gly Thr Asp Ala Gln Tyr Leu
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 49

Cys Ser Glu Ile Val Leu Asp Gly Thr Asp Asn Ala Tyr Leu
1               5                   10

<210> SEQ ID NO 50
<211> LENGTH: 14
```

```
<212> TYPE: PRT
<213> ORGANISM: Artificial Sequence
<220> FEATURE:
<223> OTHER INFORMATION: Huntingtin peptide

<400> SEQUENCE: 50

Cys Ser Glu Ile Val Leu Asp Gly Thr Asp Asn Gln Ala Leu
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Huntingtin peptide

<400> SEQUENCE: 51

Cys Ser Glu Ile Val Leu Asp Gly Thr Asp Asn Gln Tyr Ala
1               5                   10

<210> SEQ ID NO 52
<211> LENGTH: 43
<212> TYPE: PRT
<213> ORGANISM: Artificial Sequence
<220> FEATURE:
<223> OTHER INFORMATION: Huntingtin peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 52

Xaa Gly Gly Gly Asp Tyr Lys Asp Asp Asp Lys Gly Ala Val Thr
1               5                   10                  15

Pro Ser Asp Ser Ser Glu Ile Val Leu Asp Gly Thr Asp Asn Gln Tyr
            20                  25                  30

Leu Gly Leu Gln Ile Gly Gln Pro Gln Asp Gly
        35                  40

<210> SEQ ID NO 53
<211> LENGTH: 35
<212> TYPE: PRT
<213> ORGANISM: Artificial Sequence
<220> FEATURE:
<223> OTHER INFORMATION: Huntingtin peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 53

Xaa Gly Gly Gly Asp Tyr Lys Asp Asp Asp Lys Gly Pro Pro Pro
1               5                   10                  15

Gln Leu Pro Gln Pro Pro Pro Gln Ala Gln Pro Leu Leu Pro Gln Pro
            20                  25                  30

Gln Pro Gly
        35

<210> SEQ ID NO 54
<211> LENGTH: 8
<212> TYPE: PRT
<213> ORGANISM: Artificial Sequence
<220> FEATURE:
<223> OTHER INFORMATION: antibody sequence

<400> SEQUENCE: 54
```

```
Gly Tyr Ser Phe Thr Asp Phe Tyr
1               5

<210> SEQ ID NO 55
<211> LENGTH: 8
<212> TYPE: PRT
<213> ORGANISM: Artificial Sequence
<220> FEATURE:
<223> OTHER INFORMATION: antibody sequence

<400> SEQUENCE: 55

Ile Asp Pro Lys Asn Gly Asp Thr
1               5

<210> SEQ ID NO 56
<211> LENGTH: 10
<212> TYPE: PRT
<213> ORGANISM: Artificial Sequence
<220> FEATURE:
<223> OTHER INFORMATION: antibody sequence

<400> SEQUENCE: 56

Ala Thr Tyr Tyr Gly Tyr Thr Met Asp Tyr
1               5                   10

<210> SEQ ID NO 57
<211> LENGTH: 7
<212> TYPE: PRT
<213> ORGANISM: Artificial Sequence
<220> FEATURE:
<223> OTHER INFORMATION: antibody sequence

<400> SEQUENCE: 57

Ser Ser Val Thr Ser Ser Tyr
1               5

<210> SEQ ID NO 58
<211> LENGTH: 4
<212> TYPE: PRT
<213> ORGANISM: Artificial Sequence
<220> FEATURE:
<223> OTHER INFORMATION: antibody sequence
<220> FEATURE:
<221> NAME/KEY: MOD_RES
<222> LOCATION: (4)..(4)

<400> SEQUENCE: 58

Ser Thr Ser Xaa
1

<210> SEQ ID NO 59
<211> LENGTH: 9
<212> TYPE: PRT
<213> ORGANISM: Artificial Sequence
<220> FEATURE:
<223> OTHER INFORMATION: antibody sequence

<400> SEQUENCE: 59

His Gln Tyr Arg Arg Pro Pro Arg Thr
1               5

<210> SEQ ID NO 60
<211> LENGTH: 146
<212> TYPE: PRT
<213> ORGANISM: Artificial Sequence
<220> FEATURE:
<223> OTHER INFORMATION: antibody sequence
```

<400> SEQUENCE: 60

Met Gly Trp Ser Cys Ile Met Leu Phe Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Thr Ser Gly Tyr Thr Phe
        35                  40                  45

Thr Glu Tyr Thr Met His Trp Val Lys Gln Ser His Gly Lys Ser Leu
    50                  55                  60

Glu Trp Ile Gly Gly Ile Asn Pro Asn Asn Gly Gly Thr Arg Tyr Asn
65                  70                  75                  80

Gln Lys Phe Lys Gly Lys Ala Thr Leu Thr Val Asp Arg Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Ser Leu Asp Gly Arg Asp Tyr Trp Gly Gln Gly Thr
        115                 120                 125

Thr Leu Thr Val Ser Ser Ala Lys Thr Thr Ala Pro Ser Val Phe Pro
    130                 135                 140

Leu Ala
145

<210> SEQ ID NO 61
<211> LENGTH: 162
<212> TYPE: PRT
<213> ORGANISM: Artificial Sequence
<220> FEATURE:
<223> OTHER INFORMATION: antibody sequence

<400> SEQUENCE: 61

Met Val Leu Met Leu Leu Leu Trp Val Ser Gly Thr Cys Gly Asp
1               5                   10                  15

Ile Val Met Ser Gln Ser Pro Ser Ser Leu Ala Val Ser Ala Gly Glu
            20                  25                  30

Lys Val Thr Met Ser Cys Lys Ser Ser Gln Ser Leu Leu Asn Ser Arg
        35                  40                  45

Thr Arg Lys Asn Tyr Leu Ala Trp Tyr Gln Gln Lys Pro Gly Gln Ser
    50                  55                  60

Pro Lys Leu Leu Ile Tyr Trp Ala Ser Thr Arg Glu Ser Gly Val Pro
65                  70                  75                  80

Asp Arg Phe Thr Gly Ser Gly Ser Gly Thr Asp Phe Thr Leu Thr Ile
                85                  90                  95

Ser Ser Val Gln Ala Glu Asp Leu Ala Val Tyr Ser Cys Lys Gln Ser
            100                 105                 110

Tyr Asn Leu Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys

<210> SEQ ID NO 62
<211> LENGTH: 169
<212> TYPE: PRT
<213> ORGANISM: Artificial Sequence

```
<220> FEATURE:
<223> OTHER INFORMATION: antibody sequence

<400> SEQUENCE: 62

Met Gly Trp Ser Trp Val Met Leu Phe Leu Leu Ser Gly Thr Gly Gly
1               5                   10                  15

Val Leu Ser Glu Val Gln Leu Gln Gln Ser Ala Pro Glu Leu Val Lys
            20                  25                  30

Pro Gly Ala Ser Val Lys Met Ser Cys Lys Ala Ser Gly Tyr Ser Phe
        35                  40                  45

Thr Asp Phe Tyr Met Lys Trp Val Lys Gln Ser His Gly Lys Gly Leu
    50                  55                  60

Glu Trp Ile Gly Asp Ile Asp Pro Lys Asn Gly Asp Thr Phe Tyr Asn
65                  70                  75                  80

Gln Lys Phe Lys Gly Arg Ala Thr Leu Thr Val Asp Lys Ser Ser Ser
                85                  90                  95

Thr Ala Tyr Met Gln Leu Asn Ser Leu Thr Thr Glu Asp Ser Ala Val
            100                 105                 110

Tyr Tyr Cys Ala Thr Tyr Tyr Gly Tyr Thr Met Asp Tyr Trp Gly Gln
        115                 120                 125

Gly Thr Ser Val Thr Val Ser Ser Ala Lys Thr Thr Ala Pro Ser Val
    130                 135                 140

Tyr Pro Leu Ala Pro Val Cys Gly Asp Thr Thr Gly Ser Ser Val Thr
145                 150                 155                 160

Leu Gly Cys Leu Val Lys Gly Tyr Phe
                165

<210> SEQ ID NO 63
<211> LENGTH: 165
<212> TYPE: PRT
<213> ORGANISM: Artificial Sequence
<220> FEATURE:
<223> OTHER INFORMATION: antibody sequence

<400> SEQUENCE: 63

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Thr Ser Ser Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr Arg Arg Pro Pro Arg Thr Phe Gly Gly Gly Thr Lys Leu Glu
        115                 120                 125

Ile Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Arg
```

<210> SEQ ID NO 64
<211> LENGTH: 152
<212> TYPE: PRT
<213> ORGANISM: Artificial Sequence
<220> FEATURE:
<223> OTHER INFORMATION: antibody sequence

<400> SEQUENCE: 64

```
Met Asp Phe Gly Leu Ser Trp Val Phe Val Val Phe Tyr Gln Gly
1               5                   10                  15

Val His Cys Glu Val Gln Leu Val Glu Ser Gly Gly Gly Leu Val Gln
                20                  25                  30

Pro Lys Gly Ser Leu Lys Leu Ser Cys Ala Ala Ser Gly Phe Thr Phe
            35                  40                  45

Asn Thr Tyr Ala Met Asn Trp Val Arg Gln Ala Pro Gly Lys Gly Leu
        50                  55                  60

Glu Trp Val Ala Arg Ile Arg Ser Lys Ser Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Met Leu Tyr Leu Gln Met Asn Asn Leu Lys Thr Glu Asp Thr
            100                 105                 110

Ala Met Tyr Tyr Cys Val Arg His Gly Glu Tyr Gly Asn Pro Trp Phe
        115                 120                 125

Ala Tyr Trp Gly Gln Gly Thr Leu Val Thr Val Ser Ala Glu Ser Gln
    130                 135                 140

Ser Phe Pro Asn Val Phe Pro Leu
145                 150
```

<210> SEQ ID NO 65
<211> LENGTH: 166
<212> TYPE: PRT
<213> ORGANISM: Artificial Sequence
<220> FEATURE:
<223> OTHER INFORMATION: antibody sequence

<400> SEQUENCE: 65

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140
```

```
Ser Ser Glu Gln Leu Thr Ser Gly Gly Ala Ser Val Val Cys Phe Leu
145                 150                 155                 160

Asn Asn Phe Tyr Pro Lys
                165

<210> SEQ ID NO 66
<211> LENGTH: 8
<212> TYPE: PRT
<213> ORGANISM: Artificial Sequence
<220> FEATURE:
<223> OTHER INFORMATION: antibody sequence

<400> SEQUENCE: 66

Gly Tyr Thr Phe Thr Glu Tyr Thr
1               5

<210> SEQ ID NO 67
<211> LENGTH: 8
<212> TYPE: PRT
<213> ORGANISM: Artificial Sequence
<220> FEATURE:
<223> OTHER INFORMATION: antibody sequence

<400> SEQUENCE: 67

Ile Asn Pro Asn Asn Gly Gly Thr
1               5

<210> SEQ ID NO 68
<211> LENGTH: 8
<212> TYPE: PRT
<213> ORGANISM: Artificial Sequence
<220> FEATURE:
<223> OTHER INFORMATION: antibody sequence

<400> SEQUENCE: 68

Ala Ser Leu Asp Gly Arg Asp Tyr
1               5

<210> SEQ ID NO 69
<211> LENGTH: 12
<212> TYPE: PRT
<213> ORGANISM: Artificial Sequence
<220> FEATURE:
<223> OTHER INFORMATION: antibody sequence

<400> SEQUENCE: 69

Gln Ser Leu Leu Asn Ser Arg Thr Arg Lys Asn Tyr
1               5                   10

<210> SEQ ID NO 70
<211> LENGTH: 4
<212> TYPE: PRT
<213> ORGANISM: Artificial Sequence
<220> FEATURE:
<223> OTHER INFORMATION: antibody sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 70

Trp Ala Ser Xaa
1

<210> SEQ ID NO 71
<211> LENGTH: 8
<212> TYPE: PRT
```

```
<213> ORGANISM: Artificial Sequence
<220> FEATURE:
<223> OTHER INFORMATION: antibody sequence

<400> SEQUENCE: 71

Lys Gln Ser Tyr Asn Leu Leu Thr
1               5

<210> SEQ ID NO 72
<211> LENGTH: 8
<212> TYPE: PRT
<213> ORGANISM: Artificial Sequence
<220> FEATURE:
<223> OTHER INFORMATION: antibody sequence

<400> SEQUENCE: 72

Gly Phe Thr Phe Asn Thr Tyr Ala
1               5

<210> SEQ ID NO 73
<211> LENGTH: 10
<212> TYPE: PRT
<213> ORGANISM: Artificial Sequence
<220> FEATURE:
<223> OTHER INFORMATION: antibody sequence

<400> SEQUENCE: 73

Ile Arg Ser Lys Ser Asn Asn Tyr Ala Thr
1               5                   10

<210> SEQ ID NO 74
<211> LENGTH: 13
<212> TYPE: PRT
<213> ORGANISM: Artificial Sequence
<220> FEATURE:
<223> OTHER INFORMATION: antibody sequence

<400> SEQUENCE: 74

Val Arg His Gly Glu Tyr Gly Asn Pro Trp Phe Ala Tyr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: antibody sequence

<400> SEQUENCE: 75

Gln Ser Leu Val His Ser Asn Gly Asn Thr Tyr
1               5                   10

<210> SEQ ID NO 76
<211> LENGTH: 4
<212> TYPE: PRT
<213> ORGANISM: Artificial Sequence
<220> FEATURE:
<223> OTHER INFORMATION: antibody sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 76

Lys Val Ser Xaa
1
```

```
<210> SEQ ID NO 77
<211> LENGTH: 9
<212> TYPE: PRT
<213> ORGANISM: Artificial Sequence
<220> FEATURE:
<223> OTHER INFORMATION: antibody sequence

<400> SEQUENCE: 77

Ser Gln Ser Thr His Val Pro Tyr Thr
1               5

<210> SEQ ID NO 78
<211> LENGTH: 5
<212> TYPE: PRT
<213> ORGANISM: Artificial Sequence
<220> FEATURE:
<223> OTHER INFORMATION: core epitope

<400> SEQUENCE: 78

Leu Leu Pro Gln Pro
1               5

<210> SEQ ID NO 79
<211> LENGTH: 7
<212> TYPE: PRT
<213> ORGANISM: Artificial Sequence
<220> FEATURE:
<223> OTHER INFORMATION: core epitope

<400> SEQUENCE: 79

Pro Pro Gln Ala Gln Pro Leu
1               5

<210> SEQ ID NO 80
<211> LENGTH: 6
<212> TYPE: PRT
<213> ORGANISM: Artificial Sequence
<220> FEATURE:
<223> OTHER INFORMATION: core epitope

<400> SEQUENCE: 80

Pro Pro Gln Ala Gln Pro
1               5

<210> SEQ ID NO 81
<211> LENGTH: 4
<212> TYPE: PRT
<213> ORGANISM: Artificial Sequence
<220> FEATURE:
<223> OTHER INFORMATION: core epitope

<400> SEQUENCE: 81

Gln Pro Leu Leu
1

<210> SEQ ID NO 82
<211> LENGTH: 7
<212> TYPE: PRT
<213> ORGANISM: Artificial Sequence
<220> FEATURE:
<223> OTHER INFORMATION: core epitope

<400> SEQUENCE: 82

Pro Gln Ala Gln Pro Leu Leu
1               5

<210> SEQ ID NO 83
```

```
<211> LENGTH: 8
<212> TYPE: PRT
<213> ORGANISM: Artificial Sequence
<220> FEATURE:
<223> OTHER INFORMATION: core epitope

<400> SEQUENCE: 83

Gln Tyr Leu Gly Leu Gln Ile Gly
1               5

<210> SEQ ID NO 84
<211> LENGTH: 7
<212> TYPE: PRT
<213> ORGANISM: Artificial Sequence
<220> FEATURE:
<223> OTHER INFORMATION: core epitope

<400> SEQUENCE: 84

Tyr Leu Gly Leu Gln Ile Gly
1               5

<210> SEQ ID NO 85
<211> LENGTH: 10
<212> TYPE: PRT
<213> ORGANISM: Artificial Sequence
<220> FEATURE:
<223> OTHER INFORMATION: core epitope

<400> SEQUENCE: 85

Asp Asn Gln Tyr Leu Gly Leu Gln Ile Gly
1               5                   10

<210> SEQ ID NO 86
<211> LENGTH: 7
<212> TYPE: PRT
<213> ORGANISM: Artificial Sequence
<220> FEATURE:
<223> OTHER INFORMATION: core epitope

<400> SEQUENCE: 86

Asp Asn Gln Tyr Leu Gly Leu
1               5

<210> SEQ ID NO 87
<211> LENGTH: 7
<212> TYPE: PRT
<213> ORGANISM: Artificial Sequence
<220> FEATURE:
<223> OTHER INFORMATION: core epitope

<400> SEQUENCE: 87

Tyr Leu Gly Leu Gln Ile Gly
1               5

<210> SEQ ID NO 88
<211> LENGTH: 10
<212> TYPE: PRT
<213> ORGANISM: Artificial Sequence
<220> FEATURE:
<223> OTHER INFORMATION: immunogenic peptide

<400> SEQUENCE: 88

Asp Asn Gln Tyr Leu Gly Leu Gln Ile Cys
1               5                   10

<210> SEQ ID NO 89
<211> LENGTH: 11
```

```
<212> TYPE: PRT
<213> ORGANISM: Artificial Sequence
<220> FEATURE:
<223> OTHER INFORMATION: immunogenic peptide

<400> SEQUENCE: 89

Thr Asp Asn Gln Tyr Leu Gly Leu Gln Ile Cys
1               5                   10

<210> SEQ ID NO 90
<211> LENGTH: 12
<212> TYPE: PRT
<213> ORGANISM: Artificial Sequence
<220> FEATURE:
<223> OTHER INFORMATION: immunogenic peptide

<400> SEQUENCE: 90

Thr Asp Asn Gln Tyr Leu Gly Leu Gln Ile Gly Cys
1               5                   10

<210> SEQ ID NO 91
<211> LENGTH: 14
<212> TYPE: PRT
<213> ORGANISM: Artificial Sequence
<220> FEATURE:
<223> OTHER INFORMATION: immunogenic peptide

<400> SEQUENCE: 91

Lys Thr Asp Asn Gln Tyr Leu Gly Leu Gln Ile Gly Lys Cys
1               5                   10

<210> SEQ ID NO 92
<211> LENGTH: 15
<212> TYPE: PRT
<213> ORGANISM: Artificial Sequence
<220> FEATURE:
<223> OTHER INFORMATION: immunogenic peptide

<400> SEQUENCE: 92

Gly Thr Asp Asn Gln Tyr Leu Gly Leu Gln Ile Gly Lys Lys Cys
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: immunogenic peptide

<400> SEQUENCE: 93

Lys Thr Asp Asn Gln Tyr Leu Gly Leu Gln Ile Lys Lys Gly Cys
1               5                   10                  15

<210> SEQ ID NO 94
<211> LENGTH: 14
<212> TYPE: PRT
<213> ORGANISM: Artificial Sequence
<220> FEATURE:
<223> OTHER INFORMATION: immunogenic peptide

<400> SEQUENCE: 94

Lys Asp Asn Gln Tyr Leu Gly Leu Gln Ile Lys Lys Gly Cys
1               5                   10

<210> SEQ ID NO 95
<211> LENGTH: 109
<212> TYPE: PRT
```

<213> ORGANISM: Artificial Sequence
<220> FEATURE:
<223> OTHER INFORMATION: humanised antibody sequence

<400> SEQUENCE: 95

```
Glu Ile Val Leu Thr Gln Ser Pro Ser Leu Ser Ala Ser Val Gly
1               5                   10                  15

Asp Arg Val Thr Ile Thr Cys Thr Ala Ser Ser Ser Val Thr Ser
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys His Gln Tyr Arg Arg Pro Pro
                85                  90                  95

Arg Thr Phe Gly Gly Gly Thr Lys Leu Glu Ile Lys Arg
            100                 105
```

<210> SEQ ID NO 96
<211> LENGTH: 117
<212> TYPE: PRT
<213> ORGANISM: Artificial Sequence
<220> FEATURE:
<223> OTHER INFORMATION: humanised antibody sequence

<400> SEQUENCE: 96

```
Glu Val Gln Leu Val Glu Ser Gly Pro Glu Val Lys Lys Pro Gly Ala
1               5                   10                  15

Thr Val Lys Ile Ser Cys Lys Val Ser Gly Tyr Thr Phe Thr Asp Phe
            20                  25                  30

Tyr Met Lys Trp Val Gln Gln Ala Pro Gly Arg Gly Leu Glu Trp Met
        35                  40                  45

Gly Asp Ile Asp Pro Lys Asn Gly Asp Thr Phe Tyr Asn Gln Lys Phe
50                  55                  60

Lys Gly Arg Val Thr Met Thr Ala Asp Thr Ser Thr Gly Thr Ala Tyr
65                  70                  75                  80

Met Gln Leu Ser Ser Leu Thr Ser Glu Asp Thr Ala Val Tyr Phe Cys
                85                  90                  95

Ala Ser Tyr Tyr Gly Tyr Thr Met Asp Tyr Trp Gly Gln Gly Thr Thr
            100                 105                 110

Val Thr Val Ala Ser
        115
```

<210> SEQ ID NO 97
<211> LENGTH: 112
<212> TYPE: PRT
<213> ORGANISM: Artificial Sequence
<220> FEATURE:
<223> OTHER INFORMATION: humanised antibody sequence

<400> SEQUENCE: 97

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45
```

```
Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65              70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gly Gly Thr Lys Leu Glu Ile Lys
            100                 105                 110

<210> SEQ ID NO 98
<211> LENGTH: 115
<212> TYPE: PRT
<213> ORGANISM: Artificial Sequence
<220> FEATURE:
<223> OTHER INFORMATION: humanised antibody sequence

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Pro Gly Arg Gly Leu Glu Trp Met
            35                  40                  45

Gly Gly Ile Asn Pro Asn Asn Gly Gly Thr Arg Tyr Asn Gln Lys Phe
        50                  55                  60

Lys Gly Arg Val Thr Met Thr Arg Asp Thr Ser Ile Arg Thr Ala Tyr
65              70                  75                  80

Val Glu Leu Ser Arg Leu Thr Ser Asp Asp Thr Ala Val Tyr Tyr Cys
                85                  90                  95

Ala Ser Leu Asp Gly Arg Asp Tyr Trp Gly Gln Gly Thr Leu Val Thr
            100                 105                 110

Val Ser Ser
        115

<210> SEQ ID NO 99
<211> LENGTH: 4
<212> TYPE: PRT
<213> ORGANISM: Artificial Sequence
<220> FEATURE:
<223> OTHER INFORMATION: Synthetic peptide

<400> SEQUENCE: 99

Lys Lys Gly Cys
1

<210> SEQ ID NO 100
<211> LENGTH: 4
<212> TYPE: PRT
<213> ORGANISM: Artificial Sequence
<220> FEATURE:
<223> OTHER INFORMATION: Synthetic peptide

<400> SEQUENCE: 100

Lys Lys Cys Gly
1

<210> SEQ ID NO 101
<211> LENGTH: 4
<212> TYPE: PRT
<213> ORGANISM: Artificial Sequence
<220> FEATURE:
```

-continued

<223> OTHER INFORMATION: Synthetic peptide

<400> SEQUENCE: 101

Ile Val Leu Asp
1

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide

<400> SEQUENCE: 102

Ser Ser Glu Ile Val Leu Asp
1               5

<210> SEQ ID NO 103
<211> LENGTH: 18
<212> TYPE: PRT
<213> ORGANISM: Artificial Sequence
<220> FEATURE:
<223> OTHER INFORMATION: Synthetic peptide

<400> SEQUENCE: 103

Leu Pro Gln Pro Pro Pro Gln Ala Gln Pro Leu Leu Pro Gln Pro Gln
1               5                   10                  15

Pro Cys

<210> SEQ ID NO 104
<211> LENGTH: 11
<212> TYPE: PRT
<213> ORGANISM: Artificial Sequence
<220> FEATURE:
<223> OTHER INFORMATION: Synthetic peptide

<400> SEQUENCE: 104

Cys Pro Ser Asp Ser Ser Glu Ile Val Leu Asp
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Synthetic peptide

<400> SEQUENCE: 105

Gly Thr Asp Asn Gln Tyr Leu Gly Leu Gln Ile Gly Cys
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Synthetic peptide

<400> SEQUENCE: 106

Leu Pro Gln Pro Pro Pro Gln Ala Gln Pro Leu Leu Pro Cys
1               5                   10

<210> SEQ ID NO 107
<211> LENGTH: 13
<212> TYPE: PRT
<213> ORGANISM: Artificial Sequence

```
<220> FEATURE:
<223> OTHER INFORMATION: Synthetic peptide

<400> SEQUENCE: 107

Cys Gly Pro Ala Val Ala Glu Glu Pro Leu His Arg Pro
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Synthetic peptide

<400> SEQUENCE: 108

Ser Asp Ser Ser Glu Ile Val Leu Asp Gly Thr Asp Cys
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Synthetic peptide

<400> SEQUENCE: 109

Glu Ile Val Leu Asp Gly Thr Asp Asn Gln Tyr Leu Cys
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Synthetic peptide

<400> SEQUENCE: 110

Ile Val Leu Asp Gly Thr Asp Asn Gln Tyr Leu Gly Cys
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Synthetic peptide

<400> SEQUENCE: 111

Val Leu Asp Gly Thr Asp Asn Gln Tyr Leu Gly Leu Cys
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic peptide

<400> SEQUENCE: 112

Leu Asp Gly Thr Asp Asn Gln Tyr Leu Gly Leu Gln Cys
1               5                   10

<210> SEQ ID NO 113
<211> LENGTH: 14
<212> TYPE: PRT
<213> ORGANISM: Artificial Sequence
<220> FEATURE:
```

<223> OTHER INFORMATION: Synthetic peptide

<400> SEQUENCE: 113

Asp Gly Thr Asp Asn Gln Tyr Leu Gly Leu Gln Ile Gly Cys
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Synthetic peptide

<400> SEQUENCE: 114

Cys Thr Asp Asn Gln Tyr Leu Gly Leu Gln Ile Gly Gln
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Synthetic peptide

<400> SEQUENCE: 115

Cys Gly Thr Asp Asn Gln Tyr Leu Gly Leu Gln Ile Gly
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Synthetic peptide

<400> SEQUENCE: 116

Cys Asp Asn Gln Tyr Leu Gly Leu Gln Ile Gly Gln Pro
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Synthetic peptide

<400> SEQUENCE: 117

Cys Asn Gln Tyr Leu Gly Leu Gln Ile Gly Gln Pro Gln
1               5                   10

<210> SEQ ID NO 118
<211> LENGTH: 16
<212> TYPE: PRT
<213> ORGANISM: Artificial Sequence
<220> FEATURE:
<223> OTHER INFORMATION: Synthetic peptide

<400> SEQUENCE: 118

Cys Pro Gln Leu Pro Gln Pro Pro Gln Ala Gln Pro Leu Leu Pro
1               5                   10                  15

<210> SEQ ID NO 119
<211> LENGTH: 13
<212> TYPE: PRT
<213> ORGANISM: Artificial Sequence
<220> FEATURE:
<223> OTHER INFORMATION: Synthetic peptide

<400> SEQUENCE: 119

Thr Asp Asn Gln Tyr Leu Gly Leu Gln Ile Gly Gln Cys
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Synthetic peptide

<400> SEQUENCE: 120

Asp Asn Gln Tyr Leu Gly Leu Gln Ile Gly Gln Pro Cys
1               5                   10

<210> SEQ ID NO 121
<211> LENGTH: 23
<212> TYPE: PRT
<213> ORGANISM: Artificial Sequence
<220> FEATURE:
<223> OTHER INFORMATION: Synthetic peptide

<400> SEQUENCE: 121

Pro Pro Pro Gln Leu Pro Gln Pro Pro Gln Ala Gln Pro Leu Leu
1               5                   10                  15

Pro Gln Pro Gln Pro Ala Cys
            20

<210> SEQ ID NO 122
<211> LENGTH: 13
<212> TYPE: PRT
<213> ORGANISM: Artificial Sequence
<220> FEATURE:
<223> OTHER INFORMATION: Synthetic peptide

<400> SEQUENCE: 122

Pro Ser Asp Ser Ser Glu Ile Val Leu Asp Gly Thr Cys
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Synthetic peptide

<400> SEQUENCE: 123

Asp Ser Ser Glu Ile Val Leu Asp Gly Thr Asp Asn Cys
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Synthetic peptide

<400> SEQUENCE: 124

Ser Glu Ile Val Leu Asp Gly Thr Asp Asn Gln Tyr Cys
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Synthetic peptide

<400> SEQUENCE: 125

Asn Gln Tyr Leu Gly Leu Gln Ile Gly Gln Pro Gln Cys
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Synthetic peptide

<400> SEQUENCE: 126

Gln Tyr Leu Gly Leu Gln Ile Gly Gln Pro Gln Asp Cys
1               5                   10

<210> SEQ ID NO 127
<211> LENGTH: 20
<212> TYPE: PRT
<213> ORGANISM: Artificial Sequence
<220> FEATURE:
<223> OTHER INFORMATION: Synthetic peptide

<400> SEQUENCE: 127

Cys Ala Met Ala Thr Leu Glu Lys Leu Met Lys Ala Phe Glu Ser Leu
1               5                   10                  15

Lys Ser Phe Gln
            20

<210> SEQ ID NO 128
<211> LENGTH: 15
<212> TYPE: PRT
<213> ORGANISM: Artificial Sequence
<220> FEATURE:
<223> OTHER INFORMATION: Synthetic peptide

<400> SEQUENCE: 128

Cys Ala Lys Leu Met Lys Ala Phe Glu Ser Leu Lys Ser Phe Gln
1               5                   10                  15

<210> SEQ ID NO 129
<211> LENGTH: 13
<212> TYPE: PRT
<213> ORGANISM: Artificial Sequence
<220> FEATURE:
<223> OTHER INFORMATION: Synthetic peptide

<400> SEQUENCE: 129

Cys Glu Glu Gln Gln Arg Gln Gln Gln Gln Gln Gln Gln
1               5                   10

<210> SEQ ID NO 130
<211> LENGTH: 19
<212> TYPE: PRT
<213> ORGANISM: Artificial Sequence
<220> FEATURE:
<223> OTHER INFORMATION: Synthetic peptide

<400> SEQUENCE: 130

Gln Gln Gln Gln Gln Gln Pro Pro Pro Pro Pro Pro Pro Ala Lys
1               5                   10                  15

Lys Lys Cys

```
<210> SEQ ID NO 131
<211> LENGTH: 7
<212> TYPE: PRT
<213> ORGANISM: Artificial Sequence
<220> FEATURE:
<223> OTHER INFORMATION: Synthetic peptide

<400> SEQUENCE: 131

Cys Ser Glu Ile Val Leu Asp
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic peptide

<400> SEQUENCE: 132

Cys Ser Ser Glu Ile Val Leu Asp
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic peptide

<400> SEQUENCE: 133

Cys Asp Ser Ser Glu Ile Val Leu Asp
1               5

<210> SEQ ID NO 134
<211> LENGTH: 10
<212> TYPE: PRT
<213> ORGANISM: Artificial Sequence
<220> FEATURE:
<223> OTHER INFORMATION: Synthetic peptide

<400> SEQUENCE: 134

Cys Ser Asp Ser Ser Glu Ile Val Leu Asp
1               5                   10

<210> SEQ ID NO 135
<211> LENGTH: 9
<212> TYPE: PRT
<213> ORGANISM: Artificial Sequence
<220> FEATURE:
<223> OTHER INFORMATION: Synthetic peptide

<400> SEQUENCE: 135

Cys Ser Glu Ile Val Leu Asp Gly Thr
1               5

<210> SEQ ID NO 136
<211> LENGTH: 6
<212> TYPE: PRT
<213> ORGANISM: Artificial Sequence
<220> FEATURE:
<223> OTHER INFORMATION: Synthetic peptide

<400> SEQUENCE: 136

Cys Glu Ile Val Leu Asp
1               5

<210> SEQ ID NO 137
```

```
<211> LENGTH: 5
<212> TYPE: PRT
<213> ORGANISM: Artificial Sequence
<220> FEATURE:
<223> OTHER INFORMATION: Synthetic peptide

<400> SEQUENCE: 137

Cys Ile Val Leu Asp
1               5

<210> SEQ ID NO 138
<211> LENGTH: 6
<212> TYPE: PRT
<213> ORGANISM: Artificial Sequence
<220> FEATURE:
<223> OTHER INFORMATION: Synthetic peptide

<400> SEQUENCE: 138

Cys Ser Glu Ile Val Leu
1               5

<210> SEQ ID NO 139
<211> LENGTH: 14
<212> TYPE: PRT
<213> ORGANISM: Artificial Sequence
<220> FEATURE:
<223> OTHER INFORMATION: Synthetic peptide

<400> SEQUENCE: 139

Cys Ser Glu Ile Val Leu Asp Gly Thr Asp Asn Gln Tyr Leu
1               5                   10

<210> SEQ ID NO 140
<211> LENGTH: 14
<212> TYPE: PRT
<213> ORGANISM: Artificial Sequence
<220> FEATURE:
<223> OTHER INFORMATION: Synthetic peptide

<400> SEQUENCE: 140

Cys Ser Asp Ser Ser Glu Ile Val Leu Asp Gly Thr Asp Asn
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Synthetic peptide

<400> SEQUENCE: 141

Ser Glu Ile Val Leu Asp Gly Thr Asp Asn Gln Tyr Leu Cys
1               5                   10

<210> SEQ ID NO 142
<211> LENGTH: 14
<212> TYPE: PRT
<213> ORGANISM: Artificial Sequence
<220> FEATURE:
<223> OTHER INFORMATION: Synthetic peptide

<400> SEQUENCE: 142

Cys Ala Glu Ile Val Leu Asp Gly Thr Asp Asn Gln Tyr Leu
1               5                   10

<210> SEQ ID NO 143
<211> LENGTH: 14
```

```
<212> TYPE: PRT
<213> ORGANISM: Artificial Sequence
<220> FEATURE:
<223> OTHER INFORMATION: Synthetic peptide

<400> SEQUENCE: 143

Cys Ser Ala Ile Val Leu Asp Gly Thr Asp Asn Gln Tyr Leu
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Synthetic peptide

<400> SEQUENCE: 144

Cys Ser Glu Ala Val Leu Asp Gly Thr Asp Asn Gln Tyr Leu
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Synthetic peptide

<400> SEQUENCE: 145

Cys Ser Glu Ile Ala Leu Asp Gly Thr Asp Asn Gln Tyr Leu
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Synthetic peptide

<400> SEQUENCE: 146

Cys Ser Glu Ile Val Ala Asp Gly Thr Asp Asn Gln Tyr Leu
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Synthetic peptide

<400> SEQUENCE: 147

Cys Ser Glu Ile Val Leu Ala Gly Thr Asp Asn Gln Tyr Leu
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Synthetic peptide

<400> SEQUENCE: 148

Cys Ser Glu Ile Val Leu Asp Ala Thr Asp Asn Gln Tyr Leu
1               5                   10

<210> SEQ ID NO 149
<211> LENGTH: 14
<212> TYPE: PRT
```

```
<213> ORGANISM: Artificial Sequence
<220> FEATURE:
<223> OTHER INFORMATION: Synthetic peptide

<400> SEQUENCE: 149

Cys Ser Glu Ile Val Leu Asp Gly Ala Asp Asn Gln Tyr Leu
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Synthetic peptide

<400> SEQUENCE: 150

Cys Ser Glu Ile Val Leu Asp Gly Thr Ala Asn Gln Tyr Leu
1               5                   10

<210> SEQ ID NO 151
<211> LENGTH: 14
<212> TYPE: PRT
<213> ORGANISM: Artificial Sequence
<220> FEATURE:
<223> OTHER INFORMATION: Synthetic peptide

<400> SEQUENCE: 151

Cys Ser Glu Ile Val Leu Asp Gly Thr Asp Ala Gln Tyr Leu
1               5                   10

<210> SEQ ID NO 152
<211> LENGTH: 14
<212> TYPE: PRT
<213> ORGANISM: Artificial Sequence
<220> FEATURE:
<223> OTHER INFORMATION: Synthetic peptide

<400> SEQUENCE: 152

Cys Ser Glu Ile Val Leu Asp Gly Thr Asp Asn Ala Tyr Leu
1               5                   10

<210> SEQ ID NO 153
<211> LENGTH: 14
<212> TYPE: PRT
<213> ORGANISM: Artificial Sequence
<220> FEATURE:
<223> OTHER INFORMATION: Synthetic peptide

<400> SEQUENCE: 153

Cys Ser Glu Ile Val Leu Asp Gly Thr Asp Asn Gln Ala Leu
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Synthetic peptide

<400> SEQUENCE: 154

Cys Ser Glu Ile Val Leu Asp Gly Thr Asp Asn Gln Tyr Ala
1               5                   10
```